(12) United States Patent
Ghaffari et al.

(10) Patent No.: US 10,467,926 B2
(45) Date of Patent: Nov. 5, 2019

(54) CONFORMAL SENSOR SYSTEMS FOR SENSING AND ANALYSIS

(71) Applicant: MC10, Inc., Lexington, MA (US)

(72) Inventors: Roozbeh Ghaffari, Cambridge, MA (US); Isaiah Kacyvenski, Weston, MA (US); Conor Rafferty, Cambridge, MA (US); Milan Raj, Cambridge, MA (US); Melissa Ceruolo, Swampscott, MA (US); Yung-Yu Hsu, San Jose, CA (US); Bryan Keen, Somerville, MA (US); Briana Morey, Somerville, MA (US); Brian Reilly, Cambridge, MA (US); Ping-Hung Wei, Burlingame, CA (US)

(73) Assignee: MC10, Inc., Lexington, MA (US)

( * ) Notice: Subject to any disclaimer, the term of this patent is extended or adjusted under 35 U.S.C. 154(b) by 272 days.

(21) Appl. No.: 15/023,556

(22) PCT Filed: Oct. 7, 2014

(86) PCT No.: PCT/US2014/059566
§ 371 (c)(1),
(2) Date: Mar. 21, 2016

(87) PCT Pub. No.: WO2015/054312
PCT Pub. Date: Apr. 16, 2015

(65) Prior Publication Data
US 2016/0232807 A1  Aug. 11, 2016

Related U.S. Application Data

(60) Provisional application No. 61/887,696, filed on Oct. 7, 2013, provisional application No. 61/902,151, filed
(Continued)

(51) Int. Cl.
*G09B 19/00* (2006.01)
*A61B 5/0488* (2006.01)
(Continued)

(52) U.S. Cl.
CPC ............ *G09B 19/00* (2013.01); *A61B 5/0488* (2013.01); *A61B 5/1118* (2013.01);
(Continued)

(58) Field of Classification Search
CPC .. G09B 19/00; G09B 19/003; G09B 19/0038; A61B 5/0488; A61B 5/1118;
(Continued)

(56) References Cited

U.S. PATENT DOCUMENTS 3,716,861 A  2/1973  Root
3,805,427 A  4/1974  Epstein
(Continued)

FOREIGN PATENT DOCUMENTS

EP  0585670 A2  3/1994
EP  0779059 A1  6/1997
(Continued)

OTHER PUBLICATIONS

Carvalhal et al., "Electrochemical Detection in a Paper-Based Separation Device", Analytical Chemistry, vol. 82, No. 3, (1162-1165) (4 pages) (Jan. 7, 2010).
(Continued)

*Primary Examiner* — Corbett B Coburn
(74) *Attorney, Agent, or Firm* — Nixon Peabody LLP

(57) ABSTRACT

Conformal sensor systems and devices are used for sensing and analysis of data indicative of body motion, e.g., for such applications as training and/or clinical purposes. Flexible electronics technology can be implemented as conformal sensors for sensing or measuring motion (including body motion and/or muscle activity), heart rate, electrical activity,
(Continued)

and/or body temperature for such applications as medical diagnosis, medical treatment, physical activity, physical therapy and/or clinical purposes. The conformal sensors can be used for detecting and quantifying impact, and can be used for central nervous system disease monitoring.

23 Claims, 28 Drawing Sheets

Related U.S. Application Data on Nov. 8, 2013, provisional application No. 62/002,773, filed on May 23, 2014, provisional application No. 62/058,318, filed on Oct. 1, 2014.

(51) Int. Cl.
| | | |
|---|---|---|
| A61B 5/11 | (2006.01) | |
| G01P 7/00 | (2006.01) | |
| A61B 5/00 | (2006.01) | |
| H04W 4/38 | (2018.01) | |
| H04W 4/80 | (2018.01) | |
| G16H 50/20 | (2018.01) | |
| G16H 20/30 | (2018.01) | |
| H04W 80/00 | (2009.01) | |

(52) U.S. Cl.
CPC .......... *A61B 5/1124* (2013.01); *A61B 5/7275* (2013.01); *G01P 7/00* (2013.01); *G09B 19/003* (2013.01); *G09B 19/0038* (2013.01); *G16H 20/30* (2018.01); *G16H 50/20* (2018.01); *H04W 4/38* (2018.02); *H04W 4/80* (2018.02); *A61B 5/1126* (2013.01); *A61B 5/7246* (2013.01); *A61B 2505/09* (2013.01); *H04W 80/00* (2013.01)

(58) Field of Classification Search
CPC ....... A61B 5/1124; A61B 5/7275; G01B 7/00; H04W 4/006; H04W 4/008
See application file for complete search history.

(56) References Cited

U.S. PATENT DOCUMENTS

| | | |
|---|---|---|
| 3,838,240 A | 9/1974 | Schelhorn |
| 4,278,474 A | 7/1981 | Blakeslee |
| 4,304,235 A | 12/1981 | Kaufman |
| 4,416,288 A | 11/1983 | Freeman |
| 4,658,153 A | 4/1987 | Brosh |
| 5,272,375 A | 12/1993 | Belopolsky |
| 5,306,917 A | 4/1994 | Black |
| 5,326,521 A | 7/1994 | East |
| 5,331,966 A | 7/1994 | Bennett |
| 5,360,987 A | 11/1994 | Shibib |
| 5,471,982 A | 5/1995 | Edwards |
| 5,454,270 A | 10/1995 | Brown |
| 5,491,651 A | 2/1996 | Janic |
| 5,567,975 A | 10/1996 | Walsh |
| 5,580,794 A | 12/1996 | Allen |
| 5,617,870 A | 4/1997 | Hastings |
| 5,811,790 A | 9/1998 | Endo |
| 5,817,008 A | 10/1998 | Rafert |
| 5,907,477 A | 5/1999 | Tuttle |
| 6,063,046 A | 5/2000 | Allum |
| 6,265,090 B1 | 7/2001 | Nishide |
| 6,282,960 B1 | 9/2001 | Samuels |
| 6,343,514 B1 | 2/2002 | Smith |
| 6,387,052 B1 | 5/2002 | Quinn |
| 6,410,971 B1 | 6/2002 | Otey |
| 6,421,016 B1 | 7/2002 | Phillips |
| 6,455,931 B1 | 9/2002 | Hamilton |
| 6,567,158 B1 | 5/2003 | Falcial |
| 6,626,940 B2 | 9/2003 | Crowley |
| 6,641,860 B1 | 11/2003 | Kaiserman |
| 6,775,906 B1 | 8/2004 | Silverbrook |
| 6,784,844 B1 | 8/2004 | Boakes |
| 6,965,160 B2 | 11/2005 | Cobbley |
| 6,987,314 B1 | 1/2006 | Yoshida |
| 7,259,030 B2 | 8/2007 | Daniels |
| 7,265,298 B2 | 9/2007 | Maghribi |
| 7,302,751 B2 | 12/2007 | Hamburgen |
| 7,337,012 B2 | 2/2008 | Maghribi |
| 7,487,587 B2 | 2/2009 | Vanfleteren |
| 7,491,892 B2 | 2/2009 | Wagner |
| 7,521,292 B2 | 4/2009 | Rogers |
| 7,557,367 B2 | 7/2009 | Rogers |
| 7,602,301 B1 | 10/2009 | Stirling |
| 7,618,260 B2 | 11/2009 | Daniel |
| 7,622,367 B1 | 11/2009 | Nuzzo |
| 7,727,228 B2 | 6/2010 | Abboud |
| 7,739,791 B2 | 6/2010 | Brandenburg |
| 7,759,167 B2 | 7/2010 | Vanfleteren |
| 7,815,095 B2 | 10/2010 | Fujisawa |
| 7,960,246 B2 | 6/2011 | Flamand |
| 7,982,296 B2 | 7/2011 | Nuzzo |
| 8,097,926 B2 | 1/2012 | De Graff |
| 8,198,621 B2 | 6/2012 | Rogers |
| 8,207,473 B2 | 6/2012 | Axisa |
| 8,217,381 B2 | 7/2012 | Rogers |
| 8,372,726 B2 | 2/2013 | De Graff |
| 8,389,862 B2 | 3/2013 | Arora |
| 8,431,828 B2 | 4/2013 | Vanfleteren |
| 8,440,546 B2 | 5/2013 | Nuzzo |
| 8,536,667 B2 | 9/2013 | De Graff |
| 8,552,299 B2 | 10/2013 | Rogers |
| 8,618,656 B2 | 12/2013 | Oh |
| 8,664,699 B2 | 3/2014 | Nuzzo |
| 8,679,888 B2 | 3/2014 | Rogers |
| 8,729,524 B2 | 5/2014 | Rogers |
| 8,754,396 B2 | 6/2014 | Rogers |
| 8,865,489 B2 | 10/2014 | Rogers |
| 8,886,334 B2 | 11/2014 | Ghaffari |
| 8,905,772 B2 | 12/2014 | Rogers |
| 9,012,784 B2 | 4/2015 | Arora |
| 9,082,025 B2 | 7/2015 | Fastert |
| 9,105,555 B2 | 8/2015 | Rogers |
| 9,105,782 B2 | 8/2015 | Rogers |
| 9,119,533 B2 | 9/2015 | Ghaffari |
| 9,123,614 B2 | 9/2015 | Graff |
| 9,159,635 B2 | 10/2015 | Elolampi |
| 9,168,094 B2 | 10/2015 | Lee |
| 9,171,794 B2 | 10/2015 | Rafferty |
| 9,186,060 B2 | 11/2015 | De Graff |
| 9,226,402 B2 | 12/2015 | Hsu |
| 9,247,637 B2 | 1/2016 | Hsu |
| 9,289,132 B2 | 3/2016 | Ghaffari |
| 9,295,842 B2 | 3/2016 | Ghaffari |
| 9,324,733 B2 | 4/2016 | Rogers |
| 2001/0012918 A1 | 8/2001 | Swanson |
| 2001/0021867 A1 | 9/2001 | Kordis |
| 2002/0026127 A1 | 2/2002 | Balbierz |
| 2002/0082515 A1 | 6/2002 | Campbell |
| 2002/0094701 A1 | 7/2002 | Biegelsen |
| 2002/0107436 A1 | 8/2002 | Barton |
| 2002/0113739 A1 | 8/2002 | Howard |
| 2002/0128700 A1 | 9/2002 | Cross, Jr. |
| 2002/0145467 A1 | 10/2002 | Minch |
| 2002/0151934 A1 | 10/2002 | Levine |
| 2002/0158330 A1 | 10/2002 | Moon |
| 2003/0017848 A1 | 1/2003 | Engstrom |
| 2003/0045025 A1 | 3/2003 | Coyle |
| 2003/0097165 A1 | 5/2003 | Krulevitch |
| 2003/0120271 A1 | 6/2003 | Burnside |
| 2003/0162507 A1 | 8/2003 | Vatt |
| 2003/0214408 A1 | 11/2003 | Grajales |
| 2003/0236455 A1 | 12/2003 | Swanson |
| 2004/0006264 A1 | 1/2004 | Mojarradi |
| 2004/0085469 A1 | 5/2004 | Johnson |
| 2004/0092806 A1 | 5/2004 | Sagon |
| 2004/0106334 A1 | 6/2004 | Suzuki |
| 2004/0135094 A1 | 7/2004 | Niigaki |

(56) References Cited

U.S. PATENT DOCUMENTS

| | | |
|---|---|---|
| 2004/0138558 A1 | 7/2004 | Dunki-Jacobs |
| 2004/0149921 A1 | 8/2004 | Smyk |
| 2004/0178466 A1 | 9/2004 | Merrill |
| 2004/0192082 A1 | 9/2004 | Wagner |
| 2004/0201134 A1 | 10/2004 | Kawai |
| 2004/0203486 A1 | 10/2004 | Shepherd |
| 2004/0221370 A1 | 11/2004 | Hannula |
| 2004/0243204 A1 | 12/2004 | Maghribi |
| 2005/0021103 A1 | 1/2005 | DiLorenzo |
| 2005/0029680 A1 | 2/2005 | Jung |
| 2005/0067293 A1 | 3/2005 | Naito |
| 2005/0070778 A1 | 3/2005 | Lackey |
| 2005/0096513 A1 | 5/2005 | Ozguz |
| 2005/0113744 A1 | 5/2005 | Donoghue |
| 2005/0139683 A1 | 6/2005 | Yi |
| 2005/0171524 A1 | 8/2005 | Stern |
| 2005/0203366 A1 | 9/2005 | Donoghue |
| 2005/0248312 A1 | 11/2005 | Cao |
| 2005/0285262 A1 | 12/2005 | Knapp |
| 2006/0003709 A1 | 1/2006 | Wood |
| 2006/0038182 A1 | 2/2006 | Rogers |
| 2006/0071349 A1 | 4/2006 | Tokushige |
| 2006/0084394 A1 | 4/2006 | Engstrom |
| 2006/0106321 A1 | 5/2006 | Lewinsky |
| 2006/0128346 A1 | 6/2006 | Yasui |
| 2006/0154398 A1 | 7/2006 | Qing |
| 2006/0160560 A1 | 7/2006 | Josenhans |
| 2006/0248946 A1 | 11/2006 | Howell |
| 2006/0257945 A1 | 11/2006 | Masters |
| 2006/0264767 A1 | 11/2006 | Shennib |
| 2006/0265187 A1* | 11/2006 | Vock ............. A42B 3/0433 |
| | | 702/182 |
| 2006/0270135 A1 | 11/2006 | Chrysler |
| 2006/0286785 A1 | 12/2006 | Rogers |
| 2007/0027514 A1 | 2/2007 | Gerber |
| 2007/0031283 A1 | 2/2007 | Davis |
| 2007/0108389 A1 | 5/2007 | Makela |
| 2007/0113399 A1 | 5/2007 | Kumar |
| 2007/0123756 A1 | 5/2007 | Kitajima |
| 2007/0270672 A1 | 11/2007 | Hayter |
| 2008/0036097 A1 | 2/2008 | Ito |
| 2008/0046080 A1 | 2/2008 | Vanden Bulcke |
| 2008/0067247 A1* | 3/2008 | McGregor ............. G06K 19/07 |
| | | 235/439 |
| 2008/0074383 A1 | 3/2008 | Dean |
| 2008/0096620 A1 | 4/2008 | Lee |
| 2008/0139894 A1 | 6/2008 | Szydlo-Moore |
| 2008/0157235 A1 | 7/2008 | Rogers |
| 2008/0188912 A1 | 8/2008 | Stone |
| 2008/0193749 A1 | 8/2008 | Thompson |
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0287167 A1 | 11/2008 | Caine |
| 2008/0313552 A1 | 12/2008 | Buehler |
| 2009/0000377 A1 | 1/2009 | Shipps |
| 2009/0001550 A1 | 1/2009 | Yonggang |
| 2009/0015560 A1 | 1/2009 | Robinson |
| 2009/0017884 A1 | 1/2009 | Rotschild |
| 2009/0048556 A1 | 2/2009 | Durand |
| 2009/0088750 A1 | 4/2009 | Hushka |
| 2009/0107704 A1 | 4/2009 | Vanfleteren |
| 2009/0131165 A1* | 5/2009 | Buchner ............. A63F 13/02 |
| | | 463/30 |
| 2009/0154736 A1 | 6/2009 | Lee |
| 2009/0184254 A1 | 7/2009 | Miura |
| 2009/0204168 A1 | 8/2009 | Kallmeyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0273909 A1 | 11/2009 | Shin |
| 2009/0283891 A1 | 11/2009 | Dekker |
| 2009/0291508 A1 | 11/2009 | Babu |
| 2009/0294803 A1 | 12/2009 | Nuzzo |
| 2009/0306485 A1* | 12/2009 | Bell ............. A61B 5/04085 |
| | | 600/301 |
| 2009/0322480 A1 | 12/2009 | Benedict |
| 2010/0002402 A1 | 1/2010 | Rogers |
| 2010/0059863 A1 | 3/2010 | Rogers |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |
| 2010/0090824 A1 | 4/2010 | Rowell |
| 2010/0116526 A1 | 5/2010 | Arora |
| 2010/0117660 A1 | 5/2010 | Douglas |
| 2010/0178722 A1 | 7/2010 | De Graff |
| 2010/0245011 A1 | 9/2010 | Chatzopoulos |
| 2010/0249557 A1* | 9/2010 | Besko ............. A61B 5/14553 |
| | | 600/340 |
| 2010/0271191 A1 | 10/2010 | De Graff |
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0022125 A1* | 1/2011 | Olson ............. A61N 1/3787 |
| | | 607/61 |
| 2011/0034912 A1 | 2/2011 | De Graff |
| 2011/0051384 A1 | 3/2011 | Kriechbaum |
| 2011/0054583 A1 | 3/2011 | Litt |
| 2011/0101789 A1 | 5/2011 | Salter |
| 2011/0121822 A1 | 5/2011 | Parsche |
| 2011/0140897 A1 | 6/2011 | Purks |
| 2011/0175735 A1 | 7/2011 | Forster |
| 2011/0184320 A1 | 7/2011 | Shipps |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0277813 A1 | 11/2011 | Rogers |
| 2011/0284268 A1 | 11/2011 | Palaniswamy |
| 2011/0306851 A1 | 12/2011 | Wang |
| 2012/0016258 A1 | 1/2012 | Webster |
| 2012/0051005 A1 | 3/2012 | Vanfleteren |
| 2012/0052268 A1 | 3/2012 | Axisa |
| 2012/0065937 A1* | 3/2012 | de Graff ............. G01D 9/005 |
| | | 702/187 |
| 2012/0074546 A1 | 3/2012 | Chong |
| 2012/0087216 A1 | 4/2012 | Keung |
| 2012/0091594 A1 | 4/2012 | Landesberger |
| 2012/0092178 A1 | 4/2012 | Callsen |
| 2012/0092222 A1 | 4/2012 | Kato |
| 2012/0101413 A1 | 4/2012 | Beetel |
| 2012/0101538 A1 | 4/2012 | Ballakur |
| 2012/0108012 A1 | 5/2012 | Yasuda |
| 2012/0126418 A1 | 5/2012 | Feng |
| 2012/0157804 A1 | 6/2012 | Rogers |
| 2012/0172697 A1 | 7/2012 | Urman |
| 2012/0178367 A1 | 7/2012 | Matsumoto |
| 2012/0226130 A1 | 9/2012 | De Graff |
| 2012/0244848 A1 | 9/2012 | Ghaffari |
| 2012/0256308 A1 | 10/2012 | Helin |
| 2012/0316455 A1 | 12/2012 | Rahman |
| 2012/0327608 A1 | 12/2012 | Rogers |
| 2013/0006064 A1* | 1/2013 | Reiner ............. A61B 5/4884 |
| | | 600/300 |
| 2013/0041235 A1 | 2/2013 | Rogers |
| 2013/0099358 A1 | 4/2013 | Elolampi |
| 2013/0100618 A1 | 4/2013 | Rogers |
| 2013/0118255 A1* | 5/2013 | Callsen ............. A42B 3/046 |
| | | 73/491 |
| 2013/0150693 A1 | 6/2013 | D'Angelo |
| 2013/0185003 A1 | 7/2013 | Carbeck |
| 2013/0192356 A1* | 8/2013 | De Graff ............. F41H 1/04 |
| | | 73/152.01 |
| 2013/0200268 A1 | 8/2013 | Rafferty |
| 2013/0211761 A1 | 8/2013 | Brandsma |
| 2013/0214300 A1 | 8/2013 | Lerman |
| 2013/0215467 A1 | 8/2013 | Fein |
| 2013/0225965 A1 | 8/2013 | Ghaffari |
| 2013/0237150 A1 | 9/2013 | Royston |
| 2013/0245388 A1 | 9/2013 | Rafferty |

(56) References Cited

U.S. PATENT DOCUMENTS

| | | | |
|---|---|---|---|
| 2013/0261415 A1 | 10/2013 | Ashe | |
| 2013/0261464 A1 | 10/2013 | Singh | |
| 2013/0274562 A1 | 10/2013 | Ghaffari | |
| 2013/0313713 A1 | 11/2013 | Arora | |
| 2013/0316442 A1 | 11/2013 | Meurville | |
| 2013/0316487 A1 | 11/2013 | De Graff | |
| 2013/0316645 A1 | 11/2013 | Li | |
| 2013/0320503 A1 | 12/2013 | Nuzzo | |
| 2013/0321373 A1 | 12/2013 | Yoshizumi | |
| 2013/0328219 A1 | 12/2013 | Chau | |
| 2014/0001058 A1 | 1/2014 | Ghaffari | |
| 2014/0012160 A1 | 1/2014 | Ghaffari | |
| 2014/0012242 A1 | 1/2014 | Lee | |
| 2014/0022746 A1 | 1/2014 | Hsu | |
| 2014/0039290 A1 | 2/2014 | De Graff | |
| 2014/0097944 A1 | 4/2014 | Fastert | |
| 2014/0110859 A1 | 4/2014 | Rafferty | |
| 2014/0140020 A1 | 5/2014 | Rogers | |
| 2014/0188426 A1* | 7/2014 | Fastert | G01P 15/0891 702/139 |
| 2014/0191236 A1 | 7/2014 | Nuzzo | |
| 2014/0216524 A1 | 8/2014 | Rogers | |
| 2014/0240932 A1 | 8/2014 | Hsu | |
| 2014/0249520 A1 | 9/2014 | Ghaffari | |
| 2014/0303452 A1 | 10/2014 | Ghaffari | |
| 2014/0340857 A1 | 11/2014 | Hsu | |
| 2014/0374872 A1 | 12/2014 | Rogers | |
| 2014/0375465 A1 | 12/2014 | Fenuccio | |
| 2015/0001462 A1 | 1/2015 | Rogers | |
| 2015/0019135 A1* | 1/2015 | Kacyvenski | A61B 5/0488 702/19 |
| 2015/0035680 A1 | 2/2015 | Li | |
| 2015/0069617 A1 | 3/2015 | Arora | |
| 2015/0099976 A1 | 4/2015 | Ghaffari | |
| 2015/0100135 A1 | 4/2015 | Ives | |
| 2015/0194817 A1 | 7/2015 | Lee | |
| 2015/0237711 A1 | 8/2015 | Rogers | |
| 2015/0241288 A1 | 8/2015 | Keen | |
| 2015/0260713 A1 | 9/2015 | Ghaffari | |
| 2015/0272652 A1 | 10/2015 | Ghaffari | |
| 2015/0286913 A1 | 10/2015 | Fastert | |
| 2015/0320472 A1 | 11/2015 | Ghaffari | |
| 2015/0335254 A1 | 11/2015 | Elolampi | |
| 2015/0342036 A1 | 11/2015 | Fastert | |
| 2016/0027834 A1 | 1/2016 | de Graff | |
| 2016/0045162 A1 | 2/2016 | De Graff | |
| 2016/0081192 A1 | 3/2016 | Hsu | |
| 2016/0086909 A1 | 3/2016 | Garlock | |
| 2016/0095652 A1 | 4/2016 | Lee | |
| 2016/0099214 A1 | 4/2016 | Dalal | |
| 2016/0099227 A1 | 4/2016 | Dalal | |
| 2016/0111353 A1 | 4/2016 | Rafferty | |
| 2016/0135740 A1 | 5/2016 | Ghaffari | |
| 2016/0166202 A1* | 6/2016 | Haraikawa | A61B 5/6805 600/389 |

FOREIGN PATENT DOCUMENTS

| | | |
|---|---|---|
| EP | 1808124 A2 | 7/2007 |
| EP | 2259062 A2 | 12/2010 |
| JP | 05-087511 A | 4/1993 |
| JP | 2009-170173 A | 7/2009 |
| JP | 2009-240730 A | 10/2009 |
| JP | 2012-135626 A | 7/2012 |
| JP | 2012-183177 A | 9/2012 |
| WO | WO 1999/038211 A2 | 7/1999 |
| WO | WO 2005/122285 A2 | 12/2005 |
| WO | WO 2003/021679 A2 | 3/2006 |
| WO | WO 2007003019 A2 | 1/2007 |
| WO | WO 2007/024983 A2 | 3/2007 |
| WO | WO 2007/116344 A1 | 10/2007 |
| WO | WO 2007/136726 A2 | 11/2007 |
| WO | WO 2008/030960 A2 | 3/2008 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |
| WO | WO 2015/080991 A1 | 6/2015 |
| WO | WO 2015/102951 A2 | 7/2015 |
| WO | WO 2015/103483 A1 | 7/2015 |
| WO | WO 2015/1033580 A2 | 7/2015 |
| WO | WO 2015/127458 A1 | 8/2015 |
| WO | WO 2015/134588 A1 | 9/2015 |
| WO | WO 2015/138712 A1 | 9/2015 |
| WO | WO 2016/048888 A1 | 3/2016 |
| WO | WO 2016/054512 A1 | 4/2016 |
| WO | WO 2016/057318 A1 | 4/2016 |
| WO | WO 2016/081244 A1 | 5/2016 |

OTHER PUBLICATIONS

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).

Ellerbee et al., "Quantifying Colorimetric Assays in Paper-Based Microfluidic Devices by Measuring the Transmission of Light through Paper," Analytical Chemistry, vol. 81, No. 20 8447-8452, (6 pages) (Oct. 15, 2009).

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

(56) References Cited

OTHER PUBLICATIONS

Kim et al., "Electrowetting on Paper for Electronic Paper Display," ACS Applied Materials & Interfaces, vol. 2, No. 11, (3318-3323) (6 pages) (Nov. 24, 2010).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Siegel et al., "Foldable Printed Circuit Boards on Paper Substrates," Advanced Functional Materials, vol. 20, No. 1, 28-35, (8 pages) (Jan. 8, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

Wikipedia, "Ball bonding" article [online]. Cited in PCT/US2015/051210 search report dated Mar. 1, 2016 with the following information "Jun. 15, 2011 [retrieved on Nov. 15, 2015}. Retrieved Dec. 29, 2018, from the Internet: <URL:https://web.archive.org/web/20110615221003/hltp://en.wikipedia.org/wiki/Ball_bonding>., entire document, especially para 1, 4, 5, 6," 2 pages, last page says ("last modified on May 11, 2011").

International Search Report PCT/US2014/059566, 5 pages (dated Feb. 17, 2015).

Written Opinion of the International Searching Authority PCT/US2014/059566, 5 pages (dated Feb. 17, 2015).

\* cited by examiner

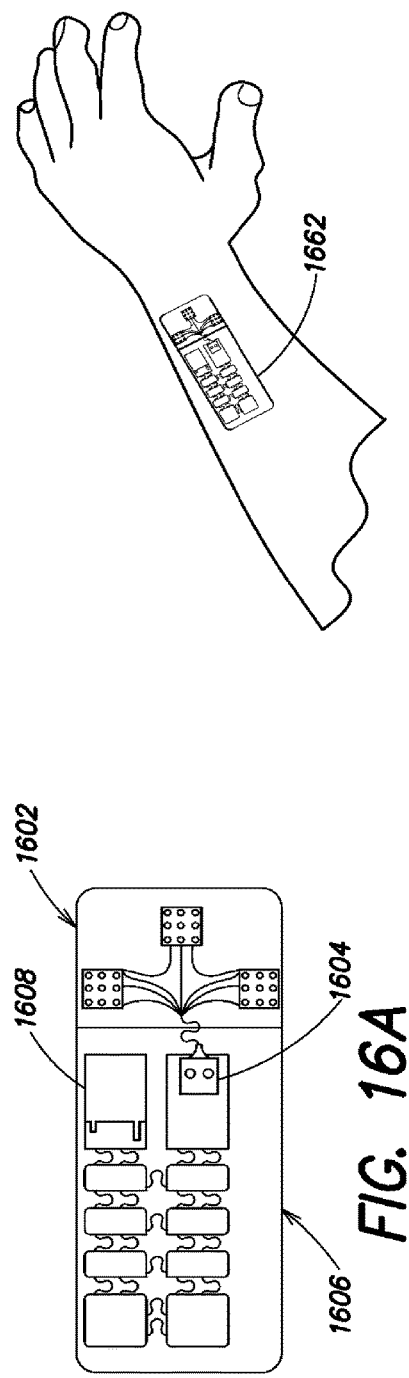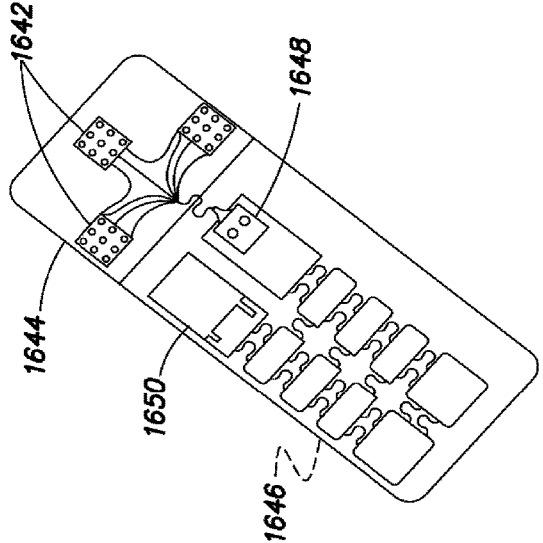
FIG. 16A  FIG. 16B  FIG. 16C

ON BODY

ON CHARGER

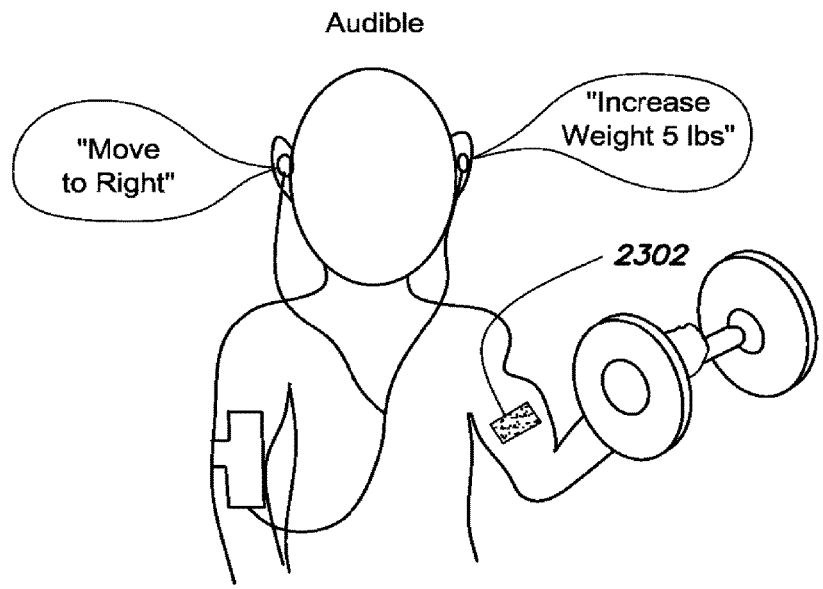
FIG. 23A
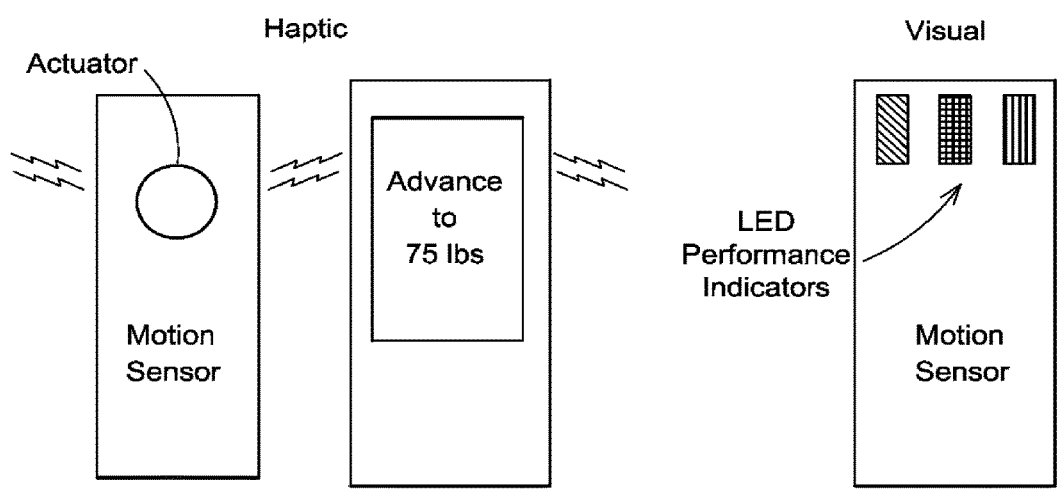
FIG. 23B
FIG. 23C

CONFORMAL SENSOR SYSTEMS FOR SENSING AND ANALYSIS

CROSS-REFERENCE TO RELATED PATENT APPLICATIONS

This application is a U.S. National Stage of International Application No. PCT/US2014/059566, filed Oct. 7, 2014, which claims the benefit of priority to U.S. Provisional Patent Application No. 61/887,696, which is entitled "Conformal Sensors and Analysis" and was filed on Oct. 7, 2013, U.S. Provisional Patent Application No. 61/902,151, which is entitled "Conformal Sensor Systems for Sensing and Analysis" and was filed on Nov. 8, 2013, U.S. Provisional Patent Application No. 62/002,773, which is entitled "Throw Monitoring and Analysis" and was filed on May 23, 2014, and U.S. Provisional Patent Application No. 62/058,318, which is entitled "Conformal Sensors and Methods for Using the Same " and was filed on Oct. 1, 2014, all of which are incorporated herein by reference in their respective entireties.

BACKGROUND

Existing technology for monitoring movement, including a throwing motion, may require either an expensive 3-D motion capture/video analysis system, or for an athlete to wear bulky devices in a laboratory that can impede on performance. Some of the bulkier systems can be external (video capture) devices. This technology is not suitable for real-time or on-field monitoring. In addition, existing methods for counting throws or pitches are manual, e.g., clickers, and can require close monitoring by a coaching staff. Due to the restrictive nature of placing rigid electronics on a throwing arm, there do not appear to be any throwing-specific products on the market.

SUMMARY

Systems, apparatus and methods are provided for monitoring the performance of an individual using a conformal sensor device. In some implementations, the system can be disposed into conformal electronics that can be coupled to or disposed on a portion of the individual. The system can include a storage module to allow for data to be reviewed and analyzed. In some implementations, the system can also include an indicator. In some implementations, the indicator can be used to display real time analysis of impacts made by the system.

The example systems, methods, and apparatus according to the principles described herein provide better performance than large and bulky devices for looking at body motion.

In an example, the portion of the individual can be a head, a foot, a chest, an abdomen, a shoulder, a torso, a thigh, or an arm.

Conformal sensor devices for analyzing at least a portion of a user are disclosed. In some embodiments, the conformal sensor device includes at least one flexible substrate that is operable to attach (e.g., via adhesives) to the user (e.g., directly onto the user's skin). At least one power supply is embedded on or within the at least one flexible substrate and is operable to power the conformal sensor device. In addition, at least one memory device is embedded on or within the at least one flexible substrate. The at least one memory device stores microprocessor executable instructions. At least one microprocessor, which is also embedded on or within the at least one flexible substrate, is communicatively coupled to the at least one memory device and operable to execute the microprocessor executable instructions. Moreover, at least one sensor device is embedded on or within the at least one flexible substrate and is operable to obtain at least one measurement of the user. Additionally, at least one wireless communication component is embedded on or within the at least one flexible substrate and is operable to transmit data indicative of the at least one measurement obtained by the at least one sensor.

Also disclosed herein are conformal sensor assemblies for analyzing an individual. In some embodiments, the conformal sensor assembly includes a flexible substrate that is operable to attach or couple to a portion of the individual. A power supply and a microprocessor are attached or coupled to the flexible substrate. The microprocessor is operable to execute microprocessor executable instructions. In addition, a sensor device is attached or coupled to the flexible substrate and is operable to obtain at least one measurement of the user.

Representative conformal sensor systems for monitoring a user are also disclosed herein. In some embodiments, the conformal sensor system includes at least one memory device that stores microprocessor executable instructions. At least one microprocessor is (electrically and/or communicatively) coupled to the at least one memory device and is operable to execute the microprocessor executable instructions. The conformal sensor system also includes at least one sensor device, at least one wireless communication component, and at least one power supply. The at least one sensor device is (electrically and/or communicatively) coupled to the at least one microprocessor and is operable to obtain at least one measurement of the user. The at least one wireless communication component is (electrically and/or communicatively) coupled to the at least one microprocessor and is operable to transmit data indicative of the at least one measurement obtained by the at least one sensor. In addition, the at least one power supply is (electrically and/or communicatively) coupled to and operable to power the at least one memory device, microprocessor, sensor device and wireless communication component.

An example system for monitoring performance of an individual using a conformal sensor device is disclosed. The conformal sensor device mounted to a first portion of the individual. The example system includes at least one memory for storing processor executable instructions, a processing unit for accessing the at least one memory and executing the processor executable instructions, and an analyzer. The processor executable instructions include a communication module to receive data indicative of at least one measurement of at least one sensor component of a first conformal sensor device. The first conformal sensor device includes at least one sensor component. The at least one sensor component is configured to obtain at least one measurement of at least one of: (a) acceleration data representative of an acceleration proximate to the portion of the individual, and (b) force data representative of a force applied to the individual. The first conformal sensor device substantially conforms to a surface of the first portion of the individual to provide a degree of conformal contact, and the data indicative of the at least one measurement includes data indicative of the degree of the conformal contact. The analyzer is configured to quantify a parameter indicative of at least one of (i) an imparted energy and (ii) a head-injury-criterion (HIC), based on the at least one measurement of the at least one sensor component and the degree of the conformal contact. A comparison of the parameter to a preset performance threshold value provides an indication of the performance of the individual.

In an example, the first portion of the individual is at least one of a calf, a knee, a thigh, a head, a foot, a chest, an abdomen, a shoulder, and an arm. The at least one sensor component can be an accelerometer or a gyroscope. The at least one sensor component can be configured to further obtain at least one measurement of physiological data for the individual.

In an example, the preset performance threshold value is determined using data indicative of a prior performance of the individual and/or data indicative of a prior performance of a plurality of different individuals. In an example, the analyzer determines a period of time that the individual performs reduced physical activity if the indication of the performance of the individual is below the preset performance threshold value.

In another example, the preset performance threshold value is determined using at least one measurement from a second sensor component that substantially conforms to a surface of a second portion of the individual.

The first conformal sensor device can further include a flexible and/or stretchable substrate, where the at least one sensor component is disposed on the flexible and/or stretchable substrate, and where the at least one sensor component is coupled to at least one stretchable interconnect. The flexible and/or stretchable substrate can include a fabric, an elastomer, paper, or a piece of equipment. The at least one stretchable interconnect can be electrically conductive or non-conductive.

The example system can include at least one indicator to display the indication of the performance of the individual. The at least one indicator can be a liquid crystal display, an electrophoretic display, or an indicator light.

In an example, the at least one indicator is an indicator light, and where the indicator light appears different if the indication of the performance of the individual is below the preset performance threshold value than if the indication of the performance of the individual meets or exceeds the preset performance threshold value. The appearance of the indicator light may be detectable by the human eye or by an image sensor of a smartphone, a tablet computer, a slate computer, an electronic gaming system, and/or an electronic reader.

In an example, the first conformal sensor device can include at least one stretchable interconnect to electrically couple the at least one sensor component to at least one other component of the first conformal sensor device. The at least one other component can be at least one of: a battery, a transmitter, a transceiver, an amplifier, a processing unit, a charger regulator for a battery, a radio-frequency component, a memory, and an analog sensing block.

The example communication module can include a near-field communication (NFC)-enabled component to receive the data indicative of the at least one measurement.

In an example, a communication module can be configured to implement a communication protocol based on Bluetooth® technology, Wi-Fi, Wi-Max, IEEE 802.11 technology, a radio frequency (RF) communication, an infrared data association (IrDA) compatible protocol, or a shared wireless access protocol (SWAP).

The example system can further include at least one memory to store the data indicative of the at least one measurement and/or the parameter.

In another aspect, an example system is disclosed for assessing the performance of an individual using conformal sensor devices. The example system can include a data receiver to receive data indicative of measurements of at least one of a first conformal sensor device and a second conformal sensor device, each of the first conformal sensor device and the second conformal sensor device being disposed at and substantially conforming to a respective portion of the individual. Each of the first and conformal sensor devices can include at least one sensor component to obtain at least one measurement. The at least one measurement can be of at least one of: (a) acceleration data representative of an acceleration proximate to the portion of the individual, and (b) force data representative of a force applied to the individual. The data indicative of the at least one measurement includes data indicative of a degree of a conformal contact between the respective conformal sensor device and the respective portion of the individual. The example system also includes an analyzer to quantify a parameter indicative of at least one of (i) an imparted energy and (ii) a head-injury-criterion (HIC), based on the at least one measurement from each of the first conformal sensor device and the second conformal sensor device. A comparison of the parameter determined based on the at least one measurement from the first conformal sensor device to the parameter determined based on the at least one measurement from the second conformal sensor device provides an indication of the performance of the individual.

In an example, each of the first conformal sensor device and the second conformal sensor device can be disposed at and substantially conforming to each calf, each knee, each thigh, each foot, each hip, each arm, or each shoulder of the individual.

The at least one sensor component can be an accelerometer or a gyroscope.

In an example, the individual may be classified as exhibiting reduced performance if the parameter determined based on the at least one measurement from the first conformal sensor device is different from the parameter determined based on the at least one measurement from the second conformal sensor device.

In this example, the analyzer may further be configured to determine a period of time that the individual performs reduced physical activity if the individual is classified as exhibiting reduced performance.

In an example, at least one of the first conformal sensor device and the second conformal sensor device can further include a flexible and/or stretchable substrate, where the at least one sensor component is disposed on the flexible and/or stretchable substrate, and where the at least one sensor component is coupled to at least one stretchable interconnect.

In an example, the at least one stretchable interconnect can be electrically conductive or non-conductive.

The data receiver of the example system may further include a near-field communication (NFC)-enabled component.

In an example, the data receiver can be configured to implement a communication protocol based on Bluetooth® technology, Wi-Fi, Wi-Max, IEEE 802.11 technology, a radio frequency (RF) communication, an infrared data association (IrDA) compatible protocol, or a shared wireless access protocol (SWAP).

In an example, the system can further include at least one memory to store the parameter and/or the data indicative of the measurements of at least one of the first conformal sensor device and the second conformal sensor device.

In another aspect, an example system is disclosed for monitoring performance of an individual using a conformal sensor device mounted to a portion of an arm of the individual. The example system includes at least one memory for storing processor executable instructions, a processing unit for accessing the at least one memory and executing the processor executable instructions, and an analyzer. The processor executable instructions include a communication module to receive data indicative of at least one measurement of at least one sensor component of a conformal sensor device. The conformal sensor device includes at least one sensor component to obtain at least one measurement of data representative of an acceleration of the portion of the arm. The conformal sensor device substantially conforms to a surface of the portion of the arm to provide a degree of conformal contact. The data indicative of the at least one measurement includes data indicative of the degree of the conformal contact. The analyzer is configured to quantify a parameter indicative of an energy or the acceleration of the portion of the arm, based on the at least one measurement of the at least one sensor component and the degree of the conformal contact. A comparison of the parameter to a preset performance threshold value provides an indication of the performance of the individual.

The at least one sensor component can be an accelerometer or a gyroscope.

In an example, the at least one sensor component furthers obtain at least one measurement of physiological data for the individual.

In an example, the analyzer determines a period of time that the individual performs reduced physical activity if the indication of the performance of the individual is below the preset performance threshold value.

The example system can further include a storage device coupled to the communication module, where the storage device is configured to store data indicative of a count of a number of times that the indication of the performance of the individual exceeds the predetermined threshold value of imparted energy.

In an example, the system further includes a transmission module to transmit the data indicative of a count of a number of times that the indication of the performance of the individual exceeds the predetermined threshold value of imparted energy.

The transmission module can be a wireless transmission module.

In an example, the sensor component can further include at least one of an accelerometer and a gyroscope, and where the parameter indicative of the energy or the acceleration of the portion of the arm is computed based on the at least one measurement from the accelerometer and/or the gyroscope.

In an example, the system can be configured such that the processor executes processor executable instructions to compare the parameter to a preset performance threshold value, thereby determining the indication of the performance of the individual.

In an example, the system can be configured such that the processor executes processor-executable instructions to increment a first cumulative number of counts for each comparison wherein the parameter exceeds the preset performance threshold value.

In another aspect, an example system is disclosed for monitoring performance of an individual using a conformal sensor device mounted to a first portion of the individual. The example system includes at least one memory for storing processor executable instructions, a processing unit for accessing the at least one memory and executing the processor executable instructions, and an analyzer. The processor executable instructions include a communication module to receive data indicative of at least one measurement of at least one sensor component of a first conformal sensor device. The first conformal sensor device includes at least one sensor component to obtain at least one measurement of at least one of: (a) acceleration data representative of an acceleration proximate to the portion of the individual, and (b) physiological data representative of a physiological condition of the individual. The first conformal sensor device substantially conforms to a surface of the first portion of the individual to provide a degree of conformal contact. The data indicative of the at least one measurement includes data indicative of the degree of the conformal contact. The analyzer can be configured to quantify, based on the at least one measurement of the at least one sensor component and the degree of the conformal contact, a performance parameter indicative of at least one of: a throw count, a pattern matching, a symmetry, a movement magnitude, a grip intensity, a kinetic link, and a readiness to return to play. A comparison of the parameter to a preset performance threshold value provides an indication of the performance of the individual.

In an example, the first portion of the individual is at least one of a calf, a knee, a thigh, a head, a foot, a chest, an abdomen, a shoulder, and an arm.

The at least one sensor component can be an accelerometer or a gyroscope.

In an example, the system can be configured such that the at least one sensor component furthers obtain at least one measurement of physiological data for the individual.

The first conformal sensor device can further include at least one communication interface to transmit the data indicative of the at least one measurement and/or the indication of the performance of the individual.

In an example, the preset performance threshold value is determined using data indicative of a prior performance of the individual and/or data indicative of a prior performance of a plurality of different individuals.

In another example, the preset performance threshold value is determined using at least one measurement from a second sensor component that substantially conforms to a surface of a second portion of the individual.

In an example, the first conformal sensor device can further include a flexible and/or stretchable substrate, where the at least one sensor component is disposed on the flexible and/or stretchable substrate, and where the at least one sensor component is coupled to at least one stretchable interconnect.

The flexible and/or stretchable substrate can include a fabric, an elastomer, paper, or a piece of equipment.

The at least one stretchable interconnect can be electrically conductive or non-conductive.

In an example, the first conformal sensor device can further include at least one stretchable interconnect to electrically couple the at least one sensor component to at least one other component of the first conformal sensor device. The at least one other component can be at least one of: a battery, a transmitter, a transceiver, an amplifier, a processing unit, a charger regulator for a battery, a radio-frequency component, a memory, and an analog sensing block.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system, apparatus and method may be better understood from the following illustrative description with reference to the following drawings in which:

FIGS. 16A and 16B show example implementations of a conformal sensor system, according to the principles herein.

FIG. 16C shows an example implementation of a conformal sensor device coupled to a body part with a degree of conformal contact, according to the principles herein.

FIGS. 23A, 23B and 23C show an example of use of the example conformal sensor systems for quantifying a measure of performance for user feedback, according to the principles herein.

DETAILED DESCRIPTION

Figure 1A:
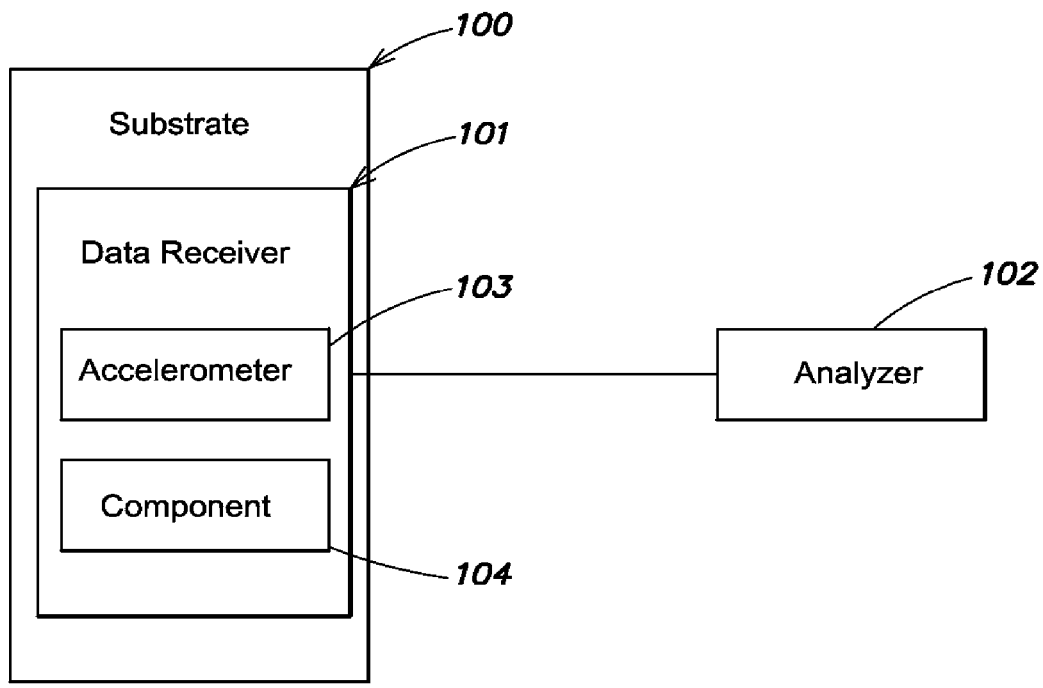
FIGS. 1A-1D show block diagrams of example devices for monitoring the performance of an individual, according to the principles herein.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems for quantifying the performance of an individual using measurement data obtained using a conformal sensor device. According to a non-limiting example, the performance of the individual may be quantified using a parameter referred to as a "throw count," which serves as a measure of a performance of the individual in a throwing motion and/or a hitting (including licking) an object. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, the term "including" means including but not limited to. The term "based on" means based at least in part on.

Example systems, methods and apparatus are described for quantifying the performance of an individual using a conformal sensor device mounted to a portion of the individual. The conformal sensor device is configured to substantially conform to the portion of the individual according to a degree of conformal contact. An example system includes at least one memory for storing processor executable instructions and a processing unit for accessing the at least one memory and executing the processor executable instructions. The processor executable instructions include a communication module to receive data indicative of measurements of a sensor component of the conformal sensor device. The sensor component can be configured to measure acceleration data representative of an acceleration proximate to the portion of the individual, and/or force data representative of a force applied to the individual. The measurement data includes data indicative of the degree of the conformal contact. The processor executable instructions also include an analyzer to quantify a parameter indicative of at least one of (i) an imparted energy and (ii) a head-injury-criterion (HIC), based at least in part on the sensor component measurement and data indicative of the degree of the conformal contact. A comparison of the parameter to a preset performance threshold value provides an indication of the performance of the individual.

In a non-limiting example, the preset performance threshold value can be determined based on measurements data from a conformal sensor component disposed on a different portion of the individual. For example, the preset performance threshold value can be determined based on measurements from a conformal sensor component disposed on a second arm to compare to measurements from a first arm, disposed proximate to a second knee to compare to measurements from a first knee, disposed on a second leg to compare to measurements from a first leg, or disposed on a second shoulder to compare to measurements from a first shoulder. In a non-limiting example, the preset performance threshold value can be determined based on measurements from a plurality of other individuals.

The data imparted energy can be computed as an area under a curve from acceleration measurement data or force measurement data, such as but not limited to a force versus distance curve. The head-injury-criterion (HIC) can be used to provide a measure of the likelihood that an impact results in a head injury. As a non-limiting example, the head-injury-criterion (HIC) can be computed using the expression:

$$HIC = \left\{ \left[ \frac{1}{t_2 - t_1} \int_{t_1}^{t_2} \alpha(t) \, dt \right]^{2.5} (t_2 - t_1) \right\}_{max}$$

where $t_1$ and $t_2$ indicate the time interval (in seconds) during which the HIC approaches a maximum value, and a(t) is acceleration. The time interval can be restricted to a specific value, such as but not limited to between about 3 milliseconds and 36 milliseconds.

In various examples described herein, the individual's performance can be quantified based on the measurement data such as, but not limited to, peak acceleration data and/or force data. In some examples, the imparted energy can be computed based on the integral of a time variation of a liner and/or acceleration in motion of the body part. Accordingly, the imparted energy calculation can take into account the magnitude and duration of motion of the body part.

According to the principles described herein, the measurement data and/or the indication of the performance of the individual may be displayed using a display or other indicator of the system, stored to a memory of the system, and/or transmitted to an external computing device and/or the cloud. In an example, the system may include a data receiver that is configured to receive data transmitted by the sensor component to provide the measurement data. In example, the data receiver can be a component of a device that is integral with the conformal sensor device.

In an example, the system can include at least one indicator to display the indication of the performance of the individual. The indicator may be a liquid crystal display, an electrophoretic display, or an indicator light. The example system can be configured such that indicator light appears different if the indication of the performance of the individual is below the preset performance threshold value than if the indication of the performance of the individual meets or exceeds the preset performance threshold value. The example system can be configured such that the appearance of the indicator light is detectable by the human eye or outside the detectable range of the human eye but detectable by use of an image sensor of computing device. Non-limiting examples of a computing device applicable to any of the example systems, apparatus or methods according to the principles herein include a smartphone (such as but not limited to an Iphone®, an Android™ phone, or a Blackberry®), a tablet computer, a laptop, a slate computer, an electronic gaming system (such as but not limited to an XBOX®, a Playstation®, or a Wii®), an electronic reader (an e-reader), and/or other electronic reader or hand-held or wearable computing device.

An example system, apparatus and method according to the principles herein provide a device for monitoring the performance of the individual as a cumulative throw count of throws (including hits or kicks) that have above a value of imparted energy above a predetermined threshold value of imparted energy.

For any of the example systems, methods, and apparatus herein, the conformal sensor device may be disposed on or otherwise coupled to a body part of the individual. In various example implementations, at least one conformal sensor device can be disposed on or otherwise coupled to a portion of a calf, a knee, a thigh, a head, a foot, the chest, the abdomen, the shoulder, and/or an arm of the individual. The individual may be a human subject or a non-human animal (such as but not limited to a dog, a horse, or a camel). In a non-human animal, the conformal sensor device may be disposed on or otherwise coupled to the haunch.

An example system, apparatus and method according to the principles herein provide a device for monitoring the performance of an individual using at least two conformal sensor devices, each mounted to different portions of the individual. Each conformal sensor device is configured to substantially conform to the respective portion of the individual according to a respective degree of conformal contact. An example system includes at least one memory for storing processor executable instructions and a processing unit for accessing the at least one memory and executing the processor executable instructions. The processor executable instructions include a communication module to receive data indicative of measurements of a sensor component of each of the conformal sensor devices. Each sensor component can be configured to measure acceleration data representative of an acceleration proximate to the portion of the individual, and/or force data representative of a force applied to the individual. The measurement data includes data indicative of the degree of the conformal contact. The processor executable instructions also include an analyzer to quantify a parameter indicative of at least one of (i) an imparted energy and (ii) a head-injury-criterion (HIC), based on the measurement from each of the conformal sensor devices. A comparison of the parameter determined based on the measurements from each of the conformal sensor devices provides an indication of the performance of the individual.

As a non-limiting example, each of the conformal sensor devices can be disposed at and substantially conforming to each calf, each knee, each thigh, each foot, each hip, each arm, or each shoulder of the individual. In such an example, the comparison can be used to provide an indication of the symmetry of the individual prior to, during, and/or after rehabilitation or physical therapy.

In addition to specific high-energy impact events to the body, the example the systems, methods, and apparatus described herein use an analysis of data indicative of body motion, as non-limiting examples, for such applications as training and/or clinical purposes.

Data gathered based on sensing the motion of the body or part of the body, along with data gathered based on sensing other physiological measures of the body, can be analyzed to provide useful information related to range of motion, types of motion, and changes in the motion. When this sensing is performed using thin, conformal, and wearable sensors and measurement devices including such sensors, these measures and metrics can be unimpeded by the size, weight or placement of the measurement devices.

Example systems, methods, and apparatus according to the principles described herein provide a thin and conformal electronic measurement system capable of measuring body motion or body part for a variety of applications, including rehabilitation, physical therapy, athletic training, and athlete monitoring. Additionally, the example systems, methods, and apparatus can be used for athlete assessment, performance monitoring, training, and performance improvement.

An example device for motion detection can include an accelerometer (such as but not limited to a 3-axis accelerometer. The example device may include a 3-axis gyroscope. The example device can be disposed on a body part, and data collected based on the motion of the body part is analyzed, and the energy under the motion vs. time curve can be determined as an indicator of energy or impulse of a motion.

The conformal sensor device combines motion sensing in the form of a 3D accelerometer and/or a 3-axis gyro to provide motion paths for a variety of applications. As a non-limiting example, the form of the devices can be either small surface-mount technology packages or unpackaged devices combined to form a very thin patch-based system. As a non-limiting example, the patch can be about 2 mm or less in thickness. The example patch can be attached adhesively to the body part similar to that of a band-aid or other bandage.

As a non-limiting example, the device architecture can include one or more sensors, power & power circuitry, wireless communication, and a microprocessor. These example devices can implement a variety of techniques to thin, embed and interconnect these die or package-based components.

FIGS. 1A-1D show non-limiting examples of possible device configurations. The example device of FIG. 1A includes a data receiver 101 disposed on a substrate 100. The data receiver 101 can be configured to conform to a portion of the object to which it and the substrate are coupled. The data receiver 101 can include one or more of any sensor component according to the principles of any of the examples and/or figures described herein. In this example, data receiver 101 includes at least one accelerometer 103 (such as but not limited to a triaxial accelerometer) and at least one other component 104. As a non-limiting example, the at least one other component 104 can be a gyroscope, hydration sensor, temperature sensor, an electromyography (EMG) component, a battery (including a rechargeable battery, a transmitter, a transceiver, an amplifier, a processing unit, a charger regulator for a battery, a radio-frequency component, a memory, and an analog sensing block, electrodes, a flash memory, a communication component (such as but not limited to Bluetooth® Low-Energy radio) and/or other sensor component.

The at least one accelerometer 103 can be used to measure data indicative of a motion of a portion of the individual. The example device of FIG. 1A also includes an analyzer 102. The analyzer 102 can be configured to quantify the data indicative of motion and/or physiological data, or analysis of such data indicative of motion and/or physiological data according to the principles described herein. In one example, the analyzer 102 can be disposed on the substrate 100 with the data receiver 101, and in another example, the analyzer 102 is disposed proximate to the substrate 100 and data receiver 101.

In the example implementation of the device in FIG. 1A, the analyzer 102 can be configured to quantify the data indicative of the motion by calculating an energy imparted and/or HIC value for the motion.

Figure 1B:
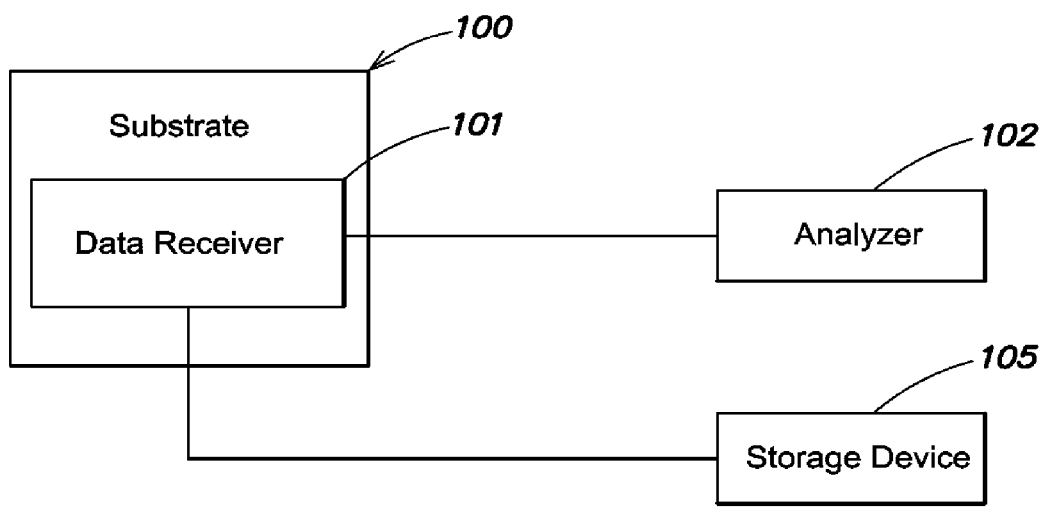

FIG. 1B shows another example device according to the principles disclosed herein that includes a substrate 100, data receiver 101, an analyzer 102, and a storage module 107. The storage module 107 can be configured to save data from the data receiver 101 and/or the analyzer 102. In some implementations the storage device 107 is any type of non-volatile memory. For example, the storage device 107 can include flash memory, solid state drives, removable memory cards, or any combination thereof. In certain examples, the storage device 107 is removable from the device. In some implementations, the storage device 107 is local to the device while in other examples it is remote. For example, the storage device 107 can be internal memory of a smartphone. In this example, the device may communicate with the phone via an application executing on the smartphone. In some implementations, the sensor data can be stored on the storage device 107 for processing at a later time. In some examples, the storage device 107 can include space to store processor-executable instructions that are executed to analyze the data from the data receiver 101. In other examples, the memory of the storage device 107 can be used to store the measured data indicative of motion and/or physiological data, or analysis of such data indicative of motion and/or physiological data according to the principles described herein.

Figure 1C:
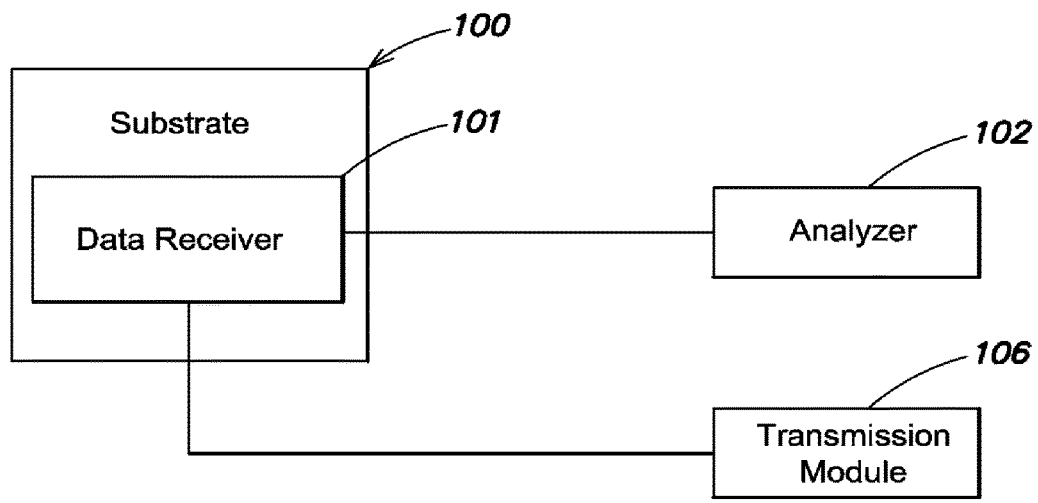

FIG. 1C shows an example device according to the principles disclosed herein that includes a substrate 100, a data receiver 101, an analyzer 102, and a transmission module 106. The transmission module 106 can be configured to transmit data from the data receiver 101, the analyzer 102, or stored in the storage device 107 to an external device. In one example, the transmission module 106 can be a wireless transmission module. For example, the transmission module 106 can transmit data to an external device via wireless networks, radio frequency communication protocols, Bluetooth, near-field communication, and/or optically using infrared or non-infrared LEDs.

Figure 1D:
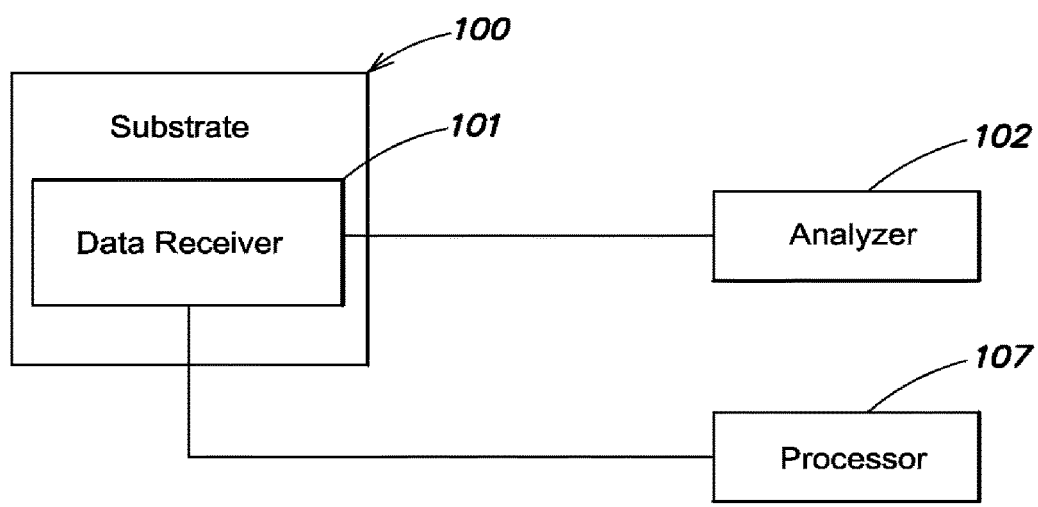

FIG. 1D shows an example system that includes a substrate 100, a data receiver 101, an analyzer 102 and a processor 107. The data receiver 101 can receive data related to sensor measurement from a conformal sensor device. In an example, the conformal sensor device can be a flexible sensor. The processor 107 can be configured to execute processor-executable instructions stored in a storage device 107 and/or within the processor 107 to analyze data indicative of motion and/or physiological data, or analysis of such data indicative of motion and/or physiological data according to the principles described herein. In some implementations, the data can be directly received from the data receiver 101 or retrieved from the storage device 107. In one example, the processor can be a component of the analyzer 102 and/or disposed proximate to the data receiver 101. In another example, the processor 107 can be external to the device, such as in an external device that downloads and analyzes data retrieved from the device. The processor 107 can execute processor-executable instructions that quantify the data received by the data receiver 101 in terms of imparted energy.

In another example, the processor 107 can categorize the quantitative measure of the performance of the individual relative to at least one predetermined threshold. For example, the device may indicate that a football or baseball player is to be benched or a worker may not report back to work if the analyzed data does not meet a performance threshold value. In another example, multiple differing predetermined thresholds may be used to monitor the performance level of an individual. In some examples, the processor 107 can maintain counts for each of the bins created by the differing predetermined thresholds and increment the counts when the quantitative measure of the performance of the individual corresponds to a specific bin. In some examples, the processor 107 can maintain counts for each of the bins created by the predetermined threshold and increment the counts when a performance metric is registered that corresponds to a specific bin. The processor 107 may transmit the cumulative counts for each bin to an external device via the transmission module 106. Non-limiting example categories include satisfactory, in need of further training, needing to be benched for the remained of the game, unsatisfactory, or any other type of classification.

Figure 2A:
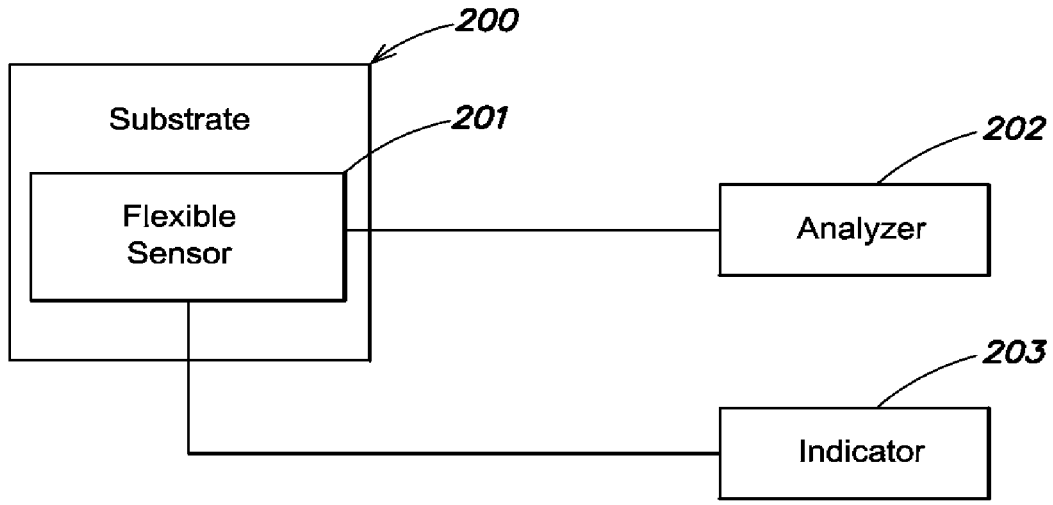
FIGS. 2A-2C show block diagrams of example devices for monitoring the performance of an individual and displaying data indicative of the performance metric, according to the principles herein.
Figure 2B:
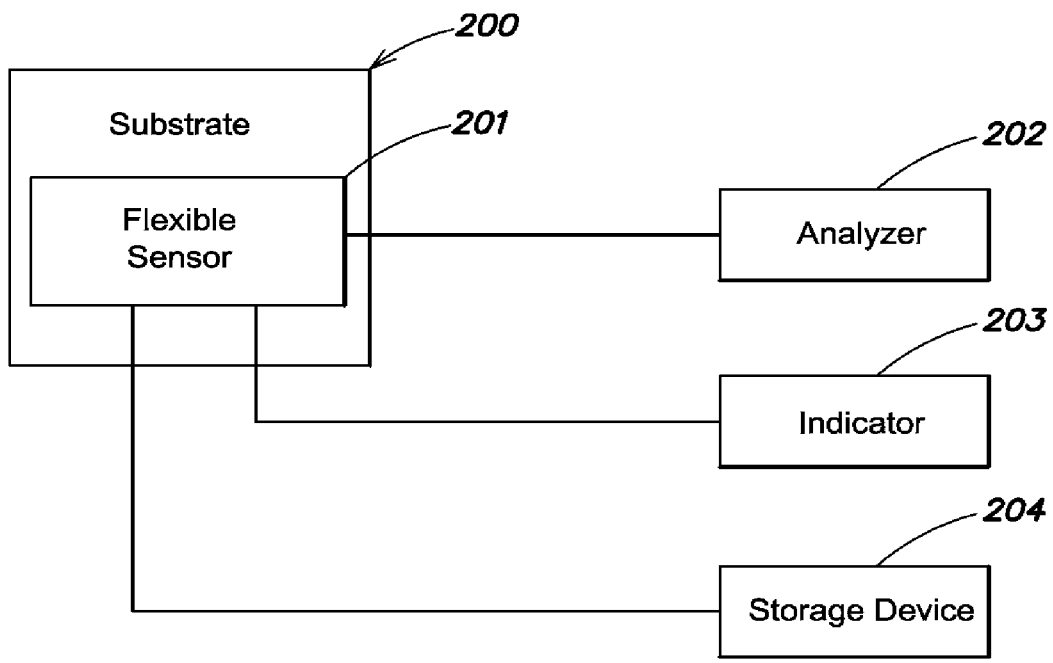
Figure 2C:
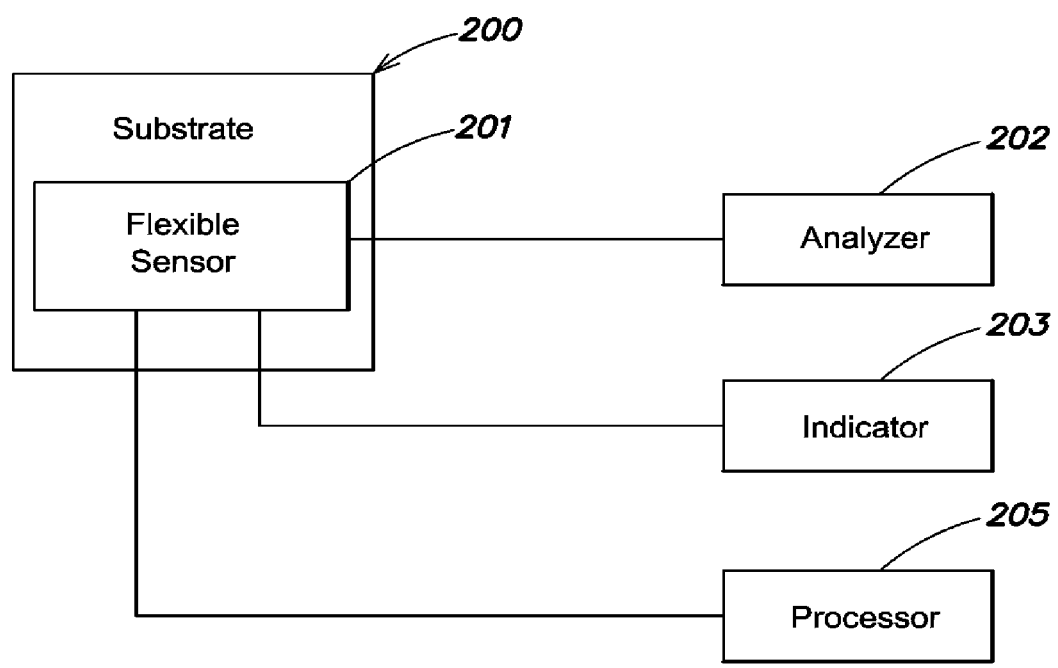

FIGS. 2A-2C show non-limiting examples of possible device configurations including a display for displaying the data or analysis results. The examples of FIGS. 2A-2C include a substrate 200, a flexible sensor 201, a analyzer 202, and an indicator 203. In different examples the device can include a processor 205, to execute the processor-executable instructions described herein; and a storage device 204 for storing processor-executable instructions and/or data from the analyzer 202 and/or flexible sensor 201. The example devices of FIGS. 2A-2C also include an indicator 203 for displaying and/or transmit data indicative of motion, physiological data, or analysis of such data indicative of motion, physiological data according to the principles described herein, and/or user information.

In one example, the indicator 203 can include a liquid crystal display, or an electrophoretic display (such as e-ink), and/or a plurality of indicator lights. For example, the indicator 203 can include a series of LEDs. In some implementations, the LEDs range in color, such as from green to red. In this example, if performance does not meet a predetermined threshold measure, a red indicator light can be activated and if the performance meets the pre-determined threshold measure, the green indicator light can be activated. In yet another example, the intensity of the LED indicator lights can be correlated to the magnitude of the quantified measure of performance of the individual or the bin counts (e.g., as a measure of throw count). For example, the LEDs can glow with a low intensity for quantified performance below a threshold and with a high intensity for quantified performance above the threshold.

In another example, the LEDs of the indicator 203 may be configured to blink at a specific rate to indicate the level of the quantified performance of the individual. For example, the indicator may blink slowly for a quantified performance over a first threshold but below a second threshold and blink at a fast rate for a quantified performance above the second threshold. In yet another example, the indicator 203 may blink using a signaling code, such as but not limited to Morse code, to transmit the measurement data and/or data indicative of performance level. In some implementations, as described above, the signaling of the indicator 203 is detectable to the human eye and in other implementations it is not detectable by the human eye and can only be detected by an image sensor. The indicator 203 emitting light outside the viable spectrum of the human eye (e.g. infrared) or too dim to be detected are examples of indication methods indictable to the human eye. In some examples, the image sensor used to detect the signals outside the viewing capabilities of a human eye can be the image sensor of a computing device, such as but not limited to a smartphone, a tablet computer, a slate computer, a gaming system, and/or an electronic reader.

Figure 3:
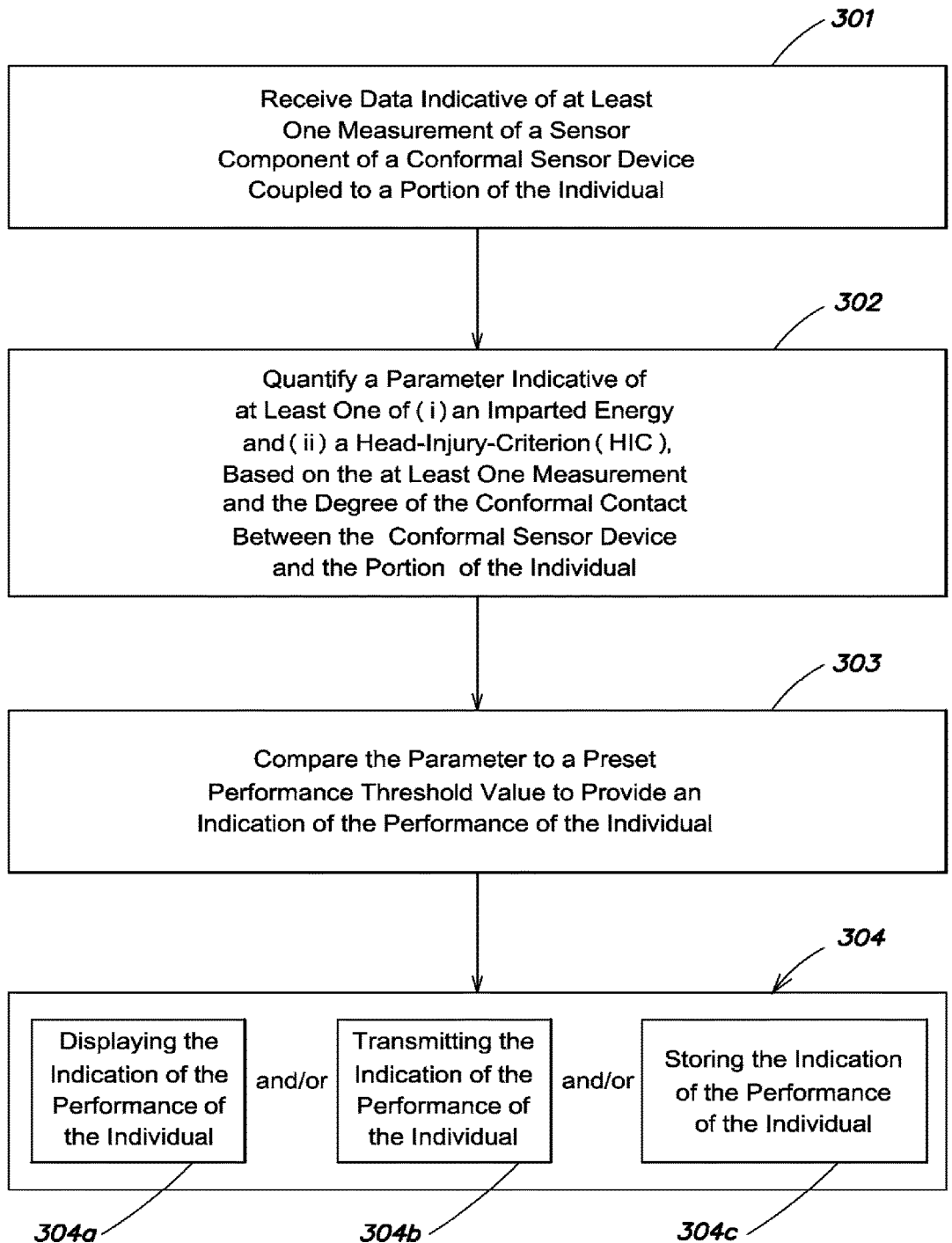
FIG. 3 shows a flow chart of an example method for monitoring the performance of an individual, according to the principles herein.

FIG. 3 show a flow chart illustrating a non-limiting example method of quantifying the performance of an individual, according to the principles described herein.

In block 301, a processing unit receives data indicative of at least one measurement of a sensor component of a conformal sensor device coupled to a portion of the individual. In an example, the at least one measurement can be acceleration data representative of an acceleration proximate to the portion of the individual and/or force data representative of a force applied to the individual.

The conformal sensor device is configured to substantially conform to the surface of the portion of the individual to provide a degree of conformal contact. The data indicative of the at least one measurement can include data indicative of the degree of the conformal contact.

In block 302, the processing unit quantifies a parameter indicative of at least one of (i) an imparted energy and (ii) a head-injury-criterion (HIC), based on the at least one measurement and the degree of the conformal contact between the conformal sensor device and the portion of the individual. In some examples, the processing unit may only quantify performance levels that have a value of imparted energy above a predetermined threshold value. As described above, in some examples, quantified performance corresponding to an imparted energy value above a first predetermined threshold may be further categorized responsive to if the imparted energy value corresponds to a performance level that exceeds a second or third predetermined threshold.

In block 303, the processing unit compares the parameter to a preset performance threshold value to provide an indication of the performance of the individual.

In block 304, the device displays, transmits, and/or or stores an indication of the indication of the performance of the individual. As indicated in FIG. 3, each of 304a, 304b, and 304c can be performed alone or in any combination. In one example, the indicator 203 can be used to display the indication of the performance of the individual to a user or to external monitor. For example, the device may include a display that displays a graph of performance data over time to a user. In another example, the transmitter 106 can be used to transmit, wirelessly or wired, the data indicative of the performance of the individual. In such an example, the data can be downloaded from the device and analyzed by implementing processor-executable instructions (e.g., via a computer application). In yet another example, the indication of the performance of the individual can be stored either locally to the device or on a separate device, such as but not limited to the hard-drive of a laptop.

While the description herein refers to three different predetermined thresholds, it is understood that the system can be configured to assess performance levels based on many more specified threshold levels according to the principles of the examples described herein.

Figure 4:
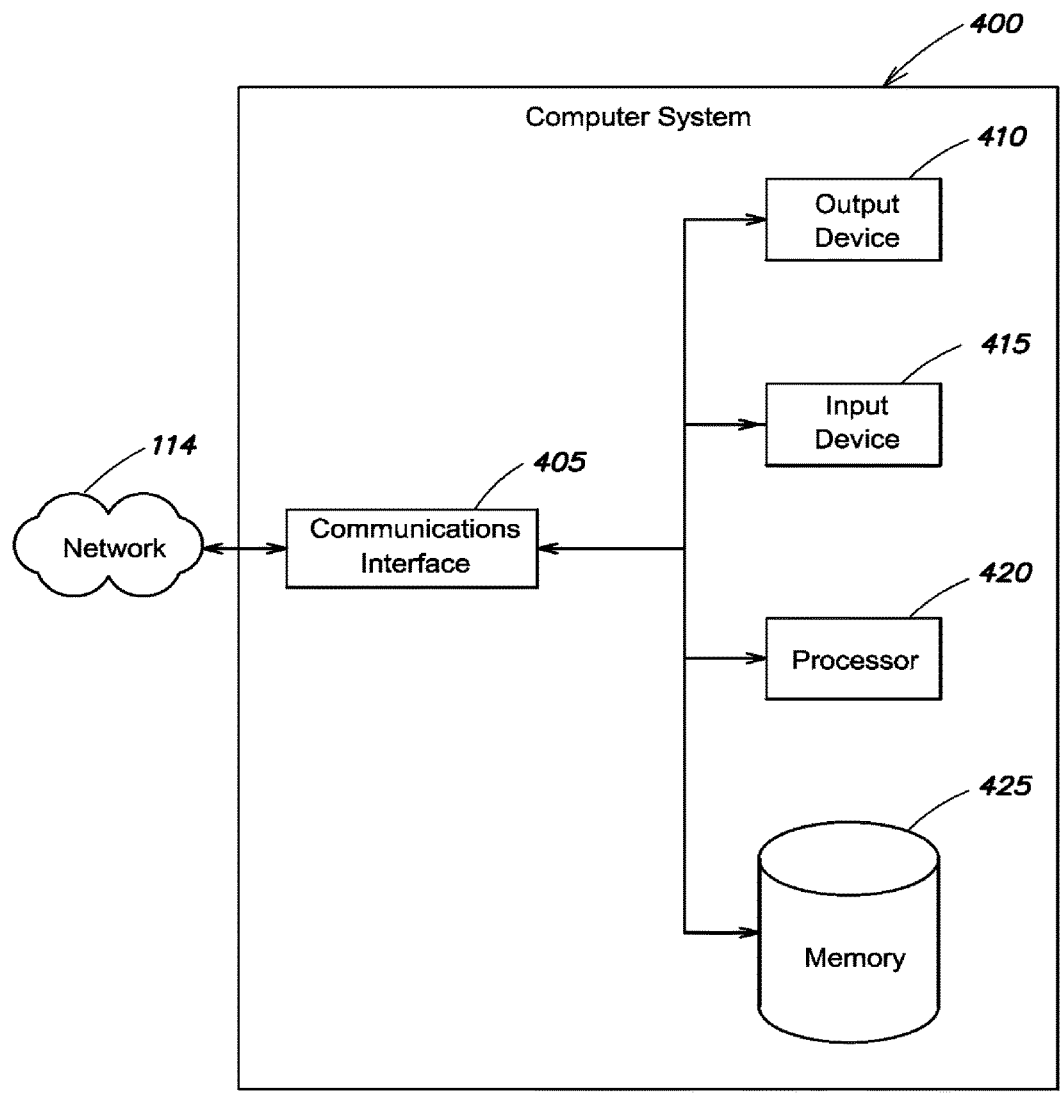
FIG. 4 shows a general architecture for a computer system, according to the principles herein.

FIG. 4 shows the general architecture of an illustrative computer system 400 that may be employed to implement any of the computer systems discussed herein. The computer system 400 of FIG. 4 includes one or more processors 420 communicatively coupled to memory 425, one or more communications interfaces 405, and one or more output devices 410 (e.g., one or more display units) and one or more input devices 415.

In the computer system 400 of FIG. 4, the memory 425 may include any computer-readable storage media, and may store computer instructions such as processor-executable instructions for implementing the various functionalities described herein for respective systems, as well as any data relating thereto, generated thereby, or received via the communications interface(s) or input device(s). The processor(s) 420 shown in FIG. 4 may be used to execute instructions stored in the memory 425 and, in so doing, also may read from or write to the memory various information processed and or generated pursuant to execution of the instructions.

The processor 420 of the computer system 400 shown in FIG. 4 also may be communicatively coupled to or control the communications interface(s) 405 to transmit or receive various information pursuant to execution of instructions. For example, the communications interface(s) 405 may be coupled to a wired or wireless network, bus, or other communication means and may therefore allow the computer system 400 to transmit information to and/or receive information from other devices (e.g., other computer systems). While not shown explicitly in the system of FIG. 4, one or more communications interfaces facilitate information flow between the components of the system 100. In some implementations, the communications interface(s) may be configured (e.g., via various hardware components or software components) to provide a website as an access portal to at least some aspects of the computer system 400.

The output devices 410 of the computer system 400 shown in FIG. 4 may be provided, for example, to allow various information to be viewed or otherwise perceived in connection with execution of the instructions. The input device(s) 415 may be provided, for example, to allow a user to make manual adjustments, make selections, enter data or various other information, or interact in any of a variety of manners with the processor during execution of the instructions.

According the principles disclosed herein, both the communication module and the analyzer can be disposed in the same device, such as, but not limited to, stand alone physical quantification device, a device incorporated into clothing, or a device incorporated into protective equipment. In another example, the communication module may be integrated with the conformal sensor device. In this example, the conformal sensor device may communicate with the analyzer wirelessly, using LEDs, or any other communication means. In some examples, the analyzer may be disposed proximate to the communication module or the analyzer can be a component of a monitoring device to which the measurement data collected by the communication module is transferred.

In an example, the communication module can include a near-field communication (NFC)-enabled component.

In a non-limiting example, the systems, methods and apparatus described herein for providing an indication of the performance of the individual may be integrated with a conformal sensor device that provides the measurement data. In this example, the conformal sensor device may communicate with the analyzer wirelessly or using an indicator. Non-limiting examples of indicators include LEDs or any other communication means.

In a non-limiting example, the conformal sensor device includes one or more electronic components for obtaining the measurement data. The electronic components include a sensor component (such as but not limited to an accelerometer or a gyroscope). The electronics of the conformal sensor device can be disposed on a flexible and/or stretchable substrate and coupled to one another by stretchable interconnects. The stretchable interconnect may be electrically conductive or electrically non-conductive. According to the principles herein, the flexible and/or stretchable substrate can include one more of a variety of polymers or polymeric composites, including polyimides, polyesters, a silicone or siloxane (e.g., polydimethylsiloxane (PDMS)), a photo-patternable silicone, a SU8 or other epoxy-based polymer, a polydioxanone (PDS), a polystyrene, a parylene, a parylene-N, an ultrahigh molecular weight polyethylene, a polyether ketone, a polyurethane, a polyactic acid, a polyglycolic acid, a polytetrafluoroethylene, a polyamic acid, a polymethyl acrylate, or any other flexible materials, including compressible aerogel-like materials, and amorphous semiconductor or dielectric materials. In some examples described herein, the flexible electronics can include non-flexible electronics disposed on or between flexible and/or stretchable substrate layers, such as but not limited to discrete electronic device islands interconnected using the stretchable interconnects. In some examples, the one or more electronic components can be encapsulated in a flexible polymer.

In various non-limiting examples, the stretchable interconnect can be configured as a serpentine interconnect, a zig-zag interconnect, a rippled interconnects, a buckled interconnect, a helical interconnect, a boustrophedonic interconnect, a meander-shaped interconnect, or any other configuration that facilitates stretchability.

In an example, the stretchable interconnect can be formed form an electrically conductive material.

In any of the examples described herein, the electrically conductive material (such as but not limited to the material of the electrical interconnect and/or the electrical contact) can be, but is not limited to, a metal, a metal alloy, a conductive polymer, or other conductive material. In an example, the metal or metal alloy of the coating may include but is not limited to aluminum, stainless steel, or a transition metal, and any applicable metal alloy, including alloys with carbon. Non-limiting examples of the transition metal include copper, silver, gold, platinum, zinc, nickel, titanium, chromium, or palladium, or any combination thereof. In other non-limiting examples, suitable conductive materials may include a semiconductor-based conductive material, including a silicon-based conductive material, indium tin oxide or other transparent conductive oxide, or Group III-IV conductor (including GaAs). The semiconductor-based conductive material may be doped.

In any of the example structures described herein, the stretchable interconnects can have a thickness of about 0.1 µm, about 0.3 µm, about 0.5 µm, about 0.8 µm, about 1 µm, about 1.5 µm, about 2 µm, about 5 µm, about 9 µm, about 12 µm, about 25 µm, about 50 µm, about 75 µm, about 100 µm, or greater.

In an example system, apparatus and method, the interconnects can be formed from a non-conductive material and can be used to provide some mechanical stability and/or mechanical stretchability between components of the conformal electronics (e.g., between device components). As a non-limiting example, the non-conductive material can be formed based on a polyimide.

In any of the example devices according to the principles described herein, the non-conductive material (such as but not limited to the material of a stretchable interconnect) can be formed from any material having elastic properties. For example, the non-conductive material can be formed from a polymer or polymeric material. Non-limiting examples of applicable polymers or polymeric materials include, but are not limited to, a polyimide, a polyethylene terephthalate (PET), a silicone, or a polyeurethane. Other non-limiting examples of applicable polymers or polymeric materials include plastics, elastomers, thermoplastic elastomers, elastoplastics, thermostats, thermoplastics, acrylates, acetal polymers, biodegradable polymers, cellulosic polymers, fluoropolymers, nylons, polyacrylonitrile polymers, polyamide-imide polymers, polyarylates, polybenzimidazole, polybutylene, polycarbonate, polyesters, polyetherimide, polyethylene, polyethylene copolymers and modified polyethylenes, polyketones, poly(methyl methacrylate, polymethylpentene, polyphenylene oxides and polyphenylene sulfides, polyphthalamide, polypropylene, polyurethanes, styrenic resins, sulphone based resins, vinyl-based resins, or any combinations of these materials. In an example, a polymer or polymeric material herein can be a DYMAX® polymer (Dymax Corporation, Torrington, Conn.). or other UV curable polymer, or a silicone such as but not limited to ECOFLEX® (BASF, Florham Park, N.J.).

In any example herein, the non-conductive material can have a thickness of about 0.1 µm, about 0.3 µm, about 0.5 µm, about 0.8 µm, about 1 µm, about 1.5 µm, about 2 µm or greater. In other examples herein, the non-conductive material can have a thickness of about 10 µm, about 20 µm, about 25 µm, about 50 µm, about 75 µm, about 100 µm, about 125 µm, about 150 µm, about 200 µm or greater.

In the various examples described herein, the conformal sensor device includes at least one sensor component, such as but not limited to an accelerometer and/or a gyroscope. In one example, the data receiver can be configured to detect acceleration, change in orientation, vibration, g-forces and/or falling. In some examples, the accelerometer and/or gyroscope can be fabricated based on commercially available, including "commercial off-the-shelf" or "COTS" electronic devices that are configured to be disposed in a low form factor conformal system The accelerometers may include piezoelectric or capacitive components to convert mechanical motion into an electrical signal. A piezoelectric accelerometer may exploit properties of piezoceramic materials or single crystals for converting mechanical motion into an electrical signal. Capacitive accelerometers can employ a silicon micro-machined sensing element, such but not limited to a micro-electrical-mechanical system, or MEMS, sensor component. A gyroscope can be used to facilitate the determination of refined location and magnitude detection. As a non-limiting example, a gyroscope can be used for determining the tilt or inclination of the body part to which it is coupled. As another example, the gyroscope can be used to provide a measure of the rotational velocity or rotational acceleration of the body part (such as an arm in a throwing motion, including a hitting or kicking motion). For example, the tilt or inclination can be computed based on integrating the output (i.e., measurement) of the gyroscope.

In some examples, the system can be used to monitor the performance of an individual during athletic activities, such as but not limited to contact sports, noncontact sports, team sports and individual sports. Non-limiting examples of such athletic activity can include tackles in American football, and the throw of a baseball player or an American football player. This can occur during games, athletic events, training and related activities. Other examples of performance monitoring can be during construction work (or other industrial work), military activity, occupation therapy, and/or physical therapy.

In any example herein, the indication of the individual's performance may be quantified based on a computed imparted energy and/or a HIC, and data indicative of a physiological condition of the individual, such as but not limited to a blood pressure, a heart rate, an electrical measurement of the individual's tissue, or a measurement of a device proximate to the individual's body (including an accelerometer, a gyro, a pressure sensor, or other contact sensor).

An example conformal sensor device can include electronics for performing at least one of an accelerometry measurements and electronics for performing at least one other measurement. In various examples, the at least one other measurement can be, but is not limited to, a muscle activation measurement, a heart rate measurement, an electrical activity measurement, a temperature measurement, a hydration level measurement, a neural activity measurement, a conductance measurement, an environmental measurement, and/or a pressure measurement. In various examples, the conformal sensor device can be configured to perform any combination of two or more different types of measurements.

The example systems, methods, and apparatus described herein including the conformal sensor system can be configured to monitor the body motion and/or muscle activity, and to gather measured data values indicative of the monitoring. The monitoring can be performed in real-time, at different time intervals, and/or when requested. In addition, the example systems, methods, and apparatus described herein can be configured to store the measured data values to a memory of the system and/or communicate (transmit) the measured data values to an external memory or other storage device, a network, and/or an off-board computing device. In any example herein, the external storage device can be a server, including a server in a data center.

This example systems, methods, and apparatus can be used to provide ultra-thin and conformal electrodes that, when combined with motion and activity measurements, facilitate monitoring and diagnosis of subjects. In combination with pharmaceuticals, this information can be used to monitor and/or determine subject issues including compliance and effects.

The example conformal sensor system can be configured to provide a variety of sensing modalities. The example conformal sensor system can be configured with sub-systems such as telemetry, power, power management, processing as well as construction and materials. A wide variety of multi-modal sensing systems that share similar design and deployment can be fabricated based on the example conformal electronics.

According to the principles disclosed herein, the example conformal sensor device can include a storage device. The storage device can be configured to store the data indicative of the quantified performance and/or the measurement data. The storage device can be, but is not limited to, a flash memory, solid state drives, removable memory cards, or any combination thereof.

In another example, the system for quantifying performance of an individual can include a transmission module. The transmission module can be configured to transmit the data indicative of the quantified performance and/or the measurement data to an external device. For example, the transmission module can transmit the data indicative of the quantified performance and/or the measurement data to a computing device such as but not limited to a smartphone (such as but not limited to an Iphone®, an Android™ phone, or a Blackberry®), a tablet computer, a slate computer, an electronic gaming system (such as but not limited to an XBOX®, a Playstation®, or a Wii®), and/or an electronic reader. The analyzer may be processor-executable instructions implemented on the computing device. In another example, the transmission module can transmit data using a communication protocol based on Bluetooth® technology, Wi-Fi, Wi-Max, IEEE 802.11 technology, a radio frequency (RF) communication, an infrared data association (IrDA) compatible protocol, or a shared wireless access protocol (SWAP).

In one example, the processor-executable instructions can include instructions to cause the processor to maintain a cumulative total of the number of detected performance events, such as but not limited to the number of throws, kicks, swings, and/or footfalls, during an activity. In some implementations, the cumulative total can be subdivided responsive to a number of performance threshold values, such as but not limited to first, second, and third performance threshold values. As a non-limiting example, a performance threshold can be set based on a preset amount of imparted energy and/or level of HIC. For example, performance thresholds can be preset for differing levels of imparted energy of a baseball player's or football player's arm for a throw, a football or soccer player's foot for a kick, a baseball player's or golfer's arm for swings, and/or a runner's or horse's footfalls.

In some examples, the processor-executable instructions can include instructions to cause the processor to maintain counts for each of a number of bins created by differing predetermined thresholds (including performance threshold values). A bin count can be increment when the quantitative measure of the performance of the individual corresponds to a specific bin. In some examples, the processor-executable instructions can include instructions to cause the processor to maintain counts for each of the bins created by the predetermined threshold and increment the counts when a performance measure is registered corresponding to a specific bin. For example, a first bin may include the quantitative measure of the performance for a specific imparted energy above a first threshold but below a second threshold, a second bin may include the quantitative measure of the performance with an imparted energy value above the second threshold but below a third threshold, and a third bin may include any quantitative measures of the performance with an imparted energy value above the third threshold. The processor-executable instructions can include instructions to cause the processor to transmit the cumulative counts for each bin to an external device via a transmission module. The counts for each bin can be reset at predetermined intervals. For example, processor-executable instructions can include instructions to cause the processor to track the number of counts for each bin an athlete registers over a time period, and the counts from the bins may be used as an overall rating of the performance of the individual. In another example, the cumulative count of a bin, such as but not limited to a bin indicative of poorer performance, may be used to indicate a physical condition of the individual. For example, the cumulative count in the bin indicative of poorer performance may be used to indicate that an individual, such as but not limited to a football player or a baseball player, should be benched within a certain period of time. Based on bin counts indicative of throw counts for a baseball player or football player that has a conformal sensor device disposed on an arm, the baseball player's performance level may be categorized. Non-limiting example categories include satisfactory, in need of further training, needing to be benched for the remained of the game, unsatisfactory, or any other type of classification.

According to the principles described herein, the cumulative totals can be gathered over specific periods of time such a construction worker's shift, a specific duration of time, a game, a season, and/or a career. In some examples, the processor-executable instructions cause the processor to calculate a head injury criterion (HIC). The HIC and imparted energy can be used as a measure of the likelihood that an impact can cause a head injury.

In some example implementations, the processor-executable instructions can cause the processor to perform a linear interpolation of the received data to generate data for the data points that are not measured by the data receiver. For example, the processor-executable instructions can cause the processor to perform a curve fit based on a pre-determined waveform to generate the non-measured data. In one example, the waveform can be determined based on a priori knowledge of candidate waveforms or a curve fit based on a set of known standards of the performance of low-g accelerometers for different applied forces. For example, low-g accelerometer may have a dynamic range capable of detecting up to only about 10 g forces. The device may be subjected to forces outside the device's dynamic range during the course of an activity. In some example implementations, prior knowledge of candidate waveform shapes can be used to recreate a standard waveform for analysis by the hit count monitor.

In various examples described herein, the performance quantification device can be configured to include an indicator. The indicator can be used to directly display or transmit count and/or data indicative of performance. In one example, the indicator provides a human readable interface, such as a screen that displays the collected data. This sequence of displayed values can be triggered but not limited to a specific action or sequence related to obtaining the displayed values such as a reset or power off and power on sequence.

In another human readable example, the indicator may include LEDs that blink or glow at a specific color to indicate the level of performance of the individual. In this example, the indicator can be used to blink (turn on and off) a detectable sequence of light flashes that corresponds to the performance level above a predetermined threshold. A sequence of on and off flashes can be counted to give a specific number. As a non-limiting example, the sequence <on>, <off>, <on>, <off>, <on>, <off>, could correspond to 3 instances of quantified performance above the threshold. For double-digits (above 9 instances of quantified performance) the numbers might be indicated thusly: <on>, <off>, <pause>, <on>, <off>, <on>, <off> would correspond to 12 instances of quantified performance using decimal notation. While a useful duration of the <on> pulses could be in the range of 10-400 milliseconds, any observable duration can be used. The <pause> should be perceptibly different from than the <on> signal (including being longer or shorter) to indicate the separation of numbers. This sequence of displayed values can be triggered but not limited to a specific action or sequence related to obtaining the displayed values such as a reset or power off and power on sequence.

Start and end sequences may be used to bracket the signal values such as a rapid pulsing or specific numerical values. Another numerical sequence can be used to provide a unique ID for a wearable unit including the conformal sensor device.

The framework for the display of pulses can also be programmable and set up via a computer connection (wireless or wired) to tailor the sequence for specific needs. While multiple values can be communicated using longer flashing sequences, this may be less desirable due to issues of time, and complexity of interpretation. An encoding akin to a human readable Morse code-like sequence or pulse width modulation can provide more information but also may require significant training and transcription.

In yet another example, the indicator can be configured to provide a non-human readable indicator in addition to, or in place of, the human readable indicator. For example, a smartphone application (or other similar application of processor-executable instructions on a computing device) can be used to read or otherwise quantify an output of an indicator using a camera or other means. For example, where the indicator provides an indication or transmits information using LEDs, the camera or other imaging component of a smartphone or other computing device may be used to monitor the output of the indicator. Examples of non-human readable interfaces using an LED include blinking the LED at a rate that cannot be perceived by the human eye, LEDs that emit electromagnetic radiation outside of the visual spectrum such as infrared or ultraviolet, and/or LEDs that glow with low luminosity such that they cannot be perceived by a human.

Non-limiting examples of computing devices herein include smartphones, tablets, slates, e-readers, or other portable devices, of any dimensional form factor (including mini), that can be used for collecting data (such as, but not limited to, a count and/or measures of performance) and/or for computing or other analysis based on the data (such as but not limited to computing the count, calculating imparted energy, and/or determining whether a measure of performance is above or below a threshold). Other devices can be used for collecting the data and/or for the computing or other analysis based on the data, including computers or other computing devices. The computing devices can be networked to facilitate greater accessibility of the collected data and/or the analyzed data, or to make it generally accessible.

In another non-limiting example, the performance monitor can include a reader application including a computing device (such as but not limited to a smartphone-, tablet-, or slate-based application), that reads the LED display from an indicator, calculates tiered counts from tiered indications of the performance indicator, and logs the data to the memory of the performance monitor. In a non-limiting example, the tiered indication may be a green light indication for performance quantified as reaching a first performance threshold, a yellow light indication for performance quantified as reaching a second performance threshold, and red light indication for performance quantified as reaching a third threshold, or any combination thereof. The application can be configured to display the counts, or indicate a recommendation for future activity. In an example where the individual is an athlete, the performance monitor may provide an indication of the recommended remaining hits for a player for that specific game, for the season, for the career, etc. The example system and apparatus can be configured to send data and performance reports to selected recipients (with appropriate consent) such as but not limited to parents, trainers, coaches, and medical professionals. The data can also be aggregated over time to provide statistics for individual players, groups of players, entire teams or for an entire league. Such data can be used to provide information indicative of trends in game play, effects of rule changes, coaching differences, differences in game strategy, and more.

In any example provided herein where the subject is an individual, it is contemplated that the system, method or apparatus has obtained the consent of the individual, where applicable, to transmit such information or other report to a recipient that is not the individual prior to performing the transmission.

Wearable electronics devices can be used to sense information regarding particular motion events (including other physiological measures). Such motion indicator devices, including units that are thin and conformal to the body, can provide this information to users and others (with appropriate consent) in a variety of ways. Some non-limiting examples include wireless communication, status displays, haptic and tactile devices, and optical communication. In the case of a motion indicator, such as those described in U.S. patent application Ser. Nos. 12/972,073, 12/976,607, 12/976,814, 12/976,833, and/or 13/416,386, each of which is incorporated herein by reference in its entirety including drawings, the wearable electronics device described herein can be used to register and store numbers of instances of quantified performance above a threshold, or other physiological data, onboard.

As a non-limiting example of a smart lighting devices that may be applicable to a hit count monitor according to the principles described herein, U.S. Pat. No. 6,448,967, titled "Universal Lighting Network Methods and Systems," which is incorporated herein by reference in its entirety including drawings, describe a device that is capable of providing illumination, and detecting stimuli with sensors and/or sending signals. The smart lighting devices and smart lighting networks may be used for communication purposes.

As a non-limiting example, the example systems, methods, and apparatus described herein can be configured to count pitches and throws, and to analyze and quantify data indicative of the complementary metrics around the throwing motion. Example systems, methods, and apparatus described herein can be implemented to collect and/or analyze data that can be used to determine, as non-limiting examples, the number of throws in a given session, the arm movement during a throw, and estimate throw data including peak velocity and/or values of velocity of a ball or other thrown or struck object, and throw plane.

Any example system, method or apparatus according to the principles described herein can be used to monitor and or analyze data from a body part performing a similar motion using an object (including a baseball glove or mitt, a racket, a hockey stick), to strike or to catch another object (including a ball or a puck).

Any example system, method or apparatus herein applied to quantify or analyze a throwing motion also can be applied to quantify or analyze a striking motion using an object.

As a non-limiting example, an output of the example systems, methods, and apparatus according to the principles described herein can be a value or designation indicating a measure of throw velocity, throw quality, throw plane, proper throw form, or other measure of throw.

Figure 5:
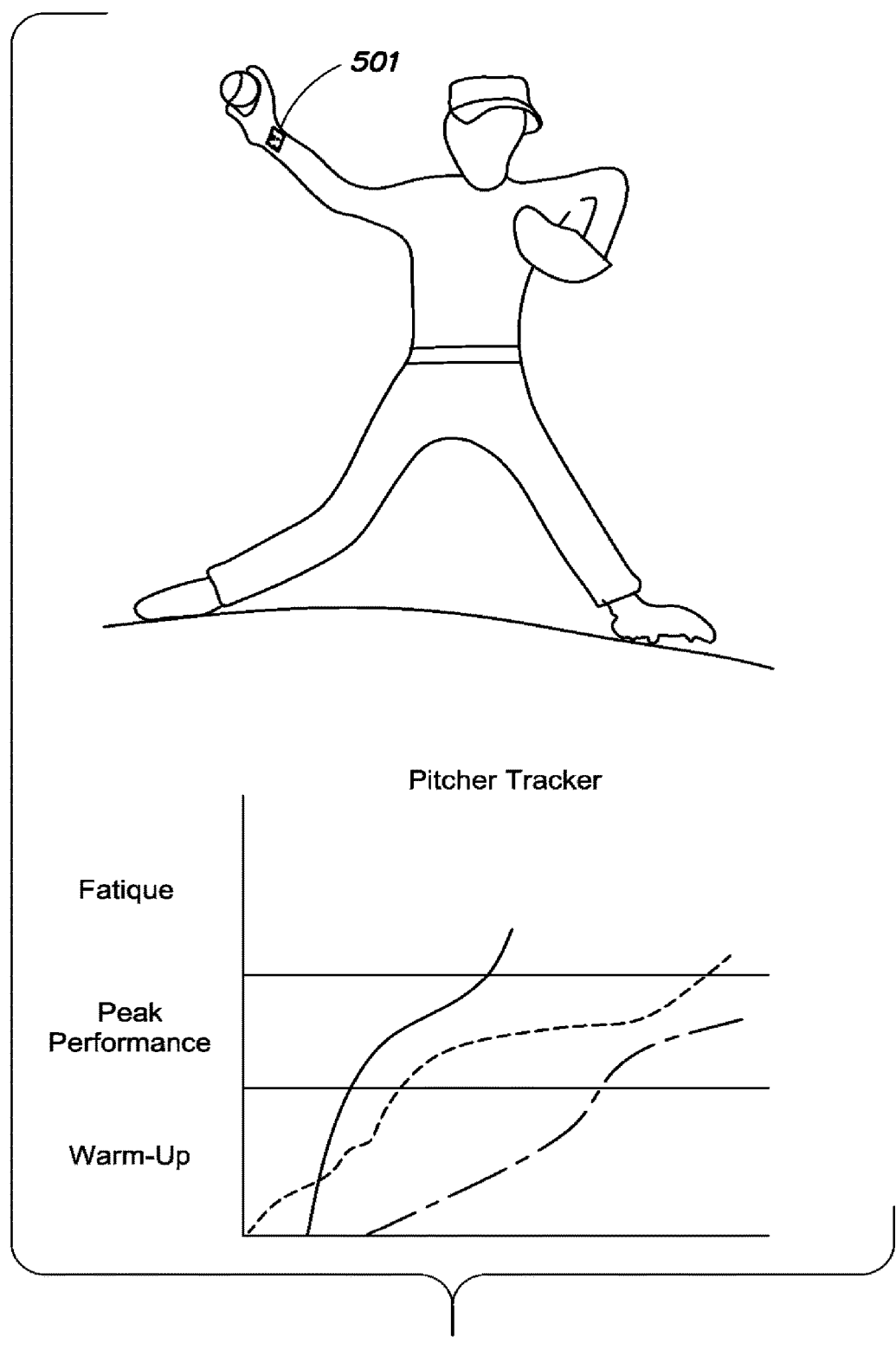
FIG. 5 shows an example system for monitoring performance, according to the principles herein.

FIG. 5 shows an example of use of measurements from a conformal sensor device for monitoring performance. In an example, the conformal sensor device can be disposed proximate to, attached to, or otherwise coupled to, the muscle(s) of interest during specific, repeated or repetitious exercise. The example of FIG. 5 shows the example conformal sensor system on an individual's body part, such as but not limited to a baseball pitcher's arm. The individual's muscle activity and/or motion is tracked during a warm up period to assess quality of muscle activation and readiness or during the pitching performance in a game. A user, such as but not limited to a coach, a trainer, or an athlete can (with appropriate consent) use analysis of the measurement data to assess quality of muscular activity to find ideal levels of performance based on EMG frequency and amplitude. After a period of pitching, data from measurements can be used to generate a performance indicator to quantify whether there's a decrease in the quality of muscle response, which can be used for determining fatigue levels and exhaustion. This information facilitates users, e.g., coaching staff, to determine the correct time that a pitcher should be removed from the game and replaced, preventing or reducing the risk of injury. The example systems can also be used to indicate when a different pitcher is warmed up and ready to play. In this example, the three different trend lines on the example graph can be used to represent three different players during a single game. This example implementation can be applied to any athletic sport or other physical activity.

As a non-limiting example, the electronics for muscle activation monitoring can be configured to perform electromyography (EMG) measurements. The electronics for EMG can be implemented to provide a measure of muscle response or electrical activity in response to a stimulation of the muscle. As a non-limiting example, the EMG measurements can be used to detect neuromuscular abnormalities.

For the EMG measurements, electrodes coupled to the example conformal motion sensors can be disposed proximate to the skin and/or muscle, and the electrical activity is detected or otherwise quantified by the electrodes. The EMG can be performed to measure the electrical activity of muscle during rest, or during muscle activity, including a slight contraction and/or a forceful contraction. As non-limiting examples, muscle activity, including muscle contraction, can be caused by, for example, by lifting or bending a body part or other object. Muscle tissue may not produce electrical signals during rest, however, a brief period of activity can be observed when a discrete electrical stimulation is applied using an electrode disposed proximate to the skin and/or muscle. The conformal sensors can be configured to measure, via the electrodes, an action potential. In an example, the action potential is the electrical potential generated when muscle cells are electrically or neurologically stimulated or otherwise activated. As muscle is contracted more forcefully, more and more muscle fibers are activated, producing varying action potentials. Analysis of the magnitude and/or shape of the waveform(s) of the action potentials measured can be used to provide information about the body part and/or the muscle, including the number of muscle fibers involved. In an example, the analysis of the magnitude and/or shape of the waveforms measured using the conformal sensors can be used to provide an indication of the ability of the body part and/or the muscle to respond, e.g., to movement and/or to stimuli. Analysis of spectral or frequency content of such signals can be further used to provide an indication of muscle activation and/or body motion, and associated forces. This data or any other data described herein can be further filtered and/or compressed to reduce the amount of information to be stored.

In an example, data indicative of the conformal sensor measurements, including the measured action potentials, can be stored to a memory of the conformal sensor system and/or communicated (transmitted), e.g., to an external memory or other storage device, a network, and/or an off-board computing device.

In an example, the conformal sensor system can include one or more processing units that are configured to analyze the data indicative of the conformal sensor measurements, including the measured action potentials.

In a non-limiting example, the conformal sensor system may include electronics and be coupled to recording and stimulating electrodes for performing a nerve conduction study (NCS) measurement. The NCS measurement can be used to provide data indicative of the amount and speed of conduction of an electrical impulse through a nerve. Analysis of a NCS measurement can be used to determine nerve damage and destruction. In a NCS measurement, a recording electrode can be coupled to a body part or other object proximate to the nerve (or nerve bundle) of interest, and a stimulating electrode can be disposed at a known distance away from the recording electrode. The conformal sensor system can be configured to apply a mild and brief electrical stimulation to stimulate a nerve (or nerve bundle) of interest via the stimulating electrode(s). Measurement of the response of the nerve (or nerve bundle) of interest can be made via the recording electrode(s). The stimulation of the nerve (or nerve bundle) of interest and/or the detected response can be stored to a memory of the conformal sensor system and/or communicated (transmitted), e.g., to an external memory or other storage device, a network, and/or an off-board computing device.

Figure 6A:
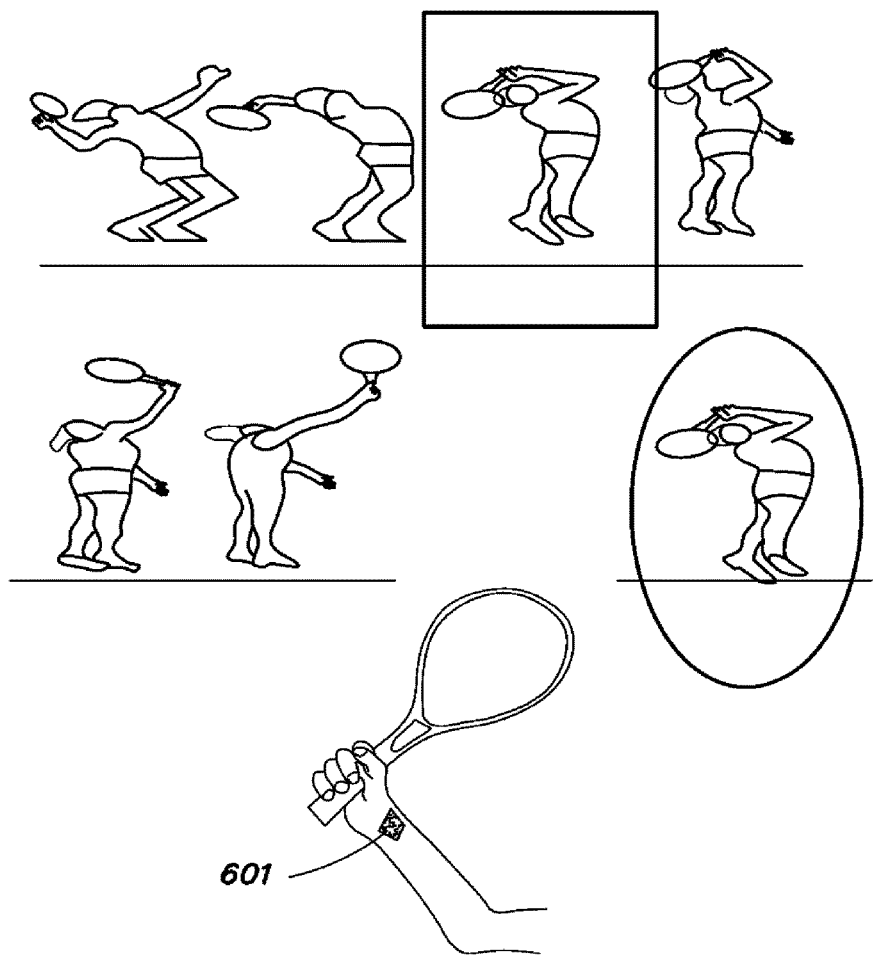
FIGS. 6A and 6B show an example system for monitoring performance based on grip intensity, according to the principles herein.
Figure 6B:
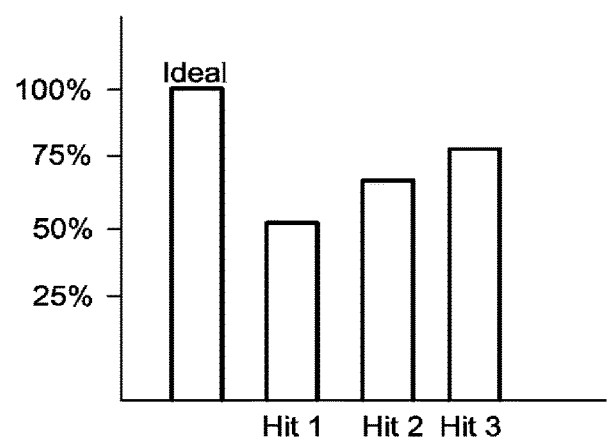

FIGS. 6A and 6B show an example of use of the example systems for monitoring performance based on grip intensity. In this example, muscle activity level measurement can be analyzed to provide an indication of ideal grip intensity. An assessment of the amount of muscle activity in the forearm can be used as an indicator of user grip pressure. The indicator of user grip can be compared data to provide an indication of the desired motion patterns for the user. FIG. 6A shows an example of the phases of a tennis serve. In this example, the data from the accelerometer measurements of the example conformal motion system can be used to determine the phases of the motion, and the data from the EMG measurements of the example conformal sensor system can be used to indicate grip pressure at each phase. After the serve, the example system can be configured to display to the athlete views showing where grip pressure should be adjusted based on analysis of the measured data. The example feedback can also be used to alert a user, in real time, on demand or at different time intervals, audibly or by a changing color on display screen, when the user's grip pressure deviates from the optimal range. FIG. 6B shows an example graphic display, where the user's grip intensity at each hit is compared to an optimal range. Such feedback may be provided in real-time to allow user adjustments to grip intensity to be made.

Figure 7:
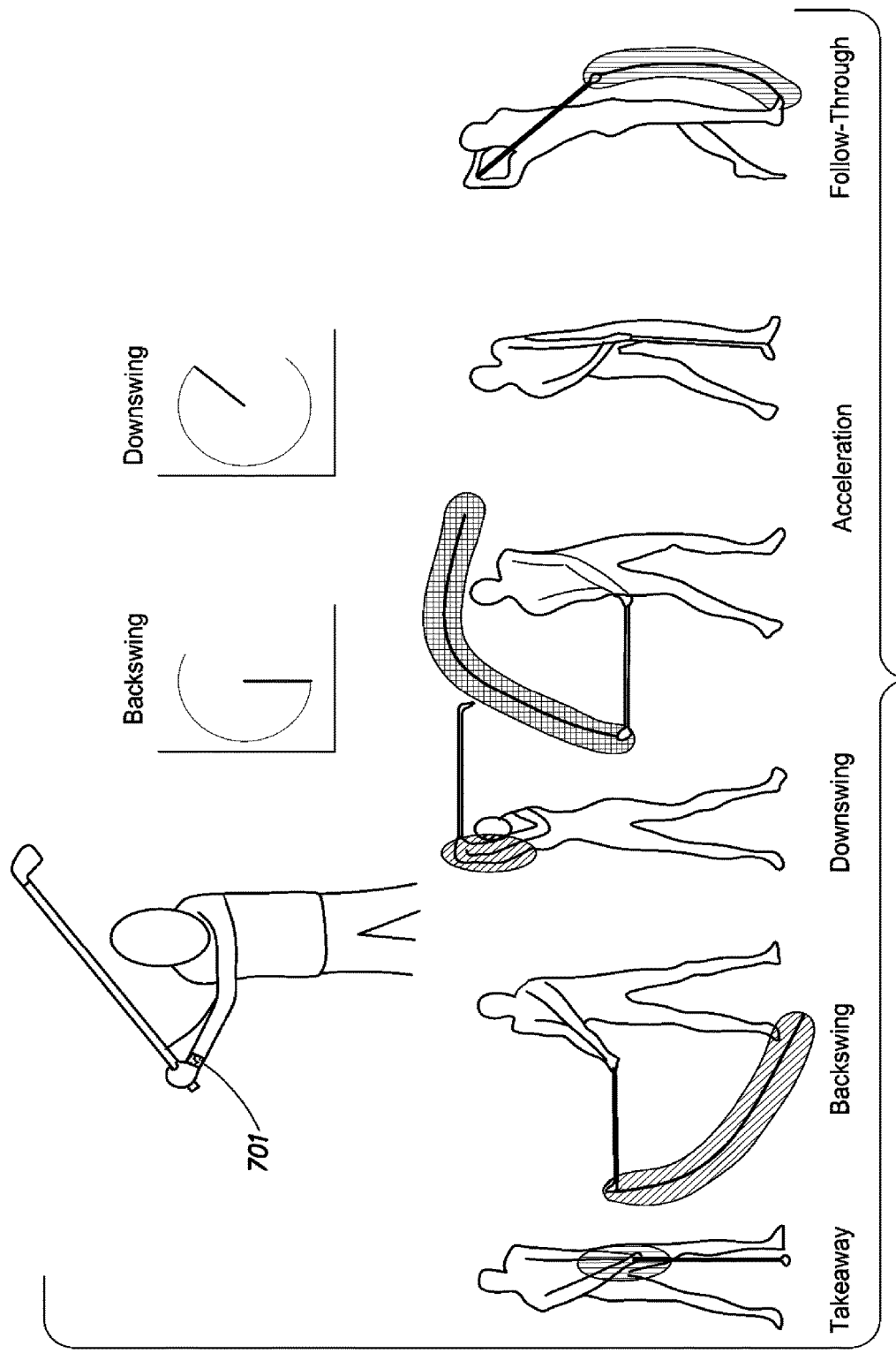
FIG. 7 shows an example system for monitoring performance based on pattern matching, according to the principles herein.

FIG. 7 shows an example of use of the example systems for monitoring performance based on pattern matching. The pattern matching can be performed for an individual or in a professional setting. The analysis of data measured using, e.g., an accelerometer of the example conformal sensor device, can be used to provide corrective movement patterns via pattern matching with ideal or desired motion patterns. FIG. 7 shows an example breakdown of each phase of a golf swing, including takeaway, backswing, downswing, acceleration, and follow-through. The example system can be configured to display an indicator, including a color display, to indicate the result of performance for each phase. For example, a red color can be used to indicate motion deviating from the desired pattern, green can indicate good or acceptable motion, and yellow can be used to indicate small deviation from ideal. In the example of FIG. 7, based on analysis of accelerometer and muscle data, the takeaway is indicated as red, indicating pressure on grip is too strong (e.g., ideal intensity is set at a level of 30 while user intensity is measured at 45). In this example, the backswing, downswing are indicated as green (ideal or acceptable); acceleration is indicated a yellow (indicating club acceleration is measured as too low, and suggesting a 10% increase in acceleration); the follow-through is indicated as a red (e.g., due to club stopped before complete follow-through).

Figure 8:
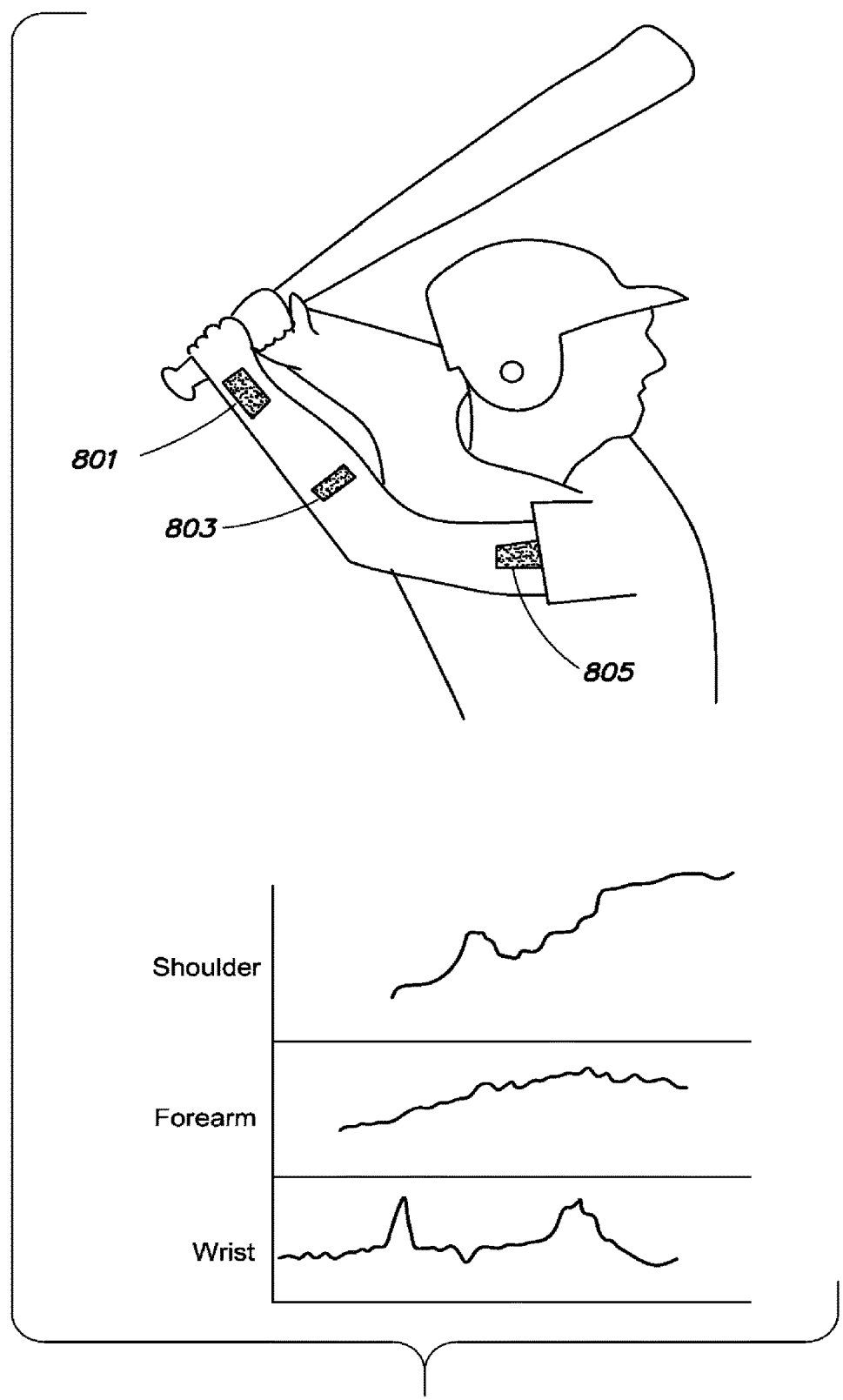
FIG. 8 shows an example system for monitoring performance, according to the principles herein.

FIG. 8 shows an example of use of the example systems for monitoring performance. The example conformal sensor device can be placed on working muscles during an activity. The example shows conformal sensor devices placed on portions of an individual (such as a baseball batter) on various muscles along the arm including wrist, forearm, and/or shoulder. The sensor components can be used to detect measurements indicative of kinetic link, by measuring the order in which muscles or muscle groups are being fired during motion. The analysis of the kinetic link results can be used to assist in determining desired movement patterns to improve movement speed and accuracy. In an example, the example conformal sensor device can include an accelerometer and two or more EMG sensors. The example conformal sensor device can be used to detect the order in which muscles are being fired and provide feedback on differences between the desired (ideal) patterns and the pattern being performed by the individual (such as an athlete). In an example activity involved in a baseball swing, the feedback can be provided in a graph output to assist the individual (in this case, an athlete) to analyze and make adjustments for the next swing.

In an example, a similar analysis can be performed to determine a kinetic link for a kick by placement of the conformal sensor devices on various portions of a leg.

In another example, a similar analysis can be performed to determine a kinetic link for swinging an object (such as but not limited to a golf club, a hockey stick, or a baseball bat) by placement of the conformal sensor devices on various portions of a torso and/or the arms.

Figure 9:
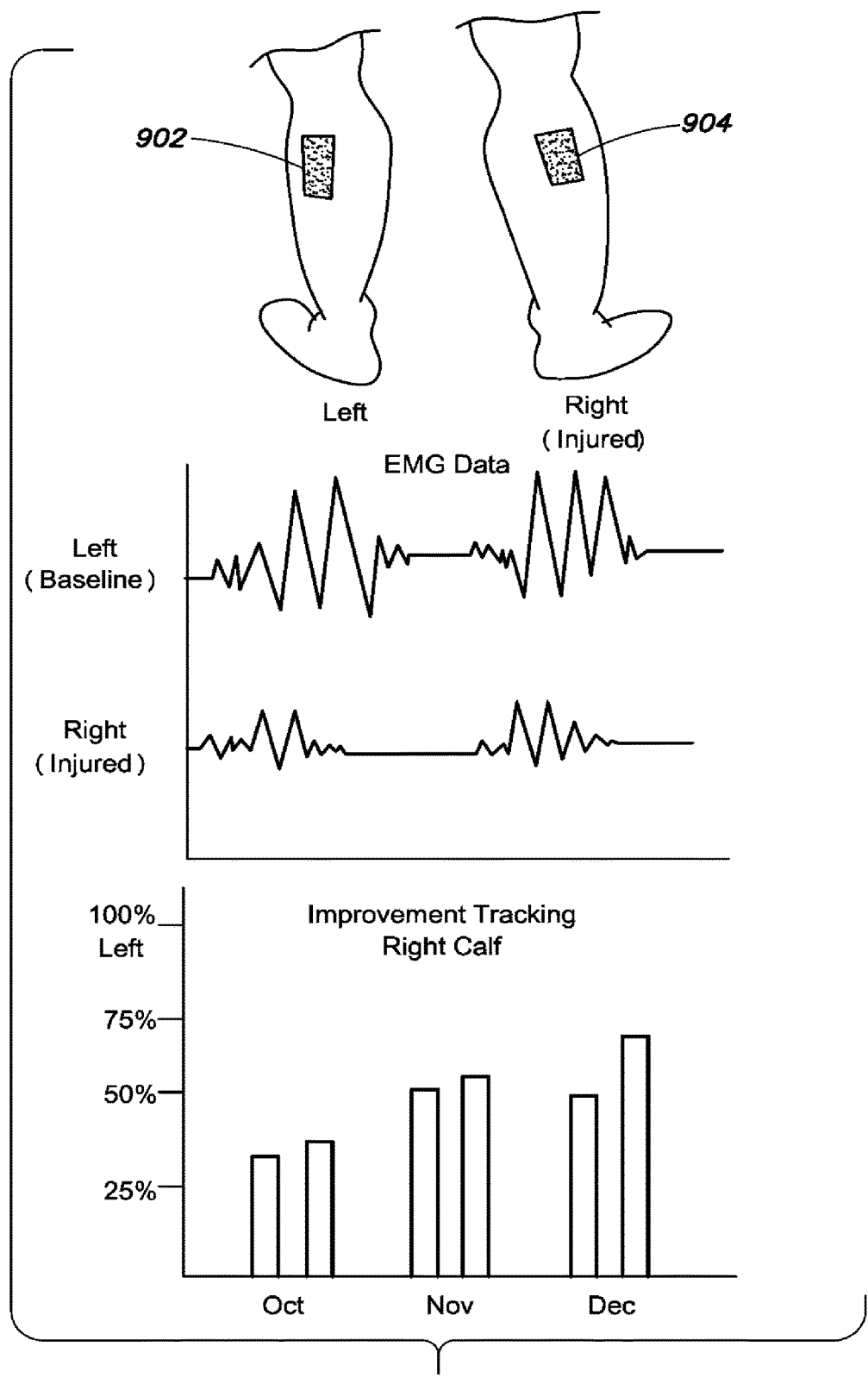
FIG. 9 shows an example system for monitoring performance, according to the principles herein.

FIG. 9 shows an example of use of the example conformal sensor device for monitoring performance for balance and/or symmetry determination. The example system can be configured to include an accelerometer and/or an EMG component. For example, the system can be used for an individual having a lack of symmetry naturally or an injury (e.g., an athlete having a strained right calf). In an example, motion sensors can be applied to or disposed proximate to body parts to determine a baseline of the abnormality. For example, for an individual having a strained right calf, the measurements of the right and left calves can be analyzed to compare the right calf performance against the left calf performance (relative measure). In an example, the conformal sensor device can be disposed on the individual during rehabilitation activities, to provide measurements for determining how the muscle and movement activity on the injured leg during rehabilitation compares to baseline. EMG data can be used to detect relative improvements to determine rehabilitation status of injured leg. Performance and accompanying motion can be tracked over time to determine rate of improvement.

Figure 10:
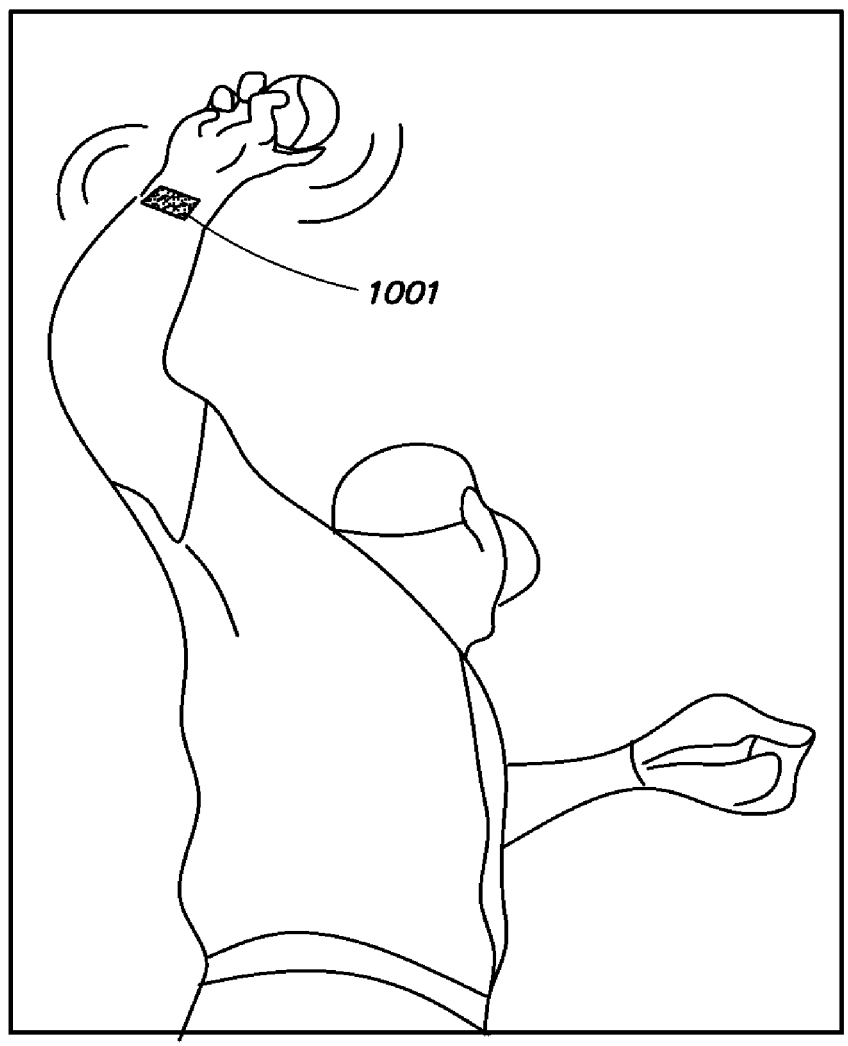
FIG. 10 shows an example conformal sensor device mounted on the skin, according to the principles herein.

FIG. 10 shows an example conformal sensor device 1001 mounted on the skin, on a baseball pitcher's right forearm. Example conformal sensor device 1001 exhibits a degree of conformal contact with the skin, and follows the contours of the arm.

Figure 11:
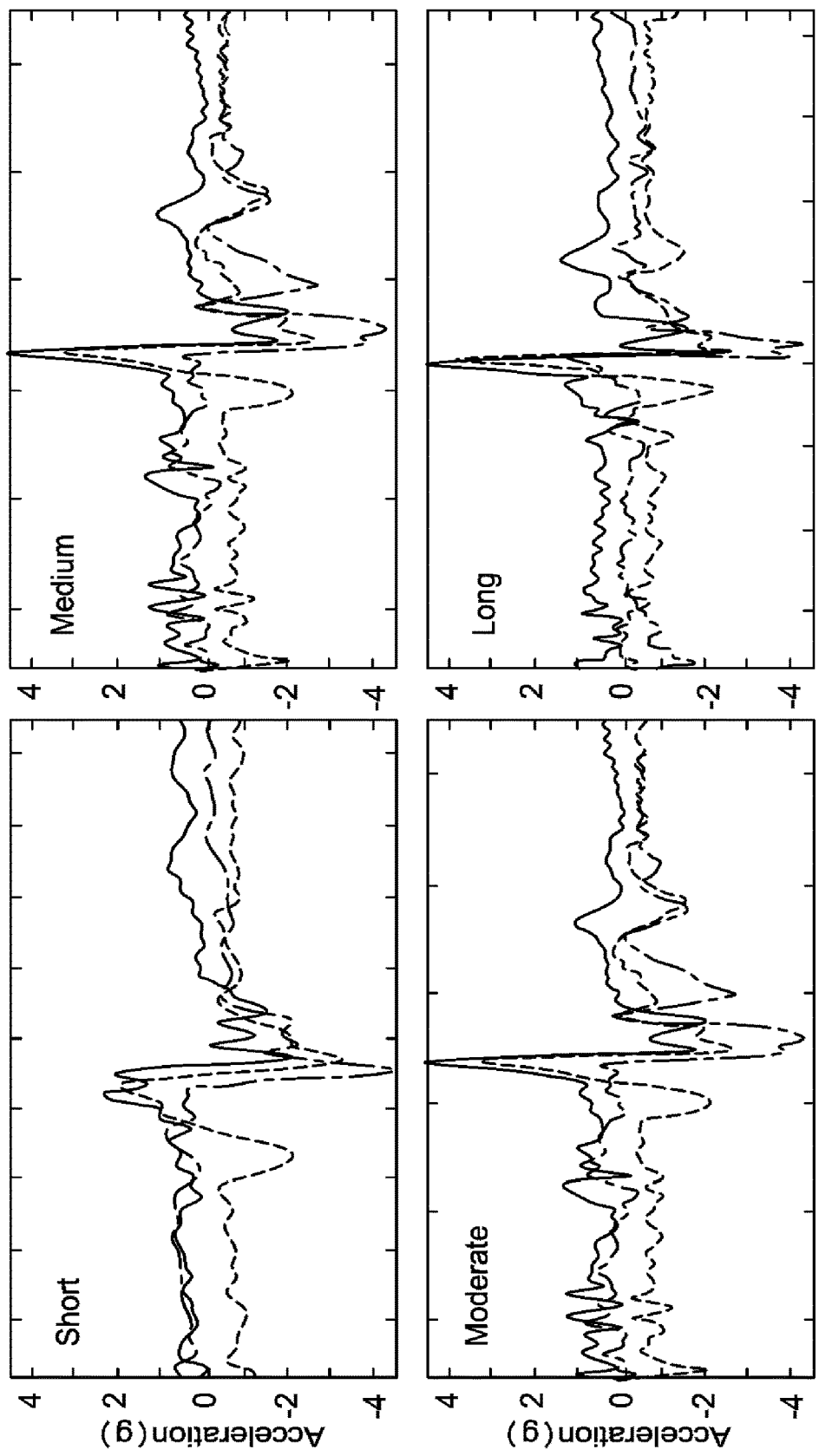
FIG. 11 shows example data, according to the principles herein.

FIG. 11 shows example data, showing the x-y-z acceleration, collected during a single throw, at four distances (short, medium, moderate, long). As shown in FIG. 11, the data can be collected using an example conformal sensor device, e.g., coupled to or worn on a body part.

Figure 12:
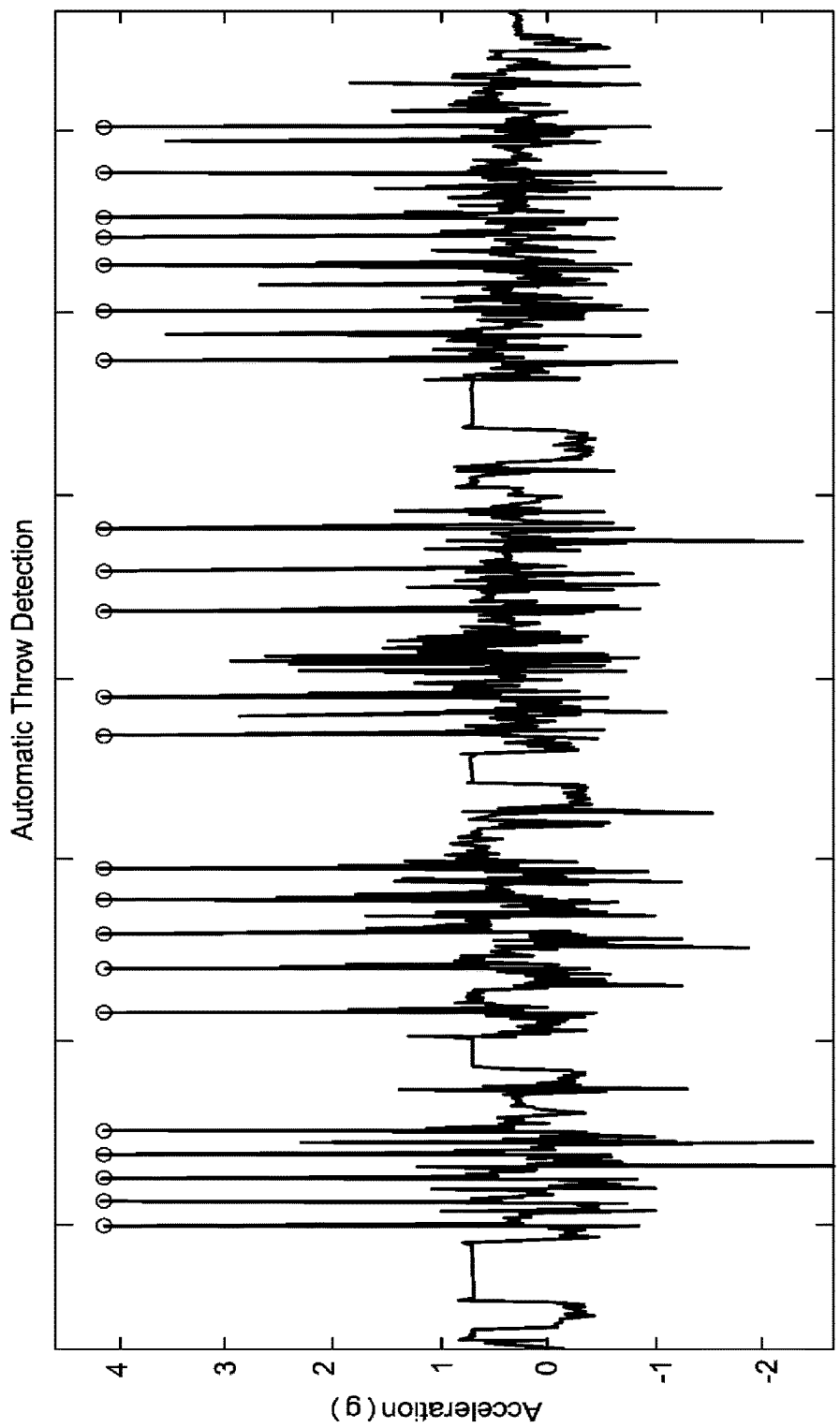
FIG. 12 shows example data collected during throwing activity, according to the principles herein.

FIG. 12 shows example data collected during throwing activity, showing the feasibility of capturing number of throws over a series of throw sessions. Each circle on the graph represents a single throw.

In a non-limiting example implementation, a system herein can be configured for monitoring performance as a wearable rehabilitation monitor.

For example, patches can be applied to the right and left calves of an athlete that has a strained right calf. The data collected from the patch at the left calf can be used as a baseline, and compared to the data collected from the patch at the abnormally performing right calf as a relative measure.

In a non-limiting example, a motion-sensing patch can be disposed on a portion of a leg during rehabilitation activity to monitor the muscle and movement activity using both a baseline sensor on one leg and on the other. In an example, the analysis can include looking for relative improvements. The analysis can provide a quantitative measure to determine how close the injured and healthy legs are to each other in performance and motion. The specific dimension of the metric used for the measurements are canceled out where the analysis is performed to provide a relative measure of improvement or performance change.

Non-limiting example measurement data collection and analysis include: measuring cadence/gait (e.g., using accelerometer), measuring muscle activation (e.g., using electromyography (EMG)), observing patterns of motion (e.g., using time sequence) and pattern of activation, and/or computing a measure of symmetry (with a determined range of acceptable tolerance). Output can be a measure or other indication of readiness-the measure or indication can be classified as indicating, e.g., continue rehabilitation, or return to play, or return to work, etc.

In many occupations, including athletics, at some point, an individual is injured. Using the example systems, methods, and apparatus according to the principles described herein, measured changes can be mapped to give a rate of change (improvement trend)) and provide an estimated time of return to active duty or return to play or return to full function. These metrics of motion, speed, acceleration, can be also used to provide an envelope (bounds) of change and improvement.

A method for provide baseline motion and tracking changes or improvements is also provided according to the example systems, methods, and apparatus described herein.

It is sometimes the case that an individual does not notice an injury with the injury during athletic activity or other occupation. Example systems, methods, and apparatus according to the principles described herein provide a platform to independently assess motion and behavior.

Toe strike, or motion cadence, or gait, can be used to track change and improvement (or decline) in progress during rehabilitation, training, and/or in real-time during a game.

Data indicative of the time sequence of motion of portions of the individual and patterns of muscle activation can be used to calculate a notion of symmetry and comparison. This becomes an issue of readiness which can be presented as a value or percentage.

As a non-limiting example, an output of the example systems, methods, and apparatus according to the principles described herein can be a value or designation indicating a measure of readiness for an activity. In this example, readiness can be defined by symmetry. As non-limiting example, pattern, magnitude and other signal processing means can be used.

In an example implementation, a baseline can be computed based on measurements from a first conformal sensor device and used to determine "symmetry." Comparison of the measurements from the first conformal sensor device to measurements from a second conformal sensor device disposed at a different portion of the individual. A measure of baseline activation levels (magnitude) can be used to determine the individual's strength. A measure of baseline accelerations (magnitudes) can be used to determine the individual's gait.

In an example implementation, the systems can be implemented for site-specific motion modeling.

The example systems, methods, and apparatus according to the principles described herein re provide better performance than large and bulky devices for looking at body motion. Some of the bulkier systems can be external (video capture) devices that are used for gait and body motion analysis.

In an example implementation, the systems can be configured for motion pattern matching. An athlete or other individual can be caused to follow a template of "idealized" motion. The example systems and methods can include one or more display devices to display this information in numerical or graphic form. Analysis of data gathered while the athlete or other individual follows this template of "idealized" motion can be used to provide an assessment that assists the trainer or other user to improve training and motion.

The trainer, user, athlete or other individual can get feedback from the example systems, methods, or apparatus described herein of data indicating the analysis of actual motion of the athlete or other individual. Based on this feedback, the athlete or other individual may change behavior or otherwise monitor performance.

In an example implementation, the systems can be configured for monitoring performance of a golf or baseball player. A graphic presentation on the display device can be in the form of plotted data, numerical data or a visualization of stance and body configuration. For the purposes of training, the visual can be exaggerated to give a better feel for the changes.

In an example implementation, the systems can be configured to provide a wearable performance assessment and improvement.

In an example implementation, the systems can be configured for aiding in evaluating the performance of multiple athletic during scouting activity. The evaluation is based on actual data from an individual, to strength, speed, dexterity, agility etc. The example systems, methods and apparatus described herein can be used to deploy conformal sensor devices to capture real-world performance data In an example implementation, the systems can be configured for media applications, including real-time broadcast of in-game performance parameters.

In an example implementation, the systems can be configured for sensor meshing of EMG and accelerometer data.

Many individuals who require physical therapy quit the training and exercise before they are ready. The danger is that they could be headed for another problem if the training and physical therapy is not completed. The example systems, methods and apparatus described herein can be implemented to assist an individual by providing a detailed assessment as to whether or not the individuals are favoring one limb over another or in the range of motion is not at full range yet.

In a non-limiting example, data collection through these devices can be aggregated and used across a number of individuals to establish standards of motion and movement range.

In all examples described herein, the data is collected and analyzed with the consent (where applicable) of the individuals involved.

As a non-limiting example, an injury can be muscle strain, post-surgery, other injury all of which can have a "gold standard." For example, an ACL injury versus a TKI injury, each can have its own "gold standard" as to what is considered acceptable range of motion and/or physiological change to be considered rehabilitated or not.

As a non-limiting example, the systems, methods and apparatus described herein can be made interactive. Example systems, methods and apparatus described herein can be configured to provide an analysis to answer the question "Are you symmetric?" regarding an individual.

In an example implementation, the systems can be configured to analyze data from measurements from the conformal sensor devices for training purposes to assess an athlete's motion. Data associated with the "templates" of ideal motion can be used for the comparison described hereinabove.

As a non-limiting example, the systems, methods and apparatus described herein can be used to determine how much better an individual is getting physiologically. According to the example systems, methods and apparatus described herein, a performance metric and data indicative of testing suites can be developed and stored and used for performance comparison. For example, The testing suites can be developed based on data collected in the performance of such idealized motion as the Football's Combine, which includes the desired motion and/or physiological data for an individual performing a 40 yard dash plus a 225 pound lift. The example systems, methods and apparatus can include a quantified comparison of the athlete's performance metric as compared to the data indicative of the Football's Combine testing suite.

As a non-limiting example, the systems, methods and apparatus described herein can be used to quantify the performance of an individual as compared to an idealized testing suites to determine which individuals are the "Paper Tigers", that is an individual that performs very strongly in a certain set of circumstances (such as in the weight room) but does not perform well in the field of play.

As a non-limiting example, the systems, methods and apparatus described herein can be used to provide media-based performance assessment for dispensing to an audience or other viewer of an event. For example, the throw count or other performance metrics for various players can be displayed or otherwise provided. Comparison between players, over the course of a season, can be derived using the example systems and methods and apparatus described herein. Syndicated data can be derived from and/or fed to a data stream (such as but not limited to game "stats").

In all examples described herein, the data is collected and analyzed with the consent (where applicable) of the individuals involved.

In an example implementation, the systems, methods and apparatus described herein can be worn during daily activity. Data analysis can be performed in real-time, at any point in time while the conformal sensor device is being worn, or data can be analyzed later after the conformal sensor device is removed. The data can be analyzed in aggregate.

The example, the systems, methods and apparatus described herein can be applied to analyze an individual's performance in such sports as tennis, golf, baseball, hockey, archery, fencing, weightlifting, swimming, gymnastics, horse racing (including thoroughbred racing), and track and fields (including running).

The example, the systems, methods and apparatus described herein can be applied to physical therapy, rehabilitation, athletic training, military and first responder training and assessment. For example, the systems, methods and apparatus described herein can be implemented for monitoring adherence to and/or improvement in physical therapy, rehabilitation, athletic training, military or first responder training. In another example, the systems, methods and apparatus described herein can be implemented for monitoring adherence to and/or improvement in clinical settings to treat, e.g., nervous system diseases including, but not limited to tremor analysis for those suffering from Parkinson's and the like.

The conformal sensor devices described herein can be attached to the body as a sticker or incorporated into form-fitting apparel including, but not limited to gloves, shirts, cuffs, pants, sporting apparel, shoes, socks, under garments, etc.

The example conformal sensor devices described herein include stretchable and/or flexible electronics having ultrathin form factors. These form factors are thin enough to be about as thin, or thinner, than a band-aid or even a temporary tattoo.

The example conformal sensor devices described herein can be configured for seamless tightly-coupled sensing that is transparent to the user individual and does not change, inhibit body movements or provide any indication that it is being worn. The close coupling provides proximate sensing that gives higher fidelity sensing and data than devices attached to or hanging from the body. The example conformal sensor devices described herein can be configured as ultra-light weight (about 10 g or less), ultrathin (about 2 mm or less), tightly coupled devices providing high capability for measurement and excellent data.

As a non-limiting example, the systems, methods and apparatus described herein can provide for communication of data and or the results of analysis of data to computing devices, including smartphones, tablets, slates, electronic books, laptops, or other computing devices, to facilitate external monitoring capabilities. The communication of data and or the results of analysis of data can tie the conformal sensor device into a variety of monitoring, diagnosis and even therapy delivery systems.

In an example implementation, throwing data, e.g., in sports, can be used for analyzing performance efficiency, monitoring fatigue, preventing injury, and calculating other athlete statistics. Example systems methods and apparatus herein can be worn in the field (e.g., on-field practice or game environments), and during sports activity, without impeding a subject's natural motion.

The example systems, methods, and apparatus herein facilitate the monitoring of both number of throws and throwing mechanics, using conformal electronics that are thin, stretchable, flexible, and directly coupled to the skin. In this way, the athletes' arm is uninhibited during practices and games, while the seamless conformal sensor devices facilitate complete, real-time monitoring of throws.

The example systems, methods, and apparatus herein provide conformal sensor devices having novel form factor (conformal, stretchable, and flexible) that also facilitate the collection of numerous throwing metrics using a single device.

The example conformal sensor devices herein include one or more sensor components, such as but not limited to triaxial accelerometers and/or gyroscopes, that can be implemented to measure the body mechanics during the throwing action and over a series of throwing sessions. The example conformal sensor devices facilitate flexible placement methods, and therefore so can be placed on any portion of the body, including the hand, wrist, forearm, upper arm, shoulder, or any other applicable body part. In other examples, the conformal sensor devices can be placed on any object coupled to or held by a body part (including a racket, baseball glove or mitt, or a hockey stick).

According to the principles described herein, the combination of the use of the example conformal sensor electronic devices and selective location on a body part can yield data indicative of a number of metrics, including: throw count, throw mechanics, throw type, throw efficiency, throw plane, peak arm acceleration, variability, and degradation over time, arm velocity, variability over time, power output, muscle activation, ball (or other object) velocity, ball (or other object) release time, and ball (or other object) release point.

The example conformal sensor devices according to the principles described herein are of very low mass/weight, and can be seamlessly worn on various parts of the body and individually optimized to collect data indicative of the metrics for each player.

In sports, such as but not limited to baseball, football, basketball, soccer, or hockey, the performance of the player (including pitchers and quarterbacks) is an important parameter to evaluate. These players can be very valuable to a team, especially if they perform at an elite level. People, such as but not limited to coaches, managers, trainers, and athletes, can be concerned about performance, throw count, throw mechanics, and injury prevention. According to the principles described herein, conformal sensor devices are provided that can be implemented to provide these metrics, in real-world the environment, such as during practices and games.

As a non-limiting example, fatigue awareness can be important to in sports with the increasing prevalence of "Tommy John" surgeries (or ulnar collateral ligament (UCL) reconstruction) in the elbow. According to an example system, method and apparatus herein, by measuring throw mechanics and count, customized insight can be provided to quantify a measure or performance of a player.

As a non-limiting example, algorithms and associated methods are provided to quantify, e.g., the number of pitches a player may require to warm up, or the number of throws before a change in performance is seen over the course of a game or a season.

For example, data collected on a subject (such as but not limited to an athlete) can be transmitted wirelessly to a smart device or the cloud for visualization and analysis, using custom-developed algorithms and associated methods.

The example systems, methods and apparatus herein can be applied to subjects such as but not limited to quarterbacks, baseball pitchers, fast-pitch softball pitchers, basketball payers, or hockey players. The subject can be of any age, such as but not limited to players of ages about 6 years to about 17 years, including players on elite teams (from high school to professional).

In non-limiting example implementation, an example conformal sensor device can be applied to a baseball pitcher prior to a game, e.g., to his or her forearm. The example conformal sensor device may either be coupled to the skin using a thin-film adhesive or be applied to the athlete's shirt using a fixation method. As well, the example conformal sensor device may be integrated onto an accessory garment/apparel, like an arm sleeve or wrap. As the pitcher starts to warm up, the coach or trainer can monitor the throws using a computing device coupled to the example conformal sensor device, e.g., a tablet or other smart device. The example conformal sensor device can be configured to stream data either continuously, at regular time intervals, or intermittently, including after each inning or after each game, to the computing device for analysis. The coach/trainer may make corrections, changes, or recommendations to the pitcher during or after the game to improve performance or prevent injury.

In a non-limiting example implementation, the example conformal sensor device can be used to quantify consistency of movement, e.g., of a golf swing, baseball swing, basketball free-throw, soccer kick, etc.

In a non-limiting example implementation, the example conformal sensor device can be used for movement tracking, including the acceleration of a body part (e.g., a leg kick in swimming, football or soccer, an arm in throwing, etc.)

In a non-limiting example implementation, the example conformal sensor device can be used for movement counting, including repetition counting (of e.g., pitches, lifting, number of punches thrown/landed in a boxing match, or other activity.

Figure 13:
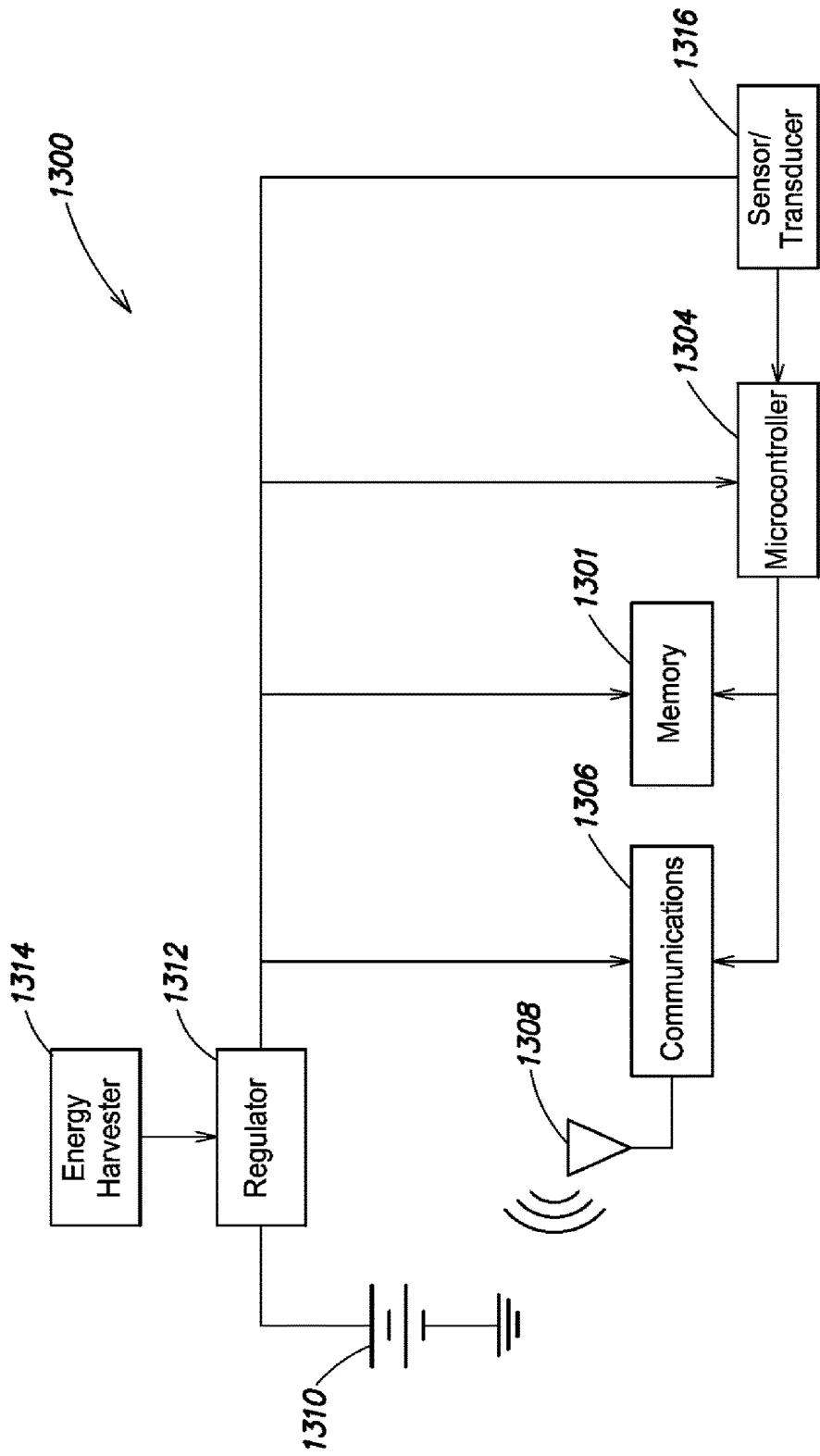
FIG. 13 shows a block diagram of an example architecture of an example conformal sensor system, according to the principles herein.

FIG. 13 shows a block diagram of an example system-level architecture 1300 of an example conformal sensor system according to the principles herein. The example system includes a memory 1302, a microcontroller 1304 (including at least one processing unit), a communications component 1306 (including an antenna 1308), a power supply 1310 (i.e., a battery unit), a charge regulator 1312 coupled with an energy harvester 1314, and a sensor/transducer component 1316. In a non-limiting example, the sensor/transducer component 1316 includes motion sensor platform electronics for performing at least one of an accelerometry measurements and a muscle activation measurement. In some examples, the example conformal sensor system may include at least one other type of sensor component. In the example of FIG. 13, the communications component 1306 can include Bluetooth® communication or other wireless communication protocols and standards, at least one low-power micro-controller unit for controlling the recording at least one of an accelerometry measurement and a muscle activation measurement, and any other data associated with any at least one other physiological parameter measured. In an example, there can be a respective micro-controller 1304 for controlling each different type of sensor component for performing a measurement.

Figure 14:
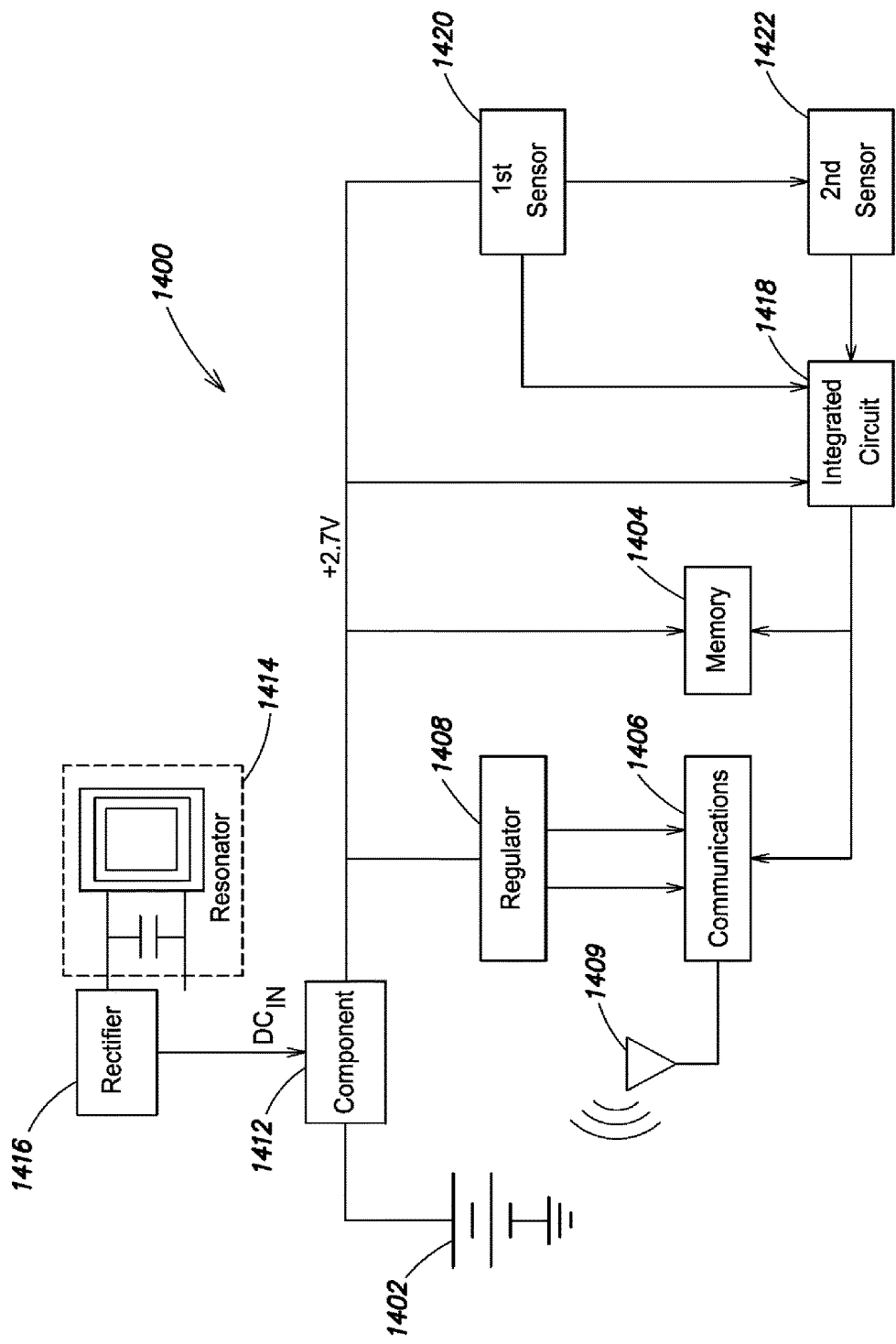
FIG. 14 shows non-limiting examples of components of an example conformal motion sensor platform, according to the principles herein.

FIG. 14 shows non-limiting examples components of an example motion sensor platform 1400. In the example of FIG. 14, the motion sensor platform incorporates an onboard battery unit 1402 (e.g., supplying about 2.7V), a coupled with a memory 1404 (e.g., a 32 Mbyte flash memory), and a communication component 1406 (e.g., a Bluetooth®/BTLE communication unit) coupled with an output regulator 1408, and an antenna 1409. The battery unit 1402 may be coupled to at least one other component 1412, the at least one other component 1412 being an energy harvester, a battery charger, and/or a regulator. The motion sensor platform may be coupled with a resonator 1414 (such as but not limited to a 13.56 MHz resonator) and full-wave rectifier 1416. The motion sensor platform 1400 includes an integrated circuit component 1418 that includes a microcontroller, a Bluetooth®/BTLE stack on-chip, and firmware including instructions for the implementation of the conformal sensor system. The platform includes a first sensor component 1420 and a second sensor component 1422. In an example, the first sensor component 1420 can be configured to include a 3-axis accelerometer, at least 3 sensitivity settings, and a digital output. In an example, the second sensor component 1422 can be configured to include EMG sensing, EMG electrodes, and a digital output. The example conformal motion sensor platform can include a low-power micro-controller unit for accelerometry and a low-power micro-controller for electrophysiological recordings. In some examples, the functions of a given component of the system, such as but not limited to the accelerometry, EMG, or other physiological measuring component, may be divided across one or more microcontrollers. The lines leading from the energy harvester/battery charger/regulator to the other components highlight modular design where different sensors (such as but not limited to EMG, EEG, EKG electrodes) can be used with similar set of microcontrollers, communications, and/or memory modules.

Figure 15:
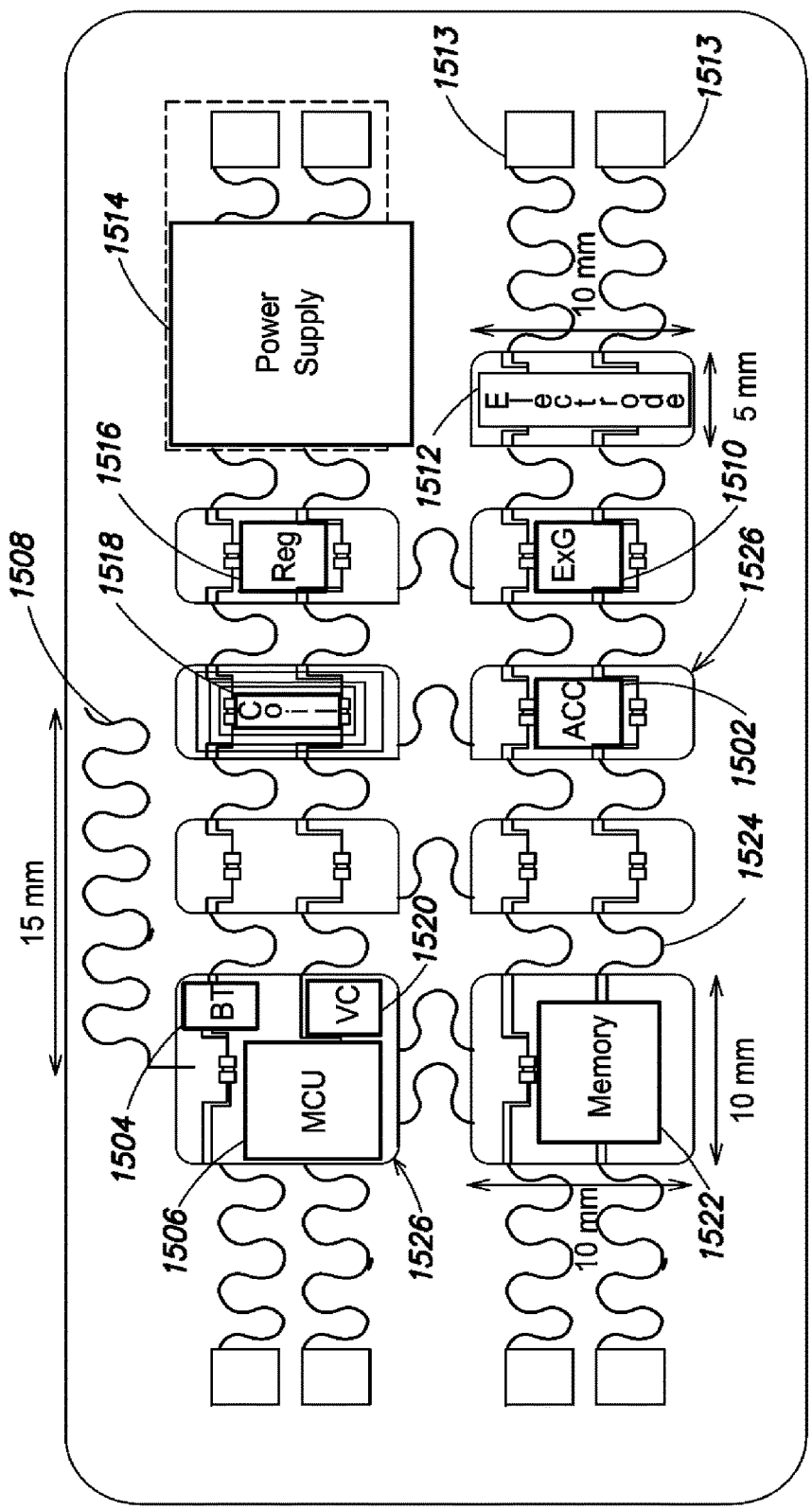
FIG. 15 shows an example architecture of an example conformal sensor system, according to the principles herein.

FIG. 15 shows an example schematic drawing of the mechanical layout and system-level architecture of an example conformal sensor system configured as a rechargeable patch. The example conformal sensor system electronics technology can be designed and implemented with various mechanical and electrical layouts for multifunctional platforms. The devices including the conformal electronics technology integrate stretchable form factors using designs embedded in polymeric layers. These can be formulated to protect the circuits from strain and to achieve mechanical flexibility in an ultra-thin cross-section. For example, the device can be configured with thicknesses on the order of about 1 mm on average. In other examples, the patch can be configured with thinner or thicker cross-sectional dimensions. The device architecture can include a reusable module containing surface-mount technology (SMT) components, including accelerometer 1502, wireless communication 1504, microcontroller 1506, antenna 1508 (such as but not limited to a stretchable monopole antenna), and conformal electrode arrays 1510 and 1512 for sensing, e.g., EMG, EEG and EKG signals, and an electrode connector 1513. T. The conformal electrode arrays can be disposable 1510 and 1512. The example device can also include a power supply 1514 (such as but not limited to a LiPo Battery of power 2 mA-Hr or 10 mA-Hr), a regulator 1516, a power transfer coil (such as but not limited to a 0.125 oz Cu coil with 1.5/2 mil trace/space ratio), a voltage controller 1520 and a memory 1522.

As shown in the example of FIG. 15, the components of the example conformal sensor system are configured as device islands interconnected by stretchable interconnects 1524. The components of the example conformal sensor system may be sensor components or other components, including electrodes, electrode connectors, or any other example component according to the principles described herein. Stretchable interconnects 1524 can be electrically conductive to facilitate electrical communication between the components, or electrically non-conductive to assist in maintaining a desired overall form factor or relative aspect ratio of the overall conformation of the conformal sensor device during or after being subjected to deformation forces, such as but not limited to extension, compressive and/or torsional forces. The example of FIG. 15 also shows the differing shapes and aspect ratios of the island bases 1526 that the components of the example conformal sensor system can be disposed on, or otherwise coupled to, to provide the device islands.

FIG. 16A shows an example implementation of a conformal sensor system formed as a conformal patch with sub-components. The example conformal sensor system includes disposable electrodes 1602, a re-usable connector 1604, and a rechargeable conformal sensor unit 1606 formed as a conformal patch. The example rechargeable conformal sensor unit can be configured to include at least one other component 1608 such as but not limited to a battery, a microprocessor, a memory, wireless communication, and/or passive circuitry. As a non-limiting example, the average thickness of the reusable patch can be about 1 mm thick and the lateral dimensions can be about 2 cm by about 10 cm. In other examples, the patch can be configured to have other dimensions, form factors, and/or aspect ratios (e.g., thinner, thicker, wider, narrower, or many other variations).

FIG. 16B shows another example implementation of a conformal sensor system formed as a conformal sensor patch with sub-components. The example conformal sensor system includes example EMG electrodes 1642 disposed on an ultrathin sticker 1644 and example conformal sensor system disposed on a skin adhesive 1646. The example EMG electrodes are coupled to the example conformal sensor system via an electrode connector 1648. The example rechargeable conformal sensor unit can be configured to include at least one of a battery, a microprocessor, a memory, wireless communication, and passive circuitry. In this example, the average thickness of the reusable patch can be about 1 mm thick and the dimensions can be about 2 cm by about 10 cm. In other examples, the patch can be configured to have other dimensions, form factors, and/or aspect ratios (e.g., thinner, thicker, wider, narrower, or many other variations).

FIG. 16C shows an example implementation of a conformal sensor system 1662 that is disposed on a body part or other object. In this example, the body part is a forearm. The conformal sensor system 1662 can include at least one accelerometry component and any other sensor component described herein. As described in greater detail below, the conformal sensor patch can be used to provide continuous feedback on muscle activity, body part motion (based on acceleration and/or force applied measurement), and/or electrophysiological measurements.

Figure 17A:
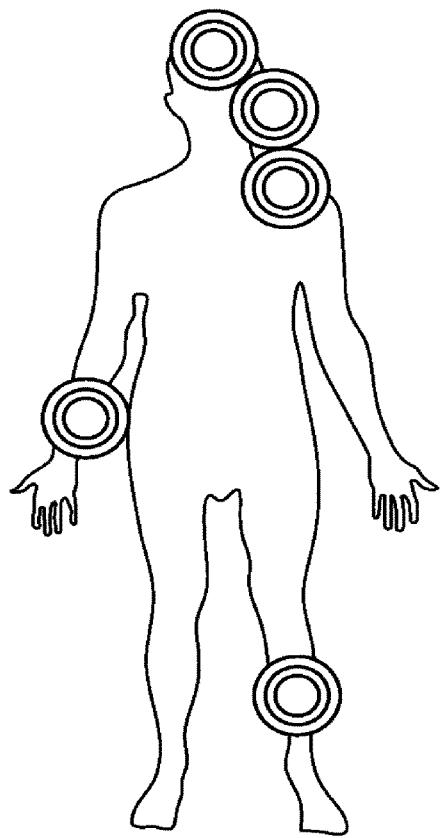
FIG. 17A shows examples of placement of the example conformal sensor system on a human body, according to the principles herein.

FIG. 17A shows examples of placement of the example conformal sensor systems. As shown in the example of FIG. 17A, the conformal sensor systems can be placed at various locations on the body. In various example implementations, the conformal sensor systems can be placed at various locations on the body to measure the signal to noise ratio associated with each sensor/location combination. The results of analysis of the data obtained from the measurements at each placement position can be used to determine an optimal location for obtaining a desirable signal to noise ratio.

Figure 17B:
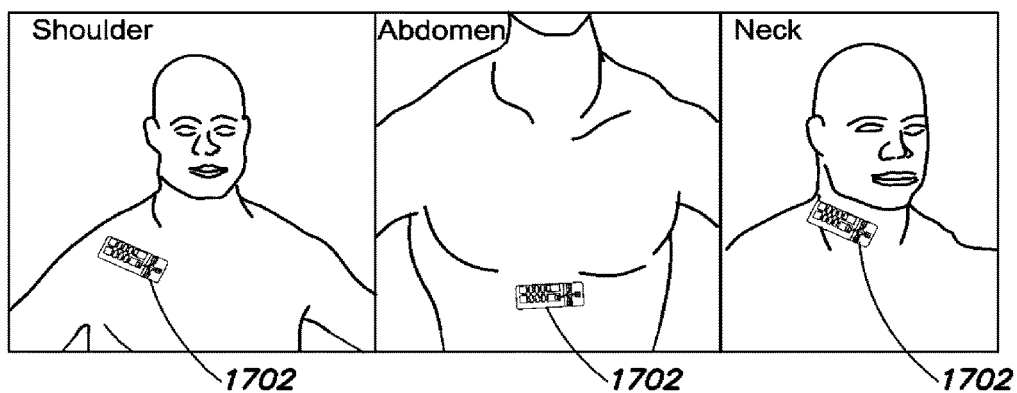
FIG. 17B shows example images of a conformal sensor system disposed on a body part, according to the principles herein.

FIG. 17B shows example images of a human torso and neck showing different anatomical locations where the example conformal sensor system 1702 can be disposed for measurements. In other examples, the example conformal sensor systems can be disposed proximate to the muscles of the arms.

The example conformal electronics technology herein can be designed and implemented with various mechanical and electrical layouts for multifunctional platforms. The example devices including the conformal electronics technology can be integrated with various stretchable form factors using designs embedded in polymeric layers. These can be formulated to protect the circuits from strain and to achieve mechanical flexibility with ultra-thin profiles, such as but not limited to thicknesses of about 1 mm on average. In other examples, the patch can be configured with thinner or thicker cross-sectional dimensions. The example device architecture can include a reusable module containing surface-mount technology (SMT) components, including accelerometer, wireless communication, microcontroller, antenna, coupled with disposable conformal electrode arrays for sensing EMG or other electrical measurements (such as but not limited to NCS, electroencephalogram (EEG) and electrocardiogram (EKG) signals).

Processor-executable instructions development (including software, algorithms, firmware) can be configured to be specific for each platform using predicate algorithms as the basis of the signal processing. Filters and sampling rates can be tuned and tested on rigid evaluation boards and then implemented with flexible designs. The example conformal sensor systems and conformal electrodes according to the principles described herein can be used, based on implementation of the processor-executable instructions, for monitoring, e.g., body motion and/or muscle activity at various locations on the body, and/or analysis of data indicative of measurements from the monitoring Non-limiting examples of sensor component measurements that can be made according to the principles described herein are as follows.
1. Precision and reproducibility of sensor measurement output can be determined based on;
    a. Body motion—X, Y, Z axis acceleration waveform in G's
    b. Muscle motion—muscle motion ON/OFF and ON-to-ON time
2. Optimal placement for each sensor can be determined for maximum signal detection.
3. Optimal co-location placement for two or more of the sensors can be determined in a similar manner.

The example conformal sensor systems and conformal electrodes according to the principles described herein can be used to measure body motion and/or muscle activity, heart rate, electrical activity, temperature, hydration level, neural activity, conductance, and/or pressure, with acceptable precision. Acceptable precision can be defined as operationalized as a high correlation (such as but not limited to r≥0.8) of these sensors with standard reference measurements of:

| Accelerometry | Such as but not limited to Shimmer3 ® base module or similar or an external image-based body monitoring |
| --- | --- |
| Electromyogram | Grass P511AC Amplifier (Grass Technologies, West Warwick, RI, USA)[1], or |
| Electrocardiogram | MAC 3500 12 Lead ECG Analysis System (GE Healthcare, AZ, USA)1, or similar |

(1) An optimal placement on the body for each conformal sensor system can be determined to yield high-quality, precise and reliable measurement.
(2) There can be at least one placement on the body in which the example conformal sensor systems and conformal electrodes can be placed to yield precise and reliable measurements.

Non-limiting examples of types of measurements that can be made are as follows.
Standard reference measurements can be taken while conformal sensor system is mounted on a portion of a subject. Each condition can be repeated to generate reproducibility data.
Body and Muscle Motion:
Subjects can be measured on standard references (3 axis accelerometer and/or EMG) while wearing the example conformal sensor system. The example conformal sensor system can be placed in selected body placement locations, including; inside wrist, calf, front left shoulder, rear left shoulder, left neck below the ear and forehead (e.g., as shown in FIGS. 17A-17B). Subjects can be measured for a period of time while performing a sequence of activities/movements, e.g., sit down, walk, hand movements, athletic activity, physical therapy movements, or any other movement described below.

All example conformal sensor system and reference measurements can be analyzed to provide information indicative of the desired performance of the individual, including the physical condition of the subject, the efficacy of a treatment or therapy being performed on the subject, the subject's readiness for physical activity or exertion, or proper physical condition for a sport or other exercise.

Figure 18:
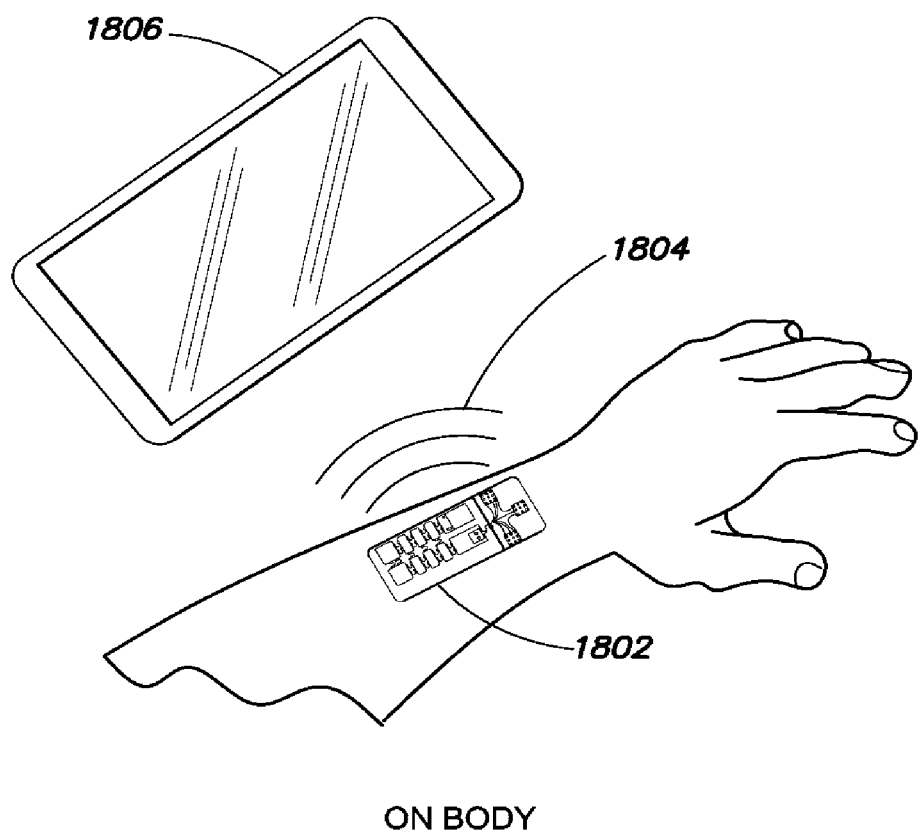
FIGS. 18 and 19 show different examples of a communication protocol, according to the principles herein.
Figure 19:
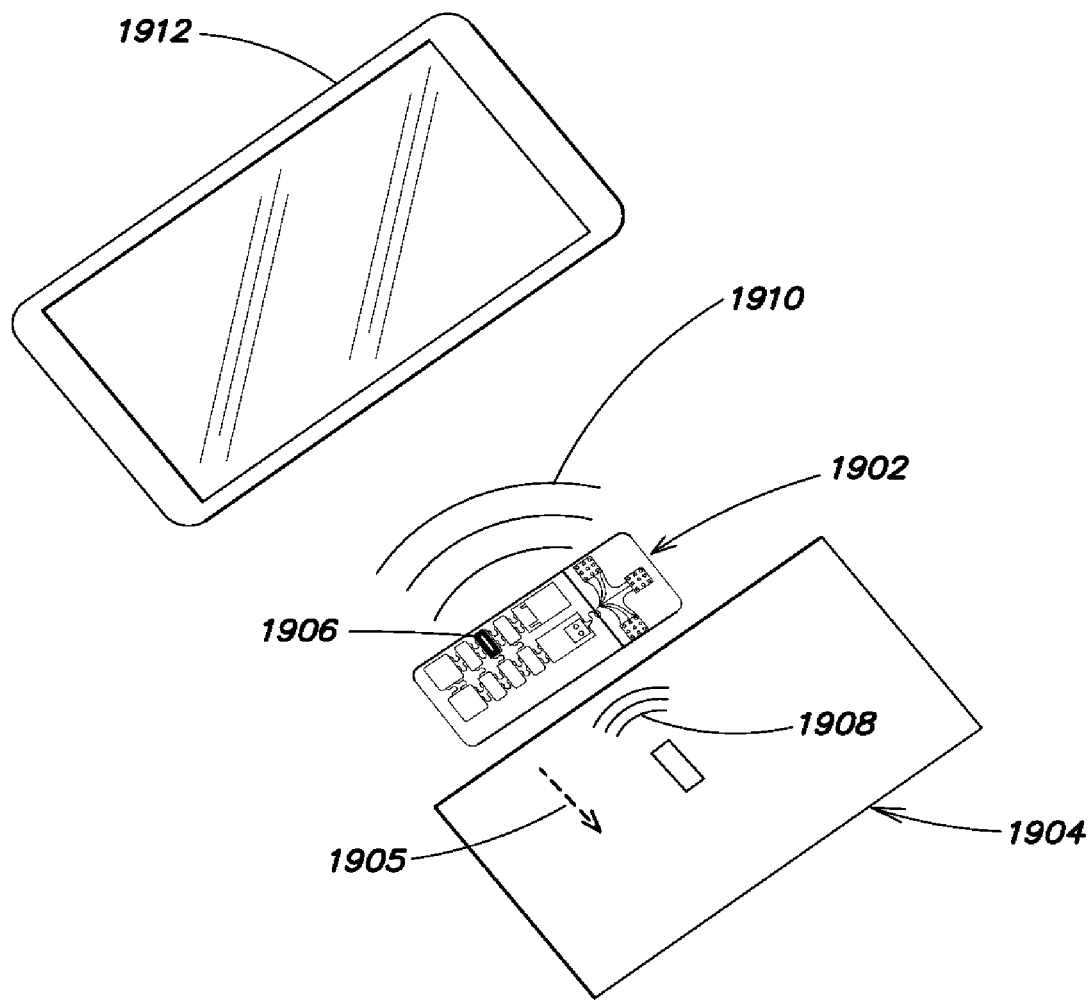

Example system, methods and apparatus are provided herein can be used to estimate the sensitivity, specificity and positive and negative predictive values of algorithm from the conformal sensor systems to predict, for example but not limited to selected metrics of the efficacy of a treatment or therapy being performed on the subject. The feasibility or acceptability of subjects wearing the conformal sensor systems can be monitored. Subjects can be monitored while wearing the conformal sensor systems disposed on a body part or other object for a period of time (e.g., time on the order of minutes, an hour, or a number of hours, while at rest or while carrying out a series of motions, activities and/or tasks FIGS. 18 and 19 shows different examples of the communication protocol that can be applied to an example conformal sensor system 1802 described herein. In the example of FIG. 18, a signal from the example conformal sensor system 1802 can be transmitted to an external memory or other storage device, a network, and/or an off-board computing device. The signal can include an amount of data indicative of one or more measurements performed by the example conformal sensor system and/or analysis results from an analysis of the data. In the example of FIG. 18, the example conformal sensor system is configured to use, e.g., a Bluetooth® low energy (BLTE) communications link 1804 for on-body or on-object transmission to a Bluetooth®/BLTE-enabled device 1806. In an example implementation, small amounts of data to be transferred at low data rates, including current peak accelerometry measure (e.g., g value) with timestamp (or other metadata) and/or EMG activity (either turned ON or OFF) with timestamp (or other metadata). Non-limiting examples of the other metatada includes location (e.g., using GPS), ambient air temperature, wind speed, or other environmental or weather condition. In another example accelerometer data can be used to determine values of energy over time. In other examples, data representative of physiological parameters or other measures can be transferred with timestamp or other metadata. FIG. 19 shows an example implementation where the signal is transmitted with the example conformal sensor system 1902 couples to a charging platform 1904 at a designated location 1905. The example conformal sensor system 1902 includes a power transfer coil 1906 to facilitate a charging with a charging coil and field 1908. Bluetooth® low energy (BLTE) communications link 1910 for on-body or on-object transmission to a Bluetooth®/BLTE-enabled device 1912. The signal can be transmitted to an external memory or other storage device, a network, and/or an off-board computing device. In the example of FIG. 19, the example conformal sensor system 1902 is configured to use, e.g., Bluetooth® enhanced data rate (BT EDR) transmissions, at much higher data rates than BTLE, to transmit the data signal. For example, the data signal can include raw accelerometery data (X, Y, Z) with timestamp and/or EMG filtered waveform with timestamp. In an example, the conformal sensor system can be maintain disposed on or otherwise coupled to a charging platform while performing the BT EDR transmissions, based on the high power requirements.

Figure 20:
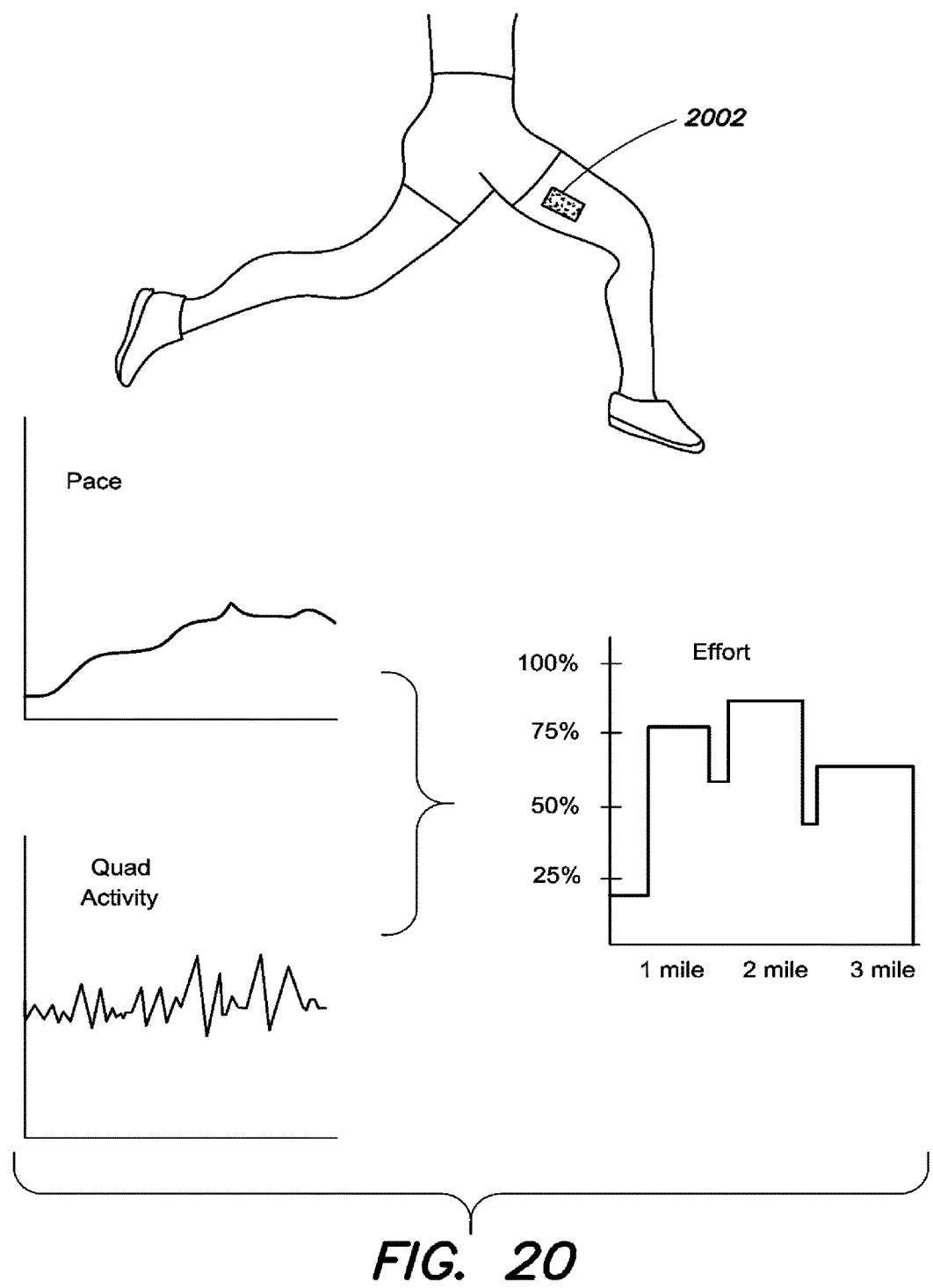
FIG. 20 shows an example of use of an example conformal sensor system for quantifying a measure of performance as a muscle activity tracker, according to the principles herein.

FIG. 20 shows an example of use of the example conformal sensor systems for quantifying a measure of performance as a muscle activity tracker. Muscle activity and motion as an indicator of activity level. The example conformal sensor system can be placed on working muscles of a subject. In this non-limiting example, the conformal sensor system 2002 can be disposed on a portion of the thigh as shown in FIG. 20, or on any other body part whose performance is to be quantified. Measurements of the example conformal sensor system can be used to indicate activity level and effort of the subject. As shown in FIG. 20, the example conformal sensor system can be disposed on a subject's body part involved in the motion (such as but not limited to a runner's quadriceps). The example conformal sensor system can be coupled to a display to show output graphs showing, e.g., a runner's pace or gait (through accelerometer measurements) and quadricep activity (through EMG measurements). In this example, data indicative of the accelerometer and the EMG measurements may be used to indicate the athlete's activity level through an accurate estimator of distance walked/ran, amount of effort made. Analysis of the data can be used in sports to track athletes' activity levels on and off the field/courts, and also on medical circumstances where the patient's activity level is determined as a monitor, e.g., of recovery from heart surgery, diabetes patients, patients in need of losing weigh, etc. In another example analysis, a combination of the data indicative of the accelerometer and the EMG measurements can be used to provide information for an effort chart, where the runner can view calculated effort over a single run or multiple runs. This can be used to evaluate and improve performance over time. In some examples, two or more such conformal sensor systems can be mounted on or otherwise coupled to portions of the body or other object to provide measurements that can be analyzed to determine body/object kinematics and dynamics.

Figure 21:
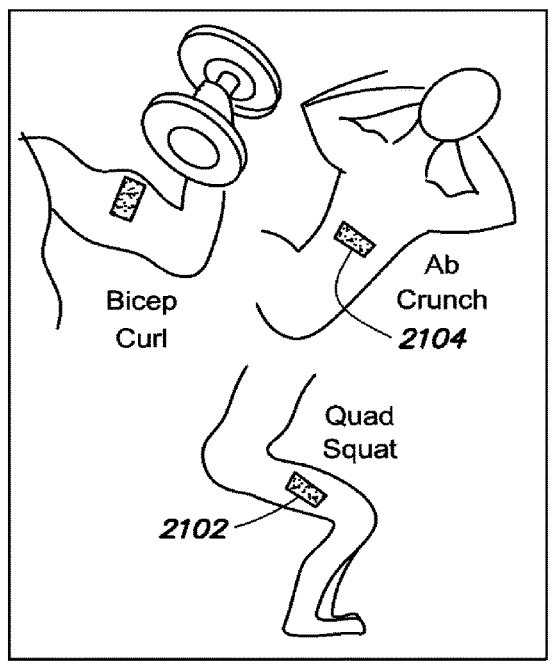
FIG. 21 shows an example of use of the example conformal sensor systems for quantifying a measure of performance as a strength training program tracker and/or a personal coach, according to the principles herein.
Figure 21:
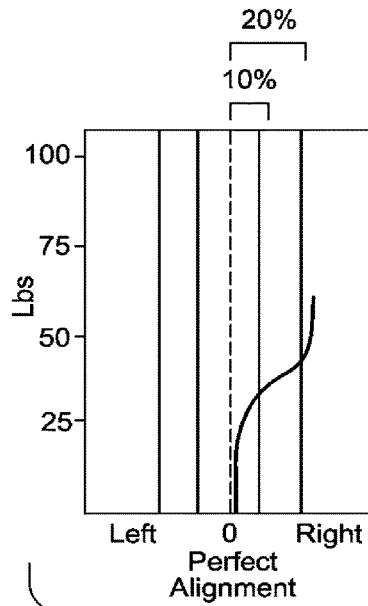
Figure 21:
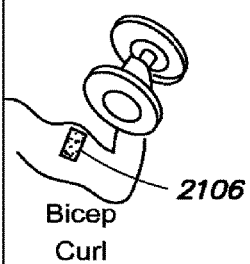
Figure 21:
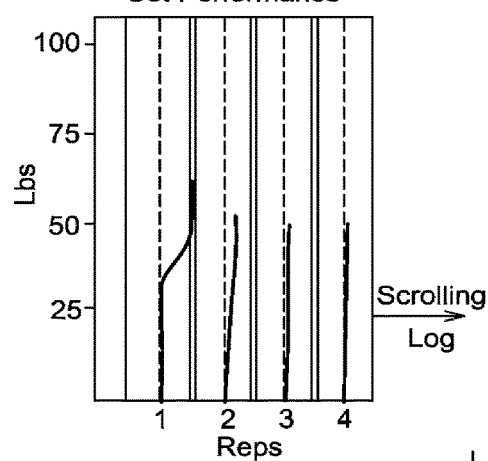
Figure 21:
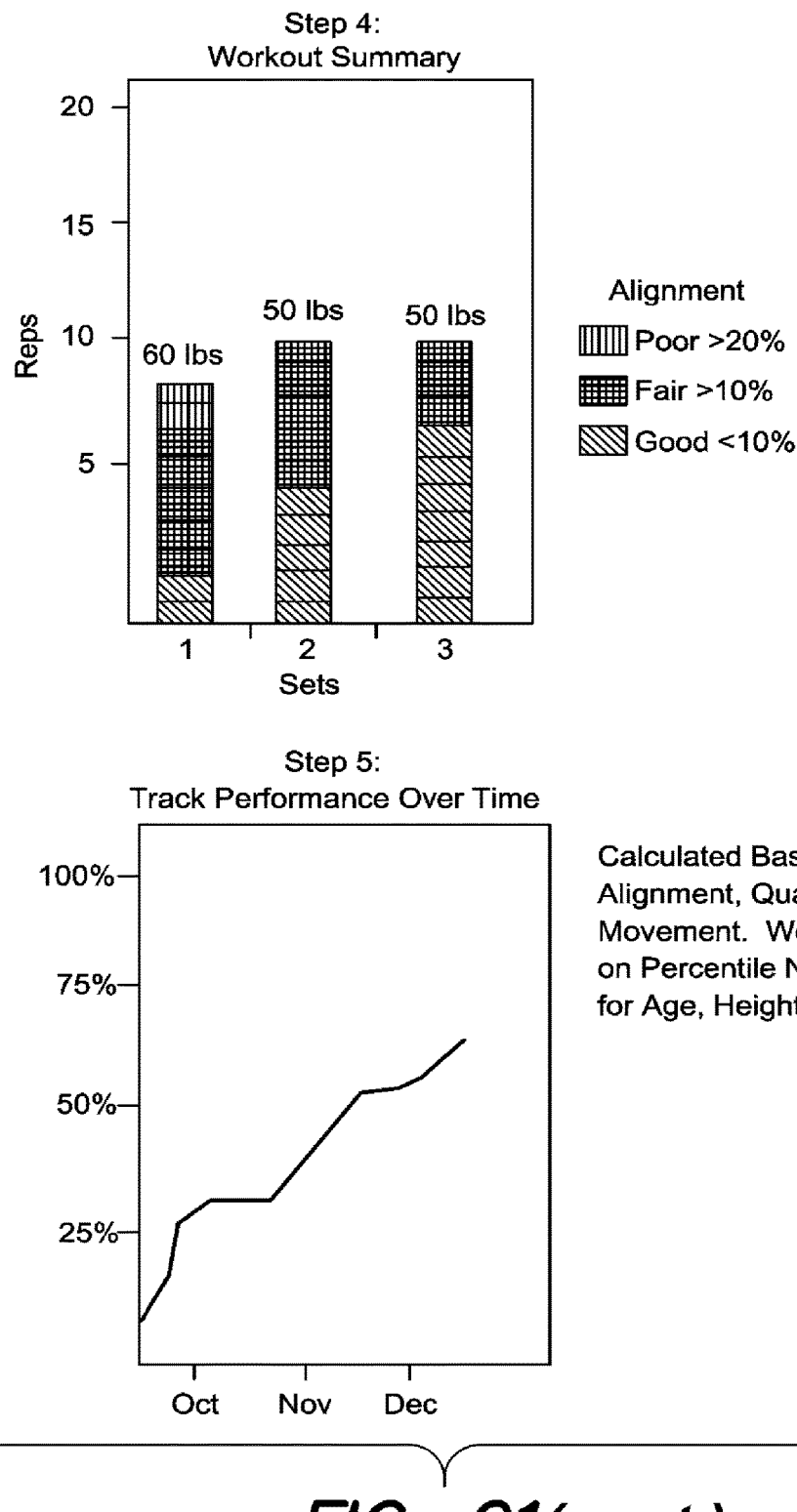

FIG. 21 shows an example of use of the example conformal sensor systems for quantifying a measure of performance as a strength training program tracker and/or a personal coach. The example conformal sensor can be disposed on or otherwise coupled to any body part being monitored. In this non-limiting example, the conformal sensor system can be disposed on a portion of the thigh 2102, a torso 2104, or an upper arm 2106, as shown in FIG. 21, or on any other body part whose performance is to be quantified. The measures of muscle activity can be used as means to provide baseline activation levels of the subject's strength, e.g., through measures of magnitude of motion. A measurement using an EMG component can be used for detection of different muscle activities. For example, in an example implementation, it is possible to detect differences in the amount of effort being put on a muscle and/or muscle group when a subject is performing a similar muscular activity, e.g., pulling weight, or running on a treadmill).

FIG. 21 shows five non-limiting example application screens (on example displays) for various phases of an example strength training, to show the various examples of performance measures (set performance, work summary, and track performance over time) that can be quantified according to the principles described herein. The example application screens can be used by, e.g., athlete or trainer to track quantity of weight, repetitions, and sets against performance. The display of the example application screens, based on analysis of measures of the example conformal sensor system, can replace paper charts typically kept for strength training program tracking.

In FIG. 21, the example step 1 shows an example of a display coupled to the example conformal sensor system for user selection from a selection of icons, the muscle and exercise associated with the conformal sensor placement on the subject's body. In example step 2, a graphic representation on the display can be used to provide feedback of body part alignment during exercise or other activity, e.g., in real-time or at different or regular time intervals, or at the subject's demand. On the example graph, a value of "0" is used as an indicator of perfect alignment or alignment within a specified range from perfect alignment. The subject shifts out of axis alignment to the left or to the right, can be indicated on the display by the straightness of a line. The example in FIG. 21 also shows on the display the subject's bias to the right, and out of alignment, at the peak of the exercise by over 20%. In this example, the user can take the feedback and adjust exercise form and weight based on inspection of the display or from recommendations displayed on the display. In the example of step 3, the subject is shown on the display a view of his/her weight lift set performance over a series of repetitions. This example shows analysis results indicating improved alignment with reduced weight, where the user improves his/her performance during sets with lower weights. In the example of step 4, the display can be configured to show a graphic of a summary view of the subject's repetitions and sets. This example shows a summary information indicative of quantity of repetitions, type of weight used, number of sets, and alignment factor for each repetition. As a non-limiting example, the alignment can be quantified as a percentage based. For example, a value of less than about 10% from perfect alignment may be categorized as "GOOD", a value of greater than about 10% from perfect alignment may be categorized as "FAIR", and a value of greater than about 20% from perfect alignment may be categorized as "POOR".

In the example of step 5, the display can be configured to show a view of subject's performance over time by percentage. The analysis (including calculations) can be based on data indicative of alignment, quality of movement, weight based on percentile norms for age, height, weight. An algorithm and associated method can be developed using accelerometer and EMG data in addition to values indicative of norms (such as but not limited to example published norms).

Figure 22:
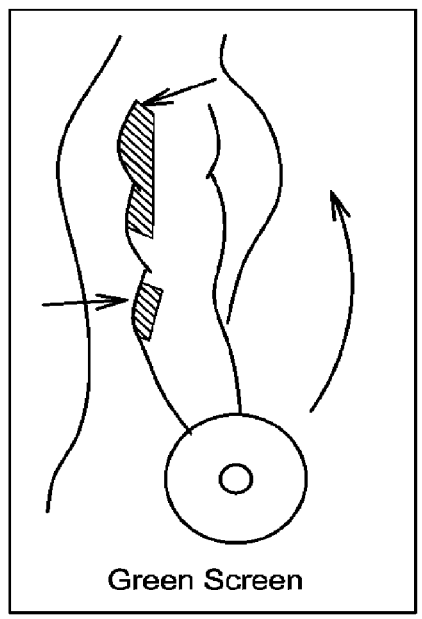
FIG. 22 shows an example of use of the example conformal sensor systems for quantifying a measure of performance for strength training feedback, according to the principles herein.
Figure 22:
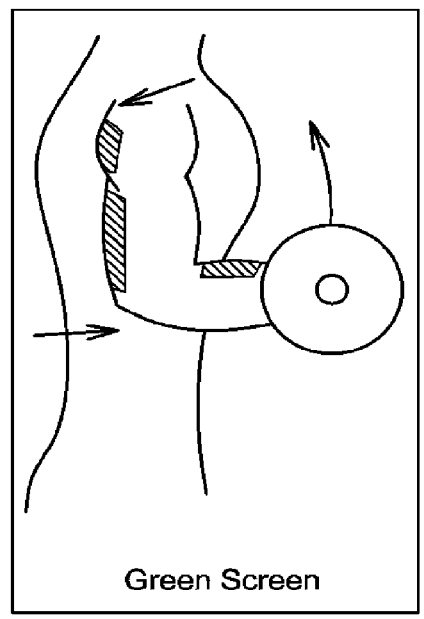
Figure 22:
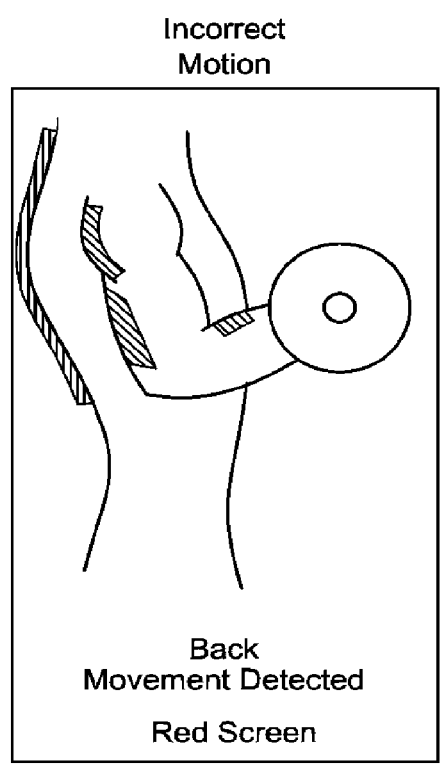

FIG. 22 shows an example of use of the example conformal sensor systems for quantifying a measure of performance for strength training feedback. In this non-limiting example, the conformal sensor system can be disposed on a portion of an upper arm, a lower arm, and/or a shoulder. In this example, a display is configured to provide user interface screens shown within a software application for motion and/or muscle activity. The system can be configured to provide indications of results to a user. For example, the user may be displayed a green screen when the performance measure indicates that the muscle activity and/or motion are ideal. The system can be configured to change a screen to red and/or sends an auditory feedback to the user, where the performance measure quantified based on the conformal sensor measurements indicates incorrect user motion and/or muscle activity is detected.

FIGS. 23A, 23B and 23C show an example of use of the example conformal sensor systems for quantifying a measure of performance for user feedback. The feedback can be provided in real-time, at different time intervals, and/or at user demand. In FIG. 23A, the system is configured to provide an audible feedback to the user through smart device in recommendations, tips, motivational statements, as well as tones, music, and/or beeps. In this non-limiting example, the conformal sensor system 2302 can be disposed on a portion of an upper arm, or any other body part. In FIG. 23B, the system is configured to provide haptic feedback (including vibrations and/or pulses) to the user, felt in the area of the body coupled to the conformal sensor system, and/or on a computing device. One or more miniature actuators can be incorporated into the sensor electronics to provide the haptic feedback. In FIG. 23C, the system is configured to provide visual feedback, such as displayed on conformal sensor system or on a computing device. Non-limiting examples of visual feedback include blinking LEDs, sequence array of LEDs, and/or colored LEDs. The example LEDs can be incorporated into conformal sensor electronics.

Table I lists various non-limiting example of the differing types of performance that can be quantified based on at least one measurement of a sensor component of a conformal sensor device according to the principles described herein. In the different example implementations, the sensor component can include at least one of an accelerometer and an EMG component.

TABLE I

| Example Performance | Description of Example Implementation To Determine Example Performance | Accelerometer | EMG |
|---|---|---|---|
| Pattern Matching | Corrective movement patterns via pattern matching with desired motion patterns | x | |
| Baseline Symmetry | Muscle activity and motion as means to baseline symmetry (diagnosis of possible need to balance flexor/extensor symmetry - prevention of musculoskeletal injuries caused by imbalances). Muscles fired during a motion (e.g. walking) are utilized in different ways depending on the stage of the walking. Flexor muscles and extensor muscles perform at their best when there is balance in the range and exert of muscle activity. An unbalanced flexor/extensor ratio may result in stress being put on tendons and ligaments, and may result in injuries - this unbalanced muscle activity ratio can be detected by the sensors and corrected through stretch, and strengthening exercises. | x | x |

TABLE I-continued

| Example Performance | Description of Example Implementation To Determine Example Performance | Accelerometer | EMG |
|---|---|---|---|
| Muscle activity tracking | Muscle activity and motion as an indicator of activity level. Patient's activity level (e.g., patients in need of losing weight, etc.) | x | x |
| Sleep tracking | Muscle activity and motion as an indicator of quality of sleep. Motion may detect respiratory rhythms, amount of movement in bed and how many times the person wakes up/stands up to go to the bathroom, or get water. Muscle activity may indicate relaxation level and indicate bruxism. Delayed feedback may be used to assist individuals to implement new sleeping habits to maximize rest and recovery. Other example measures can be used for analysis, including skin conductivity and respiratory rate sensing | x | x |
| Fatigue indicator | Muscle activity evolution through the length of physical exerts - detection of desired zones of performance and zones indicating risk of muscular injuries and of ligament/tendon injuries. Indicators of decrease in the quality of muscle response are indicators of higher risk for injuries, especially in the joints, due to stress put on the ligaments and tendons due to lack of quality on the muscle activity. Differences in EMG frequency and amplitude are indicators of muscle conditions throughout a period of time - it's possible to determine fatigue levels and exhaustion. This is a very powerful indicator for possible causes of injuries - and may assist on injury prevention. | | X |
| Dynamic stretching | Measure of muscle tension during dynamic stretching - regulation of beneficial levels of stretching - optimizing injury prevention or reduction. Dynamic stretching utilizes momentum as the main benefit for the implementation of stretch - many times dynamic stretching is mistaken for warming-up. The EMG sensors and accelerometers data can be combined to provide data indicating differences between warm-ups and dynamic stretching. Moreover, the system may detect desired ranges and motion patterns for each athlete based on muscle response and activity - maximizing the quality of stretching, and minimizing injuries. | x | x |
| Pattern Matching Individual | Reproducibility of an individual's form/movement or compare with desired motion pattern | x | |
| Pattern Matching Professional | Confirming user movement patterns with those of professionals (such as but not limited to swing in golf/putting, face-off in hockey, swing and pitch in baseball, punt in football, corner kicks in soccer, etc.). This example allows a user to compare his/her movement or performance with, e.g., an athlete or other famous person, with user/athlete/person consent. The comparison can be performed based on captured movement patterns of the specified athlete or other famous person. | x | |
| Balance/ Symmetry | Movement/strength comparison between opposite limbs and muscle groups | x | x |
| Movement magnitude | Motion as means to baseline accelerations and overall gait/movement (magnitude). Crossing data from EMG and accelerometers it is possible to determine movement acceleration and gait to determine desired zones of performance for specific sport moves, desired ranges of motion | x | x |
| Strength training | Muscle activity as means to baseline activation levels of strength (magnitude). EMG sensors detect different muscle activity - it is possible to detect differences in the amount of effort being put on a muscle/muscle group when performing a similar muscular activity (e.g. pulling weight, or running on a treadmill). | | x |
| Grip intensity | Muscle activity level measurement for desired grip intensity. Assessment of amount of muscle activity in the forearm indicating grip pressure - data is compared to motion patterns. Reaction time testing. This data is beneficial for monitoring performance in sports utilizing racquets, bats, clubs. In an example, the feedback can be provided in real time, on user demand, or at different time intervals, for adjustments to be made. Such tool may assist on putting | | x |

TABLE I-continued

| Example Performance | Description of Example Implementation To Determine Example Performance | Accelerometer | EMG |
|---|---|---|---|
| | consistency, quality and speed of a golf swing, and the ability to perform small adjustments on the bat trajectory in baseball, among other uses. The activity can be performed using equipment such as but not limited to, golf club, baseball bat, tennis racquet, basketball, etc. | | |
| Muscle performance | Muscle activity/quality of muscle activation - improvement of muscle readiness for faster muscular response time. It's possible to assess the quality of muscular activity and to find desired levels of performance for faster muscle response and reaction times. This may assist athletes to determine beneficial stretching and warm up exercises, or even self-regulatory techniques prior to specific sport tasks (like pitching, face-offs, defending as a goalie . . . ). The system may provide feedback to athletes when they need to adjust muscle conditions to improve performance. | | x |
| Muscle activity tracking | Muscle activity and motion as an indicator of activity level. Accelerometer and EMG may be used to indicate the athlete's activity level (accurate estimator of distance walked/ran, amount of effort made . . . ) this can be used in sports to track athletes' activity levels on and off the field/courts, and also on medical circumstances where it is beneficial to determine the patient's activity level (e.g. recovery from heart surgery, diabetes patients, patients in need of losing weight . . . ). | x | x |
| Kinetic link | Detection of kinetic link - the order in which muscles or muscle groups are being fired - assisting on desired patterns to improve movement speed and accuracy. Accelerometer and two or more EMG sensors can be used to detect the order in which muscles are being fired and provide feedback on differences between desired patterns and the pattern being performed by the athlete. In quick motions (like a golf swing or a pitch) the feedback is provided with a minimum delay, in order to assist the athlete to analyze and make adjustments in the next movement they are performing - feedback can be on time for motions that allow so (like golf putting, or a draw, anchoring and release in competitive archery). | x | x |
| Pattern Matching | Relearning movement patterns for people who have undergone surgeries and amputations. | x | |
| Readiness to return to play | Muscle activity and motion as an indicator of readiness for return to work, play or other post injury. Possible to baseline user motion (activation, acceleration and range) and muscle activity to utilize as a point of comparison throughout rehabilitation. A baseline measure can be used. Patients who are recovering from an injury/surgery are assessed for the quality of the movement they are able to perform at different stages of their recovery - desired patterns for each stage are displayed and the patient tries to conform to the desired pattern. Moreover, the quality of the muscle activation is analyzed to determine if the movement being performed has balance of efforts, and is within a healthy range, preventing future injuries and accelerating recovery. | x | x |
| Movement magnitude | Motion as means to baseline accelerations and overall gait (magnitude). Crossing data from EMG and accelerometers it is possible to determine movement acceleration and gait - it is possible to determine desired ranges of motion during recovery after surgeries/injuries. | x | x |
| Muscle activity tracking | Muscle activity and motion as an indicator of activity level. Patient's activity level (e.g. recovery from heart surgery, diabetes patients). | x | x |
| Symmetry | Athlete has a strained right calf; applies patches to right and left calves, baselines abnormal right calf performance against left (relative measure); Put on a motion patch on leg during rehab activity to see how the muscle and movement activity using both a baseline sensor on one leg and on the other. Look for relative improvements. The quantitative measure is used to determine how close the injured and healthy legs are in performance and motion. Dimension of | x | x |

TABLE I-continued

| Example Performance | Description of Example Implementation To Determine Example Performance | Accelerometer | EMG |
|---|---|---|---|
| | the metric does not matter, just relative improvement or change. | | |

The non-limiting example implementations of Table I can be implemented using any of the systems, apparatus and methods described herein.

Figure 24A:
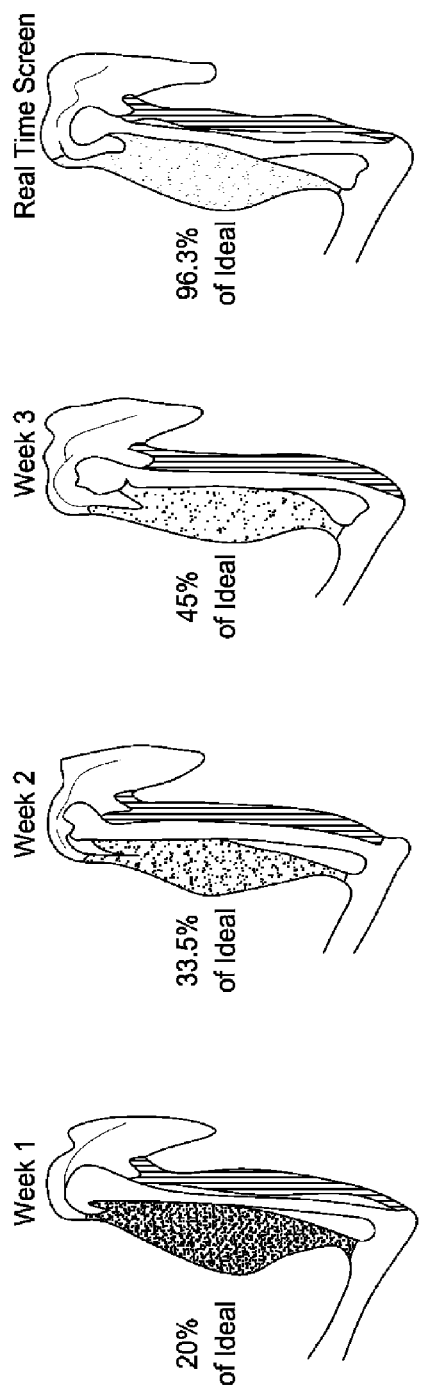
FIGS. 24A and 24B show an example of use of the example conformal sensor systems for determining a user's readiness to return to normal activity, according to the principles herein.
Figure 24B:
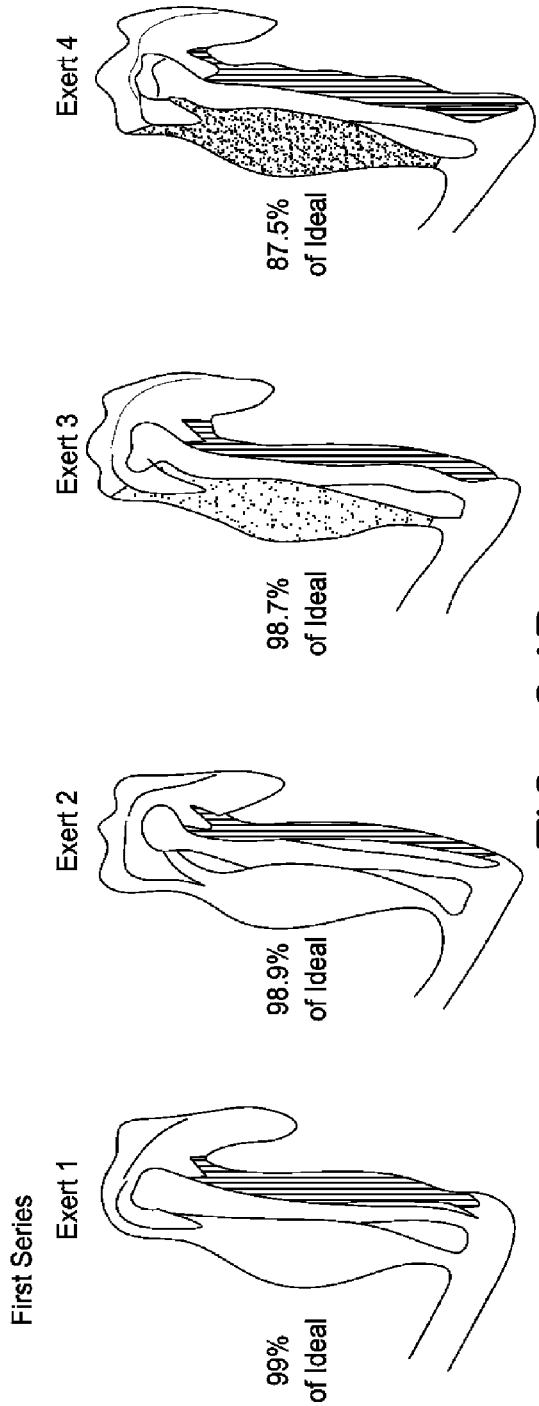

FIGS. 24A and 24B show an example of use of the example conformal sensor systems for a performance measure that determines a user's readiness to return to normal activity (such as work or playing sports). For example, the measures of the muscle activity and motion can be analyzed to provide an indicator of readiness for return to work, play or other post injury. In an example, it is possible to determine a baseline for the user motion (e.g., from measures of activation, acceleration, and/or activity range) and muscle activity, to utilize as a point of comparison throughout rehabilitation. In this non-limiting example, the conformal sensor system can be disposed on a portion of an upper arm. The example of FIG. 24A shows an example display of an assessment of the subject's muscle activity post injury. The display can be provided in real-time, on demand, or at different time intervals. The quality of movement can be assessed as a percentage of a desired (ideal) value (e.g., set at 100%). The display can be configured to display color-coded images of certain muscle groups visualizing the ratio between extensor and flexor muscles. In the example of FIG. 24A, the subject's movement can be analyzed to determine if the movement being performed has balance of efforts, and is within a healthy range. Such analysis can be used to reduce or prevent future injuries and accelerate recovery. FIG. 24B shows an example display of a series of four repetitions, where analysis of the measurements indicate declining performance. The indication of declining performance can be used to indicate lack of endurance. For example, the display of provides an indication that, after a number of repetitions, the extensor muscle is compensating, thereby indicating declining performance.

Figure 25:
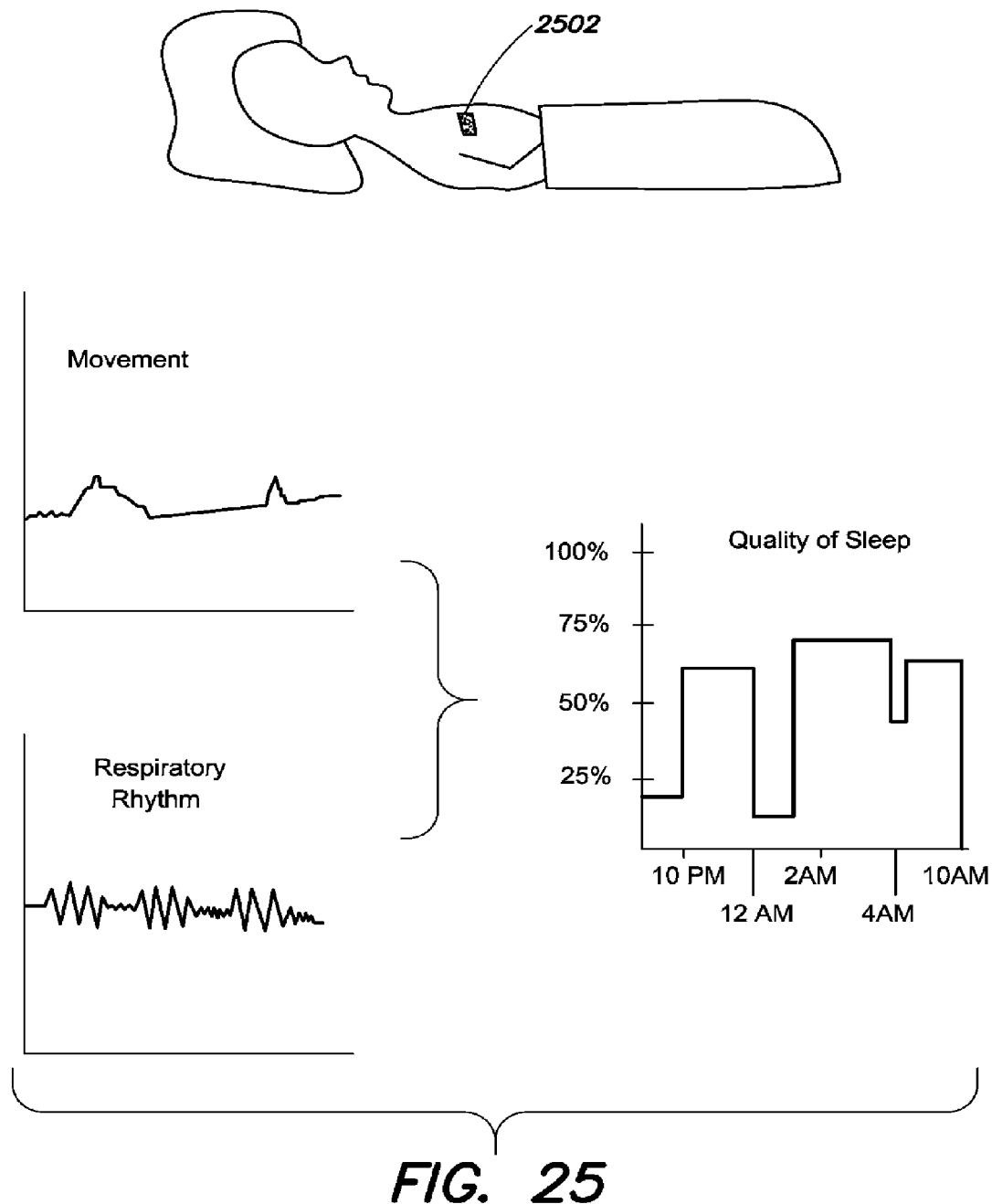
FIG. 25 shows an example of use of the example conformal sensor systems for use for sleep tracking, according to the principles herein.

FIG. 25 shows an example of use of the example conformal sensor systems for use for performance measure that operates for sleep tracking. In this example, the measurements of muscle activity and/or motion can be used to provide an indicator of quality of sleep. Example conformal sensor system 2502 can be disposed on or otherwise coupled to the thoracic diaphragm, to measure respiratory rhythms and movement. In an example, analysis of the muscle activity can be used as an indicator of a subject's relaxation level and bruxism. Analysis of data from measurements using the accelerometer and EMG can be combined to provide an indication of the user's quality of sleep, including in a feedback, to assist a user in implementing new sleeping habits to maximize rest and recovery.

In an example implementation, the conformal sensor system can be configured to maintain a low-power status at a time that no measurement is being performed. In an example, the conformal sensor system can be configured with a low-power on-board energy supplying component (e.g., a low-power battery). In an example, the conformal sensor system can be configured with no on-board energy component, and energy may be acquired through inductive coupling or other form of energy harvesting. In these example implementations, the sensor component(s) may be maintained substantially dormant, in a low-power state, or in an OFF state, until a triggering event occurs. For example, the triggering event can be that the body part or object, to which the system is coupled of disposed on, undergoes motion (or where applicable, muscle activity) above a specified threshold range of values or degree. Examples of such motion could be movement of an arm or other body part, such as but not limited to a bicep or quadriceps movement during physical exertion, a fall (e.g., for a geriatric patient), or a body tremor, e.g., due to an epileptic incident, a Palsy, or Parkinson's. Other examples of such motion could be movement of the object, e.g., a golf club swing, movement of a ball, etc. In another example, the conformal sensor system may include a near-field component (NFC), and the triggering event may be registered using the NFC component. In other examples, the triggering event may be a sound or other vibration, a change in light level (e.g., a LED) or a magnetic field, temperature (e.g., change in external heat level or blood rushing to an area), or an EEG, a chemical or a physiological measure (e.g., environment pollen or pollution level, or blood glucose level). In an example, the triggering event may be initiated at regular time intervals. The system can be configured such that occurrence of the triggering event causes triggering of the micro-controller; the micro-controller then be configured to cause activation of the accelerometer and/or the EMG component, or other sensor component, of the conformal sensor system to take a measurement.

In an example implementation, the conformal sensor system may include one or more components for administering or delivering an emollient, a pharmaceutical drug or other drug, a biologic material, or other therapeutic material. In an example, the components for administering or delivery may include a nanoparticle, a nanotube, or a microscale component. In an example, the emollient, pharmaceutical drug or other drug, biologic material, or other therapeutic material may be included as a coating on a portion of the conformal sensor system that is proximate to the body part. On occurrence of a triggering event (such as any triggering event described hereinabove), the conformal sensor system can be configured to trigger the delivery or administering of the emollient, drug, biologic material, or other therapeutic material. The occurrence of the triggering event can be a measurement of the accelerometer and/or the EMG or other sensor component. On the triggering event, the micro-controller can be configured to cause activation of the one or more components for the administering or delivery. The delivery or administering may be transdermally. In some examples, the amount of material delivered or administered may be calibrated, correlated or otherwise modified based on the magnitude of the triggering event, e.g., where triggering event is based on magnitude of muscle movement, a fall, or other quantifiable triggering event. In some examples, the system can be configured to heat a portion of the body part, e.g., by passing a current through a resistive element, a metal, or other element, that is proximate to the portion of the body part. Such heating may assist in more expedient deliver or administering of the emollient, drug, biologic material, or other therapeutic material to the body part, e.g., transdermally.

In an example implementation, the conformal sensor system may include one or more components for administering or delivering insulin, insulin-based or synthetic insulin-related material. In an example, the insulin, insulin-based or synthetic insulin-related material may be included as a coating on a portion of the conformal sensor system that is proximate to the body part. On occurrence of a triggering event (such as any triggering event described hereinabove), the conformal sensor system can be configured to trigger the delivery or administering of the insulin, insulin-based or synthetic insulin-related material. The occurrence of the triggering event can be a measurement of the accelerometer and/or the EMG or other sensor component. On the triggering event, the micro-controller can be configured to cause activation of the one or more components for the administering or delivery of the insulin, insulin-based or synthetic insulin-related material. The delivery or administering may be transdermally. the amount of material delivered or administered may be calibrated, correlated or otherwise modified based on the magnitude of the triggering event, (e.g., blood glucose level).

Also disclosed herein are methods of making and methods of using any of the conformal sensor devices and conformal sensor systems described above. By way of non-limiting example, methods of assembling a conformal sensor device for analyzing at least a portion of a user are disclosed. In at least some embodiments, the method includes: providing a power supply operable to power the conformal sensor device; providing a memory device storing microprocessor executable instructions; providing a microprocessor operable to execute the microprocessor executable instructions; providing a sensor device operable to obtain at least one measurement of the user; providing a wireless communication component operable to transmit data indicative of the at least one measurement obtained by the at least one sensor; and embedding in or on a flexible substrate the power supply, the memory device, the microprocessor, the sensor device, and the wireless communication component. The method may optionally include, singly, collectively, in any order and/or in any combination: electrically connecting (e.g., via a plurality of flexible interconnects embedded on or within the flexible substrate) one or more or all of the power supply, the memory device, the microprocessor, the sensor device, and the wireless communication component; providing a conformal electrode coupled with an electrode connector configured to contact the portion of the user, and embedding the conformal electrode and the electrode connector in or on the flexible substrate; providing a power regulator, and embedding the power regulator in or on the flexible substrate; providing a voltage controller, and embedding the voltage controller in or on the flexible substrate; and/or, providing a power transfer coil operable to facilitate charging the rechargeable battery, and embedding the power transfer coil in or on the flexible substrate. As some other options: the sensor device includes an accelerometer or a gyroscope, or both; the sensor device includes a hydration sensor, a temperature sensor, an electromyography (EMG) component, an electroencephalogram (EEG) component, or an electrocardiogram (EKG) component, or any combination thereof; the wireless communication component includes a flexible antenna embedded on or within the at least one flexible substrate; the wireless communication component includes a Bluetooth® low energy (BLTE) communications link; the conformal sensor device has a thickness of about 1 mm or less, a width of about 2 cm or less, and a height of about 10 cm or less; the conformal sensor device is operable to continuously monitor and provide continuous feedback on muscle activity, body part motion, or electrophysiological measurements, or any combination thereof; the power supply includes a rechargeable battery; and/or the flexible substrate is a stretchable polymeric patch surrounding the power supply, the memory device, the microprocessor, and the wireless communication component.

Also disclosed are methods of assembling a conformal sensor assembly for analyzing an individual. In at least some embodiments, the method includes: providing a flexible substrate operable to attach to a portion of the individual; providing a power supply; providing a microprocessor operable to execute microprocessor executable instructions; providing a sensor device operable to obtain at least one measurement of the user; and attach to the flexible substrate the power supply, the microprocessor, and the sensor device.

Also disclosed are methods of assembling a conformal sensor system for monitoring a user. In at least some embodiments, the method includes: electrically coupling a memory device to a microprocessor via a flexible interconnect, the memory device storing microprocessor executable instructions, the microprocessor being operable to execute the microprocessor executable instructions; electrically coupling a sensor device to the microprocessor via a flexible interconnect, the sensor device being operable to obtain at least one measurement of the user; electrically coupling a wireless communication component to the microprocessor, the wireless communication component being operable to transmit data indicative of the at least one measurement obtained by the sensor; and electrically coupling a power supply to the memory device, the microprocessor, the sensor device, and the wireless communication component.

Also disclosed are methods of using conformal sensor systems. The conformal sensor system includes a flexible substrate with a power supply, a sensor device and a microprocessor attached or coupled to the flexible substrate. The microprocessor is operable to execute microprocessor executable instructions. The sensor device is operable to obtain at least one measurement of the user. In at least some embodiments, the method includes: attaching or coupling the conformal sensor system to the skin of a user; and transmitting information based on the data by the sensor device.

Examples of the subject matter and the operations described herein can be implemented in digital electronic circuitry, or in computer software, firmware, or hardware, including the structures disclosed in this specification and their structural equivalents, or in combinations of one or more of them. Examples of the subject matter described herein can be implemented as one or more computer programs, i.e., one or more modules of computer program instructions, encoded on computer storage medium for execution by, or to control the operation of, data processing apparatus. The program instructions can be encoded on an artificially generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" or "computing device" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, software, software application, script, application or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatuses can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor receives instructions and data from a read only memory or a random access memory or both. The essential elements of a computer are a processor for performing actions in accordance with instructions and one or more memory devices for storing instructions and data. Generally, a computer can include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), for example. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, examples of the subject matter described herein can be implemented on a computer having a display device, e.g., a CRT (cathode ray tube), plasma, or LCD (liquid crystal display) monitor, for displaying information to the user and a keyboard and a pointing device, e.g., a mouse, touch screen or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Examples of the subject matter described herein can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system such as system 400 or system 100 can include clients and servers. A client and server are generally remote from each other and typically interact through a communication network. The relationship of client and server arises by virtue of computer programs running on the respective computers and having a client-server relationship to each other. In some examples, a server transmits data to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular embodiments of the systems and methods described herein. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In some cases, the actions recited in the claims can be performed in a different order and still achieve desirable results. In addition, the processes depicted in the accompanying figures do not necessarily require the particular order shown, or sequential order, to achieve desirable results.

In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

What is claimed is:

1. A conformal sensor device for analyzing a user, the conformal sensor device comprising:
    at least one flexible substrate configured to substantially conform to a surface of a portion of the user;
    at least one power supply embedded on or within the at least one flexible substrate and being configured to power the conformal sensor device;
    at least one memory device embedded on or within the at least one flexible substrate and storing microprocessor executable instructions;
    at least one microprocessor embedded on or within the at least one flexible substrate, the at least one microprocessor being communicatively coupled to the at least one memory device and being configured to execute the microprocessor executable instructions;
    at least one sensor device embedded on or within the at least one flexible substrate and being configured to generate sensor data representative of at least one measurement of the user;
    an analyzer configured to (i) quantify one or more performance parameters based on the sensor data and (ii) compare the one or more performance parameter to one or more predetermined performance threshold values to determine an indication of the performance of the user, the one or more performance parameters including baseline symmetry determined as function of a range of motion of a flexor muscle of the user and a range of motion of an extensor muscle of the user; and
    at least one wireless communication component embedded on or within the at least one flexible substrate and being configured to transmit data indicative of the indication of the performance of the user.

2. The conformal sensor device of claim 1, further comprising a plurality of flexible interconnects embedded on or within the at least one flexible substrate and electrically connecting the at least one power supply, the at least one memory device, the at least one microprocessor, the at least one sensor device, the at least one wireless communication component, or any combination thereof.

3. The conformal sensor device of claim 1, wherein the least one sensor device includes an accelerometer, a gyroscope, or both.

4. The conformal sensor device of claim 1, wherein the least one sensor device includes a hydration sensor, a temperature sensor, an electromyography (EMG) sensor, an electroencephalogram (EEG) sensor, an electrocardiogram (EKG) sensor, or any combination thereof.

5. The conformal sensor device of claim 1, wherein the at least one wireless communication component includes a flexible antenna embedded on or within the at least one flexible substrate.

6. The conformal sensor device of claim 1, wherein the at least one wireless communication component includes a Bluetooth® low energy (BLTE) communications link.

7. The conformal sensor device of claim 1, further comprising at least one conformal electrode embedded on or within the at least one flexible substrate and coupled with at least one electrode connector configured to contact the surface of the portion of the user.

8. The conformal sensor device of claim 1, having a thickness of 1 mm or less, a width of 2 cm or less, and a height of 10 cm or less.

9. The conformal sensor device of claim 1, wherein the at least one measurement of the user includes (a) acceleration data representative of an acceleration of the portion of the user, (b) physiological data representative of a physiological condition of the user, or any combination thereof.

10. The conformal sensor device of claim 1, wherein the at least one flexible substrate is a stretchable polymeric patch configured to at least partially surround the at least one power supply, the at least one memory device, the at least one microprocessor, and the at least one wireless communication component.

11. The conformal sensor device of claim 1, wherein the baseline symmetry includes determining a ratio of the range of motion of the flexor muscle of the user to the range of motion of an extensor muscle of the user.

12. The conformal sensor device of claim 1, wherein the one or more performance parameters quantified by the analyzer includes a readiness to return to normal activity determined as a function of a range of motion of a first muscle of the user and previously recorded baseline motion of the first muscle.

13. The conformal sensor device of claim 1, wherein the one or more performance parameters quantified by the analyzer includes a range of motion of a first muscle of the user during a rehabilitation activity and the one or more predetermined threshold parameters includes a previously recorded range of motion of the first muscle.

14. The conformal sensor device of claim 1, wherein the one or more performance parameters quantified by the analyzer includes movement pattern matching determined as function of a motion pattern of at least a first muscle of the user and the one or more predetermined threshold parameters includes a predefined desired motion pattern of the first muscle.

15. A conformal sensor assembly for analyzing an individual, the conformal sensor assembly comprising:
    a flexible substrate configured to substantially conform to a surface of a portion of the individual;
    a power supply attached or coupled to the flexible substrate;
    a microprocessor attached or coupled to the flexible substrate and being configured to execute microprocessor executable instructions;
    a sensor device attached or coupled to the flexible substrate and being configured to generate sensor data representative of at least one measurement of the user; and an analyzer configured to quantify one or more performance parameters based on the sensor data and compare the one or more performance parameters to one or more predetermined performance threshold values to determine an indication of the performance of the user, the one or more performance parameters including (i) baseline symmetry determined as function of a range of motion of a first muscle of the user and a range of motion of a second muscle of the user, (ii) a readiness to return to normal activity determined as a function of a range of motion of the first muscle of the user and previously recorded baseline motion of the first muscle, (iii) a range of motion of the first muscle of the user, or (iv) movement pattern matching determining as a function of a motion pattern of at least the first muscle of the user.

16. A conformal sensor system for monitoring a user, the conformal sensor system comprising:
a plurality of conformal, stretchable, and flexible sensors including a first conformal, stretchable, and flexible sensor configured to substantially conform to a first portion of skin of the user adjacent to a first muscle of the user and a second conformal, stretchable, and flexible sensor configured to substantially conform to a second portion of the skin of the user adjacent to a second muscle of the user, each of the plurality of conformal, stretchable, and flexible sensors including:
at least one flexible substrate configured to substantially conform to a surface of a portion of the user;
at least one memory device storing microprocessor executable instructions;
at least one microprocessor electrically coupled to the at least one memory device and being configured to execute the microprocessor executable instructions;
at least one sensor device electrically coupled to the at least one microprocessor and being configured to generate sensor data representative of at least one measurement of the user;
at least one wireless communication component electrically coupled to the at least one microprocessor and being configured to transmit data indicative of the indication of the performance of the user; and
at least one power supply electrically coupled to and configured to power the at least one memory device, the at least one microprocessor, the at least one sensor device and the at least one wireless communication component; and
an analyzer configured to (i) quantify one or more performance parameters based on sensor data from at least one of the plurality of conformal, stretchable, and flexible sensors and (ii) compare the one or more performance parameters to one or more predetermined performance threshold values to determine an indication of the performance of the user.

17. The conformal sensor system of claim 16, wherein each of the plurality of conformal, stretchable, and flexible sensors includes a plurality of flexible interconnects electrically coupling the at least one power supply, the at least one memory device, the at least one microprocessor, the at least one sensor device, and the at least one wireless communication component.

18. The conformal sensor system of claim 16, wherein the least one sensor device of each of the plurality of conformal, stretchable, and flexible sensors includes an accelerometer, a gyroscope, a hydration sensor, a temperature sensor, an electromyography (EMG) sensor, an electroencephalogram (EEG) sensor, an electrocardiogram (EKG) sensor, or any combination thereof.

19. The conformal sensor system of claim 16, wherein each of the plurality of conformal, stretchable, and flexible sensors includes at least one conformal electrode coupled with at least one electrode connector configured to contact a portion of skin of the user.

20. The conformal sensor system of claim 16, wherein the at least one flexible substrate of each of the plurality of conformal, stretchable, and flexible sensors is configured to attach directly to a portion of skin of the user.

21. The conformal sensor system of claim 20, wherein the at least one flexible substrate of each of the plurality of conformal, stretchable, and flexible sensors is attached directly to the portion of skin of the user via an adhesive.

22. The conformal sensor system of claim 16, wherein the one or more performance parameters quantified by the analyzer includes baseline symmetry determined as function of a range of motion of the first muscle of the user and a range of motion of the second muscle of the user.

23. The conformal sensor system of claim 22, wherein the first muscle is a flexor muscle of the user and the second muscle is an extensor muscle of the user.

* * * * *